(12) United States Patent
Ayalon et al.

(10) Patent No.: US 9,598,485 B2
(45) Date of Patent: Mar. 21, 2017

(54) ANTI-TAU ANTIBODIES AND METHODS OF USE

(71) Applicants: AC IMMUNE S.A., Lausanne (CH); Genentech, Inc., South San Francisco, CA (US)

(72) Inventors: Gai Ayalon, Moraga, CA (US); Danielle Marie Di Cara, San Francisco, CA (US); Isidro Hotzel, Brisbane, CA (US); Andrea Pfeifer, St-Legier (CH); Andreas Muhs, Cugy (CH); Maria Pihlgren, Mont-sur-Lausan (CH); Oskar Adolfsson, Bercher (CH)

(73) Assignees: AC IMMUNE S.A., Lausanne (CH); GENENTECH, INC., South San Francisco, CA (US)

( * ) Notice: Subject to any disclaimer, the term of this patent is extended or adjusted under 35 U.S.C. 154(b) by 1 day.

(21) Appl. No.: 14/773,332

(22) PCT Filed: Mar. 12, 2014

(86) PCT No.: PCT/US2014/024440
§ 371 (c)(1),
(2) Date: Sep. 5, 2015

(87) PCT Pub. No.: WO2014/150877
PCT Pub. Date: Sep. 25, 2014

(65) Prior Publication Data
US 2016/0024193 A1    Jan. 28, 2016

Related U.S. Application Data

(60) Provisional application No. 61/800,949, filed on Mar. 15, 2013.

(51) Int. Cl.
    *C07K 16/18* (2006.01)
    *C07K 16/44* (2006.01)
    *A61K 47/48* (2006.01)

(52) U.S. Cl.
    CPC ........ *C07K 16/18* (2013.01); *A61K 47/48538* (2013.01); *C07K 16/44* (2013.01); *C07K 2317/24* (2013.01); *C07K 2317/33* (2013.01); *C07K 2317/34* (2013.01); *C07K 2317/55* (2013.01); *C07K 2317/565* (2013.01); *C07K 2317/92* (2013.01)

(58) Field of Classification Search
    None
    See application file for complete search history.

(56) References Cited

U.S. PATENT DOCUMENTS

| | | |
|---|---|---|
| 5,004,697 A | 4/1991 | Pardridge |
| 5,112,596 A | 5/1992 | Malfroy-Camine |
| 5,268,164 A | 12/1993 | Kozarich et al. |
| 5,506,206 A | 4/1996 | Kozarich et al. |
| 5,686,416 A | 11/1997 | Kozarich et al. |
| 5,843,779 A | 12/1998 | Vandermeeren et al. |
| 6,514,221 B2 | 2/2003 | Hynynen et al. |
| 6,953,794 B2 | 10/2005 | Wischik et al. |
| 7,034,036 B2 | 4/2006 | Schoenhard |
| 7,220,833 B2 | 5/2007 | Nelson et al. |
| 7,408,027 B1 | 8/2008 | Mandelkow et al. |
| 8,012,936 B2 | 9/2011 | Sigurdsson et al. |
| 8,663,650 B2 | 3/2014 | Nicolau et al. |
| 8,748,386 B2 | 6/2014 | Sigurdsson |
| 2002/0025313 A1 | 2/2002 | Micklus et al. |
| 2002/0065259 A1 | 5/2002 | Schatzberg et al. |
| 2002/0086009 A1 | 7/2002 | Ishiguro et al. |
| 2003/0083299 A1 | 5/2003 | Ferguson et al. |
| 2003/0129186 A1 | 7/2003 | Beliveau et al. |
| 2003/0162695 A1 | 8/2003 | Schatzberg et al. |
| 2004/0131692 A1 | 7/2004 | Kreuter et al. |
| 2004/0265920 A1 | 12/2004 | Seubert et al. |
| 2005/0089473 A1 | 4/2005 | Black et al. |
| 2005/0124533 A1 | 6/2005 | Schatzberg et al. |
| 2005/0221391 A1 | 10/2005 | Davies |
| 2005/0261475 A1 | 11/2005 | Tseng et al. |
| 2008/0050383 A1 | 2/2008 | Sigurdsson et al. |
| 2008/0220449 A1 | 9/2008 | Vasan et al. |
| 2010/0285108 A1 | 11/2010 | Pfeifer et al. |
| 2011/0318358 A1 | 12/2011 | Sigurdsson et al. |
| 2012/0276009 A1 | 11/2012 | Pfeifer et al. |
| 2014/0255412 A1 | 9/2014 | Pfeifer et al. |
| 2014/0294731 A1 | 10/2014 | Pfeifer et al. |
| 2014/0302046 A1 | 10/2014 | Sigurdsson |

(Continued)

FOREIGN PATENT DOCUMENTS

| | | |
|---|---|---|
| CN | 102070718 | 5/2011 |
| EP | 2210901 | 7/2010 |

(Continued)

OTHER PUBLICATIONS

Chen 1995 "Enhancement and destruction of antibody function by somatic mutation: unequal occurrence is controlled by V gene combinatorial associations" EMBO 14(12):27842794.*
English translation of Search Report for Chinese Patent Application No. 201280060349.3, dated Jul. 20, 2015 (2 pages).
International Search Report and Written Opinion for PCT/EP2011/067604, mailed Apr. 3, 2012, 31 pages.
International Search Report and Written Opinion for PCT/EP2012/069783, mailed Jan. 25, 2013, 18 pages.
International Search Report and Written Opinion for PCT/US2013/032341, mailed Sep. 3, 2013, 13 pages.
International Search Report and Written Opinion for PCT Application No. PCT/US2014/024440, mailed Oct. 6, 2014 (14 pages).
Alonso et al., Abnormal phosphorylation of tau and the mechanism of Alzheimer neurofibrillary degeneration: sequestration of microtubule-associated proteins 1 and 2 and the disassembly of microtubules by the abnormal tau, PNAS, (1997), 94:298-303.

(Continued)

*Primary Examiner* — Adam M Weidner
(74) *Attorney, Agent, or Firm* — McNeill Baur PLLC

(57) ABSTRACT

The present invention relates to anti-Tau antibodies, such as antibodies that bind to a phosphorylated epitope on human Tau protein with high specificity and/or affinity, and methods of using the same.

66 Claims, 9 Drawing Sheets

(56) References Cited

U.S. PATENT DOCUMENTS

| | | |
|---|---|---|
| 2015/0175682 A1 | 6/2015 | Pfeifer et al. |
| 2015/0259406 A1 | 9/2015 | Pfeifer et al. |

FOREIGN PATENT DOCUMENTS

| | | |
|---|---|---|
| WO | WO 93/11231 | 6/1993 |
| WO | WO 96/13590 | 5/1996 |
| WO | WO 96/20218 | 7/1996 |
| WO | WO 96/29605 | 9/1996 |
| WO | WO 98/22120 | 5/1998 |
| WO | WO 2004/058258 | 7/2004 |
| WO | WO 2005/080986 | 9/2005 |
| WO | WO 2005/081872 | 9/2005 |
| WO | WO 2007/068105 | 6/2007 |
| WO | WO 2007/068411 | 6/2007 |
| WO | WO 2008/157302 | 12/2008 |
| WO | WO 2010/106127 | 9/2010 |
| WO | WO 2010/115843 A2 | 10/2010 |
| WO | WO 2010/144711 | 12/2010 |
| WO | WO 2011/013034 | 2/2011 |
| WO | WO 2012/045882 A2 | 4/2012 |
| WO | WO 2013/050567 | 4/2013 |
| WO | WO 2013/151762 A1 | 10/2013 |
| WO | WO 2013/166302 | 11/2013 |

OTHER PUBLICATIONS

Alonso et al., Mechanism of tau-induced neurodegeneration in Alzheimer disease and related tauopathies, Curr Alzheimer Res, (2008), 5:375-384.

Alving et al., Adjuvant effects of liposomes containing lipid A: enhancement of liposomal antigen presentation and recruitment of macrophages, Infect. Immun., 1992, 60:2438-2444.

Asuni et al., Immunotherapy targeting pathological tau conformers in a tangle mouse model reduces brain pathology with associated functional improvements, (2007), J Neurosc. 27 (34), 9115-29.

Bellucci et al., "Abnormal processing of tau in the brain of aged TgCRND8 mice," Neurobiol. Dis., 27(3): 328-338 (2007).

Bhaskar et al., Tyrosine phosphorylation of tau accompanies disease progression in transgenic mouse models of tauopathy, (2010) Neuropathol Appl Neurobiol, 36:462-477.

Boutajangout et al., "Passive immunization targeting pathological phospho-tau protein in a mouse model reduces functional decline and clears tau aggregates from the brain," J. Neurochem., 118: 658-667 (2011).

Braak et al., Neuropathological stageing of Alzheimer-related changes., 1991, Acta Neuropathol 82:239-259.

Braak et al., Staging of Alzheimer-related cortical destruction, (1993), Eur.Neurol., 33:403-408.

Chai et al., "Passive Immunization with Anti-Tau Antibodies in Two Transgenic Models," J. Biol. Chem., 286(39): 34457-34467 (2011).

D'Abramo et al., Tau passive immunotherapy in mutant P301L mice: antibody affinity versus specificity, (2013), PLoSone, 8:e62402, 10 pages.

D'Abramo et al., "Passive Immunization in JNPL3 Transgenic Mice Using an Array of Phospho-Tau Specific Antibodies," PLOS ONE, 10(8): e0135774 doi: 10.1371.pone.0135774, pp. 1-8 (2015).

Dominguez et al., Novel therapeutic strategies provide the real test for the amyloid hypothesis of Alzheimer's disease, Trends Pharmacol Sci, 2002, 23:324-330.

Dunn et al., "Fine mapping of the binding sites of monoclonal antibodies raised against the Pk tag," J. Immunol. Methods, 224(1-2): 141-150 (1999).

Gill et al., Direct brain infusion of glial cell line-derived neurotrophic factor in Parkinson disease, 2003, Nature Med. 9:589-595.

Greenberg et al. Hydrofluoric acid-treated tau PHF proteins display the same biochemical properties as normal tau, (1992), J Biol. Chem., 267:564-569.

Harlow et al., Antibodies: A Laboratory Manual (Cold Spring Harbor Laboratory, New York 1988 553-612.

Hirata-Fukae et al., Levels of soluble and insoluble tau reflect overall status of tau phosphorylation in vivo, (2009), Neurosci Lett, 450:51-55.

Hodgson, Making monoclonals in microbes, (1991) Bio/Technology, 9:421-425.

Hoffmann et al., Unique Alzheimer's disease paired helical filament specific epitopes involve double phosphorylation at specific sites, (1997), Biochemistry, 36, 8114-8124.

"Instructions for Authors", The Journal of Neuroscience, published [online] Jun. 29, 1998 Retrieved [online] from<https://web.archive.org/web/19980629153321/http://www.jneurosci.org/misc/itoa.shtml> Jan. 7, 2015.

Jicha et al., cAMP-dependent protein kinase phosphorylations on tau in Alzheimer's disease, (1999), J Neurosci, 19:7486-7494.

Kennedy et al., Protein-protein coupling reactions and the applications of protein conjugates, 1976, Clin. Chim. Acta 70:1-31.

Khaw et al., Technetium-99m labeling of antibodies to cardiac myosin Fab and to human fibrinogen, 1982, J. Nucl. Med. 23:1011-1019.

Lee et al., Phosphorylation of tau by fyn: implications for Alzheimer's disease, (2004), J Neurosci, 24:2304-2312.

Lewis et al., Neurofibrillary tangles, amyotrophy and progressive motor disturbance in mice expressing mutant (P301L) tau protein, (2000) Nature Genetics, 25:402-405.

Lichtenberg-Kraag et al., Phosphorylation-dependent epitopes of neurofilament antibodies on tau protein and relationship with Alzheimer tau, (1992), PNAS, 89:5384-5388.

Masliah et al., Effects of alpha-synuclein immunization in a mouse model of Parkinson's disease, (2005), Neuron, 46(6):857-68.

Masliah et al., Passive immunization reduces behavioral and neuropathological deficits in an alpha-synuclein transgenic model of Lewy body disease, (2011) PLoS ONE, vol. 6(4):e19338,17 pages.

Muhs et al., Liposomal vaccines with conformation-specific amyloid peptide antigens define immune response and efficacy in APP transgenic mice, (2007) Proc Natl Acad Sci USA, 104(23):9810-5.

Muyllaert et al, Transgenic mouse models for Alzheimer's disease: the role of GSK-3B in combined amyloid and tau-pathology, (2006) Rev Neurol, 162(10):903-907.

Muyllaert et al, Glycogen synthase kinase-3beta, or a link between amyloid and tau pathology?, (2008) Genes Brain Behav., Suppl. 1:57-66.

Neuwelt, Implication of the Blood-Brain Barrier and its Manipulation, vols. 1 & 2, Plenum Press, N. Y. (1989), TOC Only.

Nicolau et. al., A liposome-based therapeutic vaccine against beta-amyloid plaques on the pancreas of transgenic NORBA mice, (2002) Proc Natl. Acad. Sci USA 99:2332-2337.

Nicoll et al., Neuropathology of human Alzheimer disease after immunization with amyloid-beta peptide: a case report, (2003) Nature Med, 9:448-452.

Oddo et al., Abeta immunotherapy leads to clearance of early, but not late, hyperphosphorylated tau aggregates via the proteasome, (2004) Neuron, 43:321-332.

Oddo et al., Reduction of soluble Abeta and tau, but not soluble Abeta alone, ameliorates cognitive decline in transgenic mice with plaques and tangles, (2006), J Biol Chem, 281:39413-39423.

Otvos et al., Monoclonal antibody PHF-1 recognizes tau protein phosphorylated at serine residues 396 and 404, (1994), J Neurosci Res., 39:669-673.

Papanastassiou et al., The potential for efficacy of the modified (ICP 34.5(-)) herpes simplex virus HSV1716 following intratumoural injection into human malignant glioma: a proof of principle study, 2002, Gene Therapy 9:398-406.

Queen et al., A humanized antibody that binds to the interleukin 2 receptor, (1989) Proc. Natl Acad Sci USA, 86:10029-10032.

Rankin et al., "Tau Phosphorylation by GSK-3beta Promotes Tangle-Like Filament Morphology," Mol. Neurodegener. 2007. 2:12.

Reig et al., Immunogold labelling of paired helical filaments and amyloid fibrils by specific monoclonal and polyclonal antibodies, (1995), Acta Neuropathol., 90:441-447.

(56) References Cited

OTHER PUBLICATIONS

Ribe et al., Accelerated amyloid deposition, neurofibrillary degeneration and neuronal loss in double mutant APP/tau transgenic mice, (2005) Neurobiol Dis, 20(3):814-22.
Roberson et al, Reducing endogenous tau ameliorates amyloid beta-induced deficits in an Alzheimer's disease mouse model, (2007) Science, 316(5825):750-4.
Roder et al., Phosphorylation-dependent monoclonal Tau antibodies do not reliably report phosphorylation by extracellular signal-regulated kinase 2 at specific sites, (1997), J Biol Chem, 272:4509-4515.
Rosenmann et al., Tauopathy-like abnormalities and neurologic deficits in mice immunized with neuronal tau protein, (2006) Arch Neurol, 63(10):1459-67.
Rousseaux et al. Methods Enzymology, Optimal conditions for the preparation of proteolytic fragments from monoclonal IgG of different rat IgG subclasses., (1986), Academic Press 121:663-69.
Sahara et al., "Phosphorylated p38MAPK specific antibodies cross-react with sarkosyl-insoluble hyperphosphorylated tau proteins," J. Neurochem., 90: 829-838 (2004).
Schurs et al., Enzyme-Immunoassay, 1977, Clin. Chim Acta 57:1-40.
Sela et al., Therapeutic vaccines: realities of today and hopes for the future, Drug Discov Today, 2002, 7:664-673.
Singer et al., Characterization of Phosphorylation Dependent Antibodies to Sutdy the Phosphorylation Status of the Tau Protein, (2005), Intl J Peptide Res Therapeutics, 11:279-289.
Singer et al., Immuno-PCR-based quantification of multiple phosphorylated tau-epitopes linked to Alzheimer's disease, (2009), Anal Bioanal Chem, 395:2263-2267.
Staubli et al., Aniracetam has Proportionately Smaller Effects on Synapses Expressing Long-Term Potentiation: Evidence that Receptor Changes Subserve LTP, Psychobiology, 1990, 18:377-381.
Tabira, Immunization therapy for Alzheimer disease: a comprehensive review of active immunization strategies, Tohoku J Exp Med., 2010, 220:95-106.
Terwel et al., Changed conformation of mutant Tau-P301L underlies the moribund tauopathy, absent in progressive, nonlethal axonopathy of Tau-4R/2N transgenic mice, (2006) J Biol Chem, 280:3963-3973.
Terwel et al, Amyloid activates GSK-3beta to aggravate neuronal tauopathy in bigenic mice, (2008) Am J pathol., 172(3):786-98.
Torreilles et al., Binding specificity of monoclonal antibody AD2: influence of the phosphorylation state of tau, (2000), Molecular Brain Res., 78:181-185.
Urushitiani et al., Therapeutic effects of immunization with mutant superoxide dismutase in mice models of amyotrophic lateral sclerosis, (2007) Proc. Natl Acad Sci USA, 104(79):2495-500.
Vandebroek et al., Identification and isolation of a hyperphosphorylated, conformationally changed intermediate of human protein tau expressed in yeast, (2005), Biochemistry, 44:11466-11475.
Vandebroek et al., "Phosphorylation and Aggregation of Protein Tau in Humanized Yeast Cells and in Transgenic Mouse Brain"; 7th International Conference on Alzheimer's and Parkinson's Disease, Sorrento, Italy, Mar. 9-13, 2005, pp. 15-19.
Vandebroek et al., Microtubule binding and clustering of human Tau-4R and Tau-P301L proteins isolated from yeast deficient in orthologues of glycogen synthase kinase-3beta or cdk5, (2006), J Biol Chem 281:25388-25397.
Vanhelmont et al., Serine-409 phosphorylation and oxidative damage define aggregation of human protein tau in yeast, (2010), Fems Yeast Research, 10:992-1005.
Wagner et al., The crossflow injection technique: an improvement of the ethanol injection method, (2002) Journal of Liposome Research, 12(3):259-270.
Yang et al., "CDR Walking Mutagenesis for the Affinity Maturation of a Potent Human Anti-HIV-1 Antibody into the Picomolar Range," J. Mol. Biol., 254: 392-403 (1995).
Zemlan, F. et al., "Monoclonal Antibody PHF-9 Recognizes Phosphorylated Serine 404 of TauProtein and Labels Paired Helical Filaments," Journal of Neuroscience Research, Oct. 1, 1996, vol. 46, No. 1, pp. 90-97.
Zheng-Fischhoefer et al., Sequential phosphorylation of Tau by glycogen synthase kinase-3beta and protein kinase A at Thr212 and Ser214 generates the Alzheimer-specific epitope of antibody AT100 and requires a paired-helical-filament-like conformation, (1998), Euro J Biochem, 252:542-552.

\* cited by examiner

| Peptide | Peptide sequence<br>X = phosphoserine | |
|---|---|---|
| pS404, pS409 | Biotin – linker – GDTXPRHLXNVSSTGSID | SEQ ID NO:94 |
| Non-phospho. | Biotin – linker – GDTSPRHLSNVSSTGSID | SEQ ID NO:95 |
| pS404 | Biotin – linker – GDTXPRHLSNVSSTGSID | SEQ ID NO:96 |
| pS409 | Biotin – linker – GDTSPRHLXNVSSTGSID | SEQ ID NO:97 |

ANTI-TAU ANTIBODIES AND METHODS OF USE

FIELD OF THE INVENTION

The present invention relates to anti-Tau antibodies, such as antibodies that bind to a phosphorylated epitope on Tau protein with high specificity and/or high affinity, and methods of using the same.

BACKGROUND

Neurofibrillary tangles and neuropil threads (NTs) are the major neuropathological hallmarks of Alzheimer's Disease (AD). NTs are composed of the microtubule-associated Tau protein that has undergone posttranslational modifications including phosphorylation, and develop by aggregation of hyperphosphorylated Tau conformers. AD shares this pathology with many neurodegenerative tauopathies, in particularly with certain types of frontotemporal dementia (FTD). Tau protein appears to be a major player in the cognitive demise in AD and related neurodegenerative tauopathies.

Therapeutic approaches that target Tau protein are scarce and comprise mainly inhibitors of the kinases that are thought to increase the phosphorylation of Tau to pathological levels, and compounds that block the cytoplasmic aggregation of hyper-phosphorylated Tau protein. These approaches suffer various draw-backs of specificity and efficacy. Mouse antibodies that bind to phosphorylated pathological Tau conformers have been described previously, e.g., in WO 2012/045882. However, there is still a need for additional passive and/or active immunotherapies that work to counteract the pathological protein conformers that are known or presumed to cause neurodegenerative disorders, such as amyloid pathology in AD caused, for example, by intra-neuronal aggregates of hyperphosphorylated protein Tau that are as typical for AD as amyloid.

SUMMARY

The present invention relates to anti-Tau antibodies, such as antibodies that bind to a phosphorylated epitope on Tau protein with high specificity and/or high affinity, and methods of using the same.

In one aspect, the present invention relates to an isolated antibody that binds to a phosphorylated epitope of Tau protein, wherein the antibody comprises at least one sequence selected from the group consisting of HVR-L1, HVR-L2 and HVR-L3, wherein: (a) HVR-L1 comprises the amino acid sequence $X_1SSQX_2LX_3X_4X_5X_6GX_7TYX_8H$ (SEQ ID NO:89), wherein $X_1$=R or T; $X_2$=S, R or V; $X_3$=V, I or R; $X_4$=H or R; $X_5$=S, R, G or K; $X_6$=H, N, R, K or G; or R; and $X_8$=L or V; (b) HVR-L2 comprises the amino acid sequence $KVX_9X_{10}RFX_{11}$ (SEQ ID NO:90), wherein $X_9$=S, K or R; K or H; and $X_{11}$=S, F, G, K, R, Y or L; and (c) HVR-L3 comprises the amino acid sequence $SQTX_{12}X_{13}FPX_{14}T$ (SEQ ID NO:91), wherein $X_{12}$=A or R; $X_{13}$=H, R, Q or Y; $X_{14}$=Y or R; and wherein the antibody does not comprise an HVR-L1, HVR-L2 and HVR-L3 wherein the HVR-L1 amino acid sequence is RSSQSLVHSHGKTYLH (SEQ ID NO:15) or RSSQRLVHSHGKTYLH (SEQ ID NO:92); the HVR-L2 amino acid sequence is KVSNRFS (SEQ ID NO:16); and the HVR-L3 amino acid sequence is SQTAHFPYT (SEQ ID NO:30).

In certain embodiments, the antibody according to the present invention binds to a phosphorylated epitope of Tau protein which includes a phosphorylated amino acid residue selected from the group consisting of: serine at position 409 of human tau (SEQ ID NO:59); serine at position 404 of human tau (SEQ ID NO:59); and serine at position 404 and 409 of human tau (SEQ ID NO:59).

In some embodiments, the antibody according to the present invention comprises at least one sequence selected from the group consisting of HVR-H1, HVR-H2 and HVR-H3, wherein HVR-H1 comprises the amino acid sequence GYTFTDYYMN (SEQ ID NO:33); HVR-H2 comprises the amino acid sequence DINPNRGGTTYNQKFKG (SEQ ID NO:34); and HVR-H3 comprises the amino acid sequence YYAVGY (SEQ ID NO:35).

In specific embodiments, the antibody according to the present invention comprises at least one sequence selected from the group consisting of HVR-L1, HVR-L2 and HVR-L3, wherein (a) HVR-L1 comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14; (b) HVR-L2 comprises the amino acid sequence selected from the group of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and (c) HVR-L3 comprises the amino acid sequence selected from the group of SEQ ID NO:27, SEQ ID NO:28, SEQ ID NO:29, SEQ ID NO:30, SEQ ID NO:31, SEQ ID NO:32.

In specific embodiments, the antibody according to the present invention comprises an HVR-L1, HVR-L2 and HVR-L3, wherein (a) HVR-L1 comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14; (b) HVR-L2 comprises the amino acid sequence selected from the group of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and (c) HVR-L3 comprises the amino acid sequence selected from the group of SEQ ID NO:27, SEQ ID NO:28, SEQ ID NO:29, SEQ ID NO:30, SEQ ID NO:31, SEQ ID NO:32.

In one embodiment, the antibody according to the present invention comprises (a) HVR-L1 comprising the amino acid sequence of SEQ ID NO:1; (b) HVR-L2 comprising the amino acid sequence of SEQ ID NO:16; and (c) HVR-L3 comprising the amino acid sequence of SEQ ID NO:27.

In one embodiment, the antibody according to the present invention comprises (a) HVR-L1 comprising the amino acid sequence of SEQ ID NO:2; (b) HVR-L2 comprising the amino acid sequence of SEQ ID NO:17; and (c) HVR-L3 comprising the amino acid sequence of SEQ ID NO:27.

In one embodiment, the antibody according to the present invention comprises (a) HVR-L1 comprising the amino acid sequence of SEQ ID NO:8; (b) HVR-L2 comprising the amino acid sequence of SEQ ID NO:21; and (c) HVR-L3 comprising the amino acid sequence of SEQ ID NO:29.

In one embodiment, the antibody according to the present invention comprises (a) HVR-L1 comprising the amino acid sequence of SEQ ID NO:14; (b) HVR-L2 comprising the amino acid sequence of SEQ ID NO:25; and (c) HVR-L3 comprising the amino acid sequence of SEQ ID NO:31, In one embodiment, the antibody according to the present invention comprises (a) HVR-L1 comprising the amino acid sequence of SEQ ID NO:9; (b) HVR-L2 comprising the amino acid sequence of SEQ ID NO:17; and (c) HVR-L3 comprising the amino acid sequence of SEQ ID NO:31.

In particular embodiments, the antibody according to the present invention comprises a light chain variable domain (VL) sequence selected from the group consisting of SEQ ID NO:36, SEQ ID NO:37, SEQ ID NO:44, SEQ ID NO:54, and SEQ ID NO:55, or a VL having at least 90%, at least 95%, or at least 98% sequence identity to the amino acid sequence selected from the group consisting of SEQ ID NO:36, SEQ ID NO:37, SEQ ID NO:44, SEQ ID NO:54, and SEQ ID NO:55.

In certain embodiment, the antibody according to the present invention comprises a heavy chain variable domain (VH) sequence of SEQ ID NO:58, or a VH sequence having at least 90%, at least 95%, or at least 98% sequence identity to the amino acid sequence of SEQ ID NO:58.

In some embodiments, the antibody according to the present invention is a monoclonal antibody. In some embodiments, the antibody according to the present invention is a human, humanized, or chimeric antibody. In particular embodiments, the antibody according to the present invention is a human or humanized antibody.

In specific embodiments, the antibody according to the present invention is a full length IgG1 antibody. In other specific embodiments, the antibody according to the present invention is a full length IgG4 antibody. In other specific embodiments, the antibody according to the present invention is a full length IgG1 N297G antibody. In yet other specific embodiments, the antibody according to the present invention is an antibody fragment that binds to a phosphorylated epitope on a human Tau protein.

In certain embodiments, the antibody according to the present invention binds to the Tau protein which is a human Tau protein (e.g., the Tau protein of SEQ ID NO:59).

In some embodiments, the antibody according to the present invention binds to a phosphorylated epitope of Tau protein but does not bind to the same epitope of the Tau protein which is not phosphorylated. In some embodiments, the antibody according to the present invention binds to a phosphorylated epitope of Tau protein, but binds to the same epitope of the Tau protein which is not phosphorylated with a substantially reduced affinity. In particular embodiments, the antibody according to the present invention binds to a phosphorylated epitope of Tau protein, wherein the Tau protein comprises the amino acid sequence of SEQ ID NO:59. In one embodiment, the antibody according to the present invention binds to a phosphorylated epitope of human Tau protein comprising amino acid residues 404-411 (SEQ ID NO:59).

In specific embodiments, the antibody according to the present invention binds to a phosphorylated epitope of Tau protein with a Kd of between about 1 nm and 45 nM. In one embodiment, the antibody according to the present invention binds to a phosphorylated epitope of Tau protein with a Kd of ≤1 nM. In specific embodiments, the antibody according to the present invention binds to a phosphorylated epitope of Tau protein with a dissociation rate constant of $\leq 5 \times 10^{-3}$ s$^{-1}$. In specific embodiments, the antibody according to the present invention binds to a phosphorylated epitope of Tau protein with an association rate constant of $\geq 3 \times 10^{5}$ M$^{-1}$ s$^{-1}$ or $\geq 7 \times 10^{5}$ M$^{-1}$ s$^{-1}$.

In some embodiments, the antibody according to the present invention binds to Tau protein which is an aggregated microtubule-associated and/or hyperphosphorylated Tau protein such as that present in paired helical filaments (PHF).

In another aspect, the present invention relates to an isolated nucleic acid encoding any of the antibodies described herein.

In yet another aspect, the present invention relates to a host cell comprising the isolated nucleic acid encoding any of the antibodies described herein. In certain embodiments, the present invention relates to methods of producing an antibody comprising culturing such host cell so that the antibody is produced.

In yet another aspect, the present invention relates to an immunoconjugate comprising any of the antibodies described herein and a cytotoxic agent.

In a further aspect, the present invention relates to a pharmaceutical formulation comprising any of the antibodies described herein and a pharmaceutically acceptable carrier.

In some aspects, the present invention relates to an antibody described herein (any of the antibodies described herein) for use as a medicament. In some embodiments, the antibody according to the present invention is for use in treating a Tau protein associated disease or disorder in an individual. In particular embodiments, the antibody according to the present invention is for treating a tauopathy in an individual. In a specific embodiment, the antibody according to the present invention is for use in treating Alzheimer's Disease (AD) in an individual. In a specific embodiment, the antibody according to the present invention is for use in treating frontotemporal dementia (FTD) in an individual. In some embodiments, the antibody according to the present invention is for use in treating an impairment in or loss of cognitive functions in an individual. In a specific embodiment, the antibody according to the present invention is for use in reducing or modulating the total levels of Tau protein in the brain of an individual. In a specific embodiment, the antibody according to the present invention is for use in reducing or modulating the total levels of a phosphorylated or hyperphosphorylated Tau protein in the brain of an individual.

In certain embodiments, the antibody according to the present invention is for use in the manufacture of a medicament for treating a disease or disorder in an individual selected from: a Tau protein associated disease or disorder, tauopathy, AD, FTD, and an impairment in or loss of cognitive functions in an individual. In some embodiments, the antibody according to the present invention is for use in the manufacture of a medicament for reducing or modulating the total levels of Tau protein in the brain of an individual. In some embodiments, the antibody according to the present invention is for use in the manufacture of a medicament for reducing or modulating the levels of phosphorylated or hyperphosphorylated Tau protein in the brain of an individual.

In certain embodiments, the present invention relates to methods of treating an individual having a disease or disorder selected from: a Tau protein associated disease or disorder, tauopathy, AD, FTD, and an impairment in or loss of cognitive functions, comprising administering to the individual an effective amount of an antibody described herein (any of the antibodies described herein). In one embodiment, the disease or disorder treated in accordance with the methods of the invention is AD.

In certain embodiments, the present invention relates to methods of reducing the levels of total Tau protein, phosphorylated Tau protein or hyperphosphorylated Tau protein in the brain of an individual, comprising administering to the individual an effective amount of an antibody described herein (any of the antibodies described herein) to reduce the levels of total Tau protein, phosphorylated Tau protein or hyperphosphorylated Tau protein in the brain of the individual. In some embodiments, the present invention relates to methods of modulating the levels of total Tau protein, phosphorylated Tau protein or hyperphosphorylated Tau protein in the brain of an individual, comprising administering to the individual an effective amount of an antibody described herein (any of the antibodies described herein) to modulate the levels of total Tau protein, phosphorylated Tau protein or hyperphosphorylated Tau protein in the brain of the individual.

In specific embodiments, an individual treated in accordance with the methods described herein is a human. In specific embodiments, the antibodies are for administration to a human. In specific embodiments, the uses described herein are for treating a human.

In another aspect, the present invention relates to antibodies for use in the detection of neurofibrillary tangles, neuropil threads and/or dystrophic neuritis. In some embodiments, an antibody described herein (any of the antibodies described herein) is for use in the detection of a Tau protein associated disease or disorder, tauopathy, AD, or FTD. In a specific embodiment, an antibody described herein (any of the antibodies described herein) is for use in the detection of AD.

BRIEF DESCRIPTION OF THE FIGURES

FIG. 1 (A-C) shows an alignment of the amino acid sequences of the light chain variable regions, including the CDRs, of the 5202.4 antibody and anti-pTau affinity matured variants of 5202.4, i.e., TAM1 to TAM23. Antibody 5202.4 has the same heavy and light chain variable region as the hACI-36-2B6-Ab1 antibody described in PCT/US13/32341, filed Mar. 15, 2013. The residue numbering is according to the Kabat system. The amino acid sequences of the CDRs are indicated as "Kabat-CDR L1," "Kabat-CDR L2," and "Kabat-CDR L3." CDR residues of the anti-pTau affinity matured variants which vary from the sequence of 5202.4 are highlighted (see residues in black boxes).

FIG. 2 shows binding of IgG1 5202.4, TAM1, TAM2, TAM9, TAM19, TAM20 and control (5B6 anti-gD) antibodies to non-phosphorylated full-length Tau, PKA-phosphorylated full-length Tau, hyperphosphorylated full-length Tau, monophosphorylated (pS129) alpha Synuclein or uncoated/BSA control.

FIG. 3 shows binding of immobilized IgG1 5202.4, TAM1, TAM2, TAM9, TAM19, TAM20 and control (5B6 anti-gD and no IgG) antibodies to Tau-derived biotinylated peptides including peptides phosphorylated on both Serine 404 and Serine 409 (pS404, pS409), peptides phosphorylated on Serine 404 (pS404), peptides phosphorylated on Serine 409 (pS409), non-phosphorylated peptides or no-peptide control. 10 nM of the biotinylated peptides shown in FIG. 3, and 5 µg/ml IgG, were used.

FIG. 4 shows binding of immobilized IgG1 5202.4, TAM1, TAM2, TAM9, TAM19, TAM20 and control (5B6 anti-gD and no IgG) antibodies to Tau-derived biotinylated peptides including peptides phosphorylated on both Serine 404 and Serine 409 (pS404, pS409), peptides phosphorylated on Serine 404 (pS404), peptides phosphorylated on Serine 409 (pS409), non-phosphorylated peptides, no-peptide control or background control. 20 nM of biotinylated peptides and 5 different concentrations of IgG (i.e., 0.01 nM, 0.1 nM, 1 nM, 10 nM and 100 nM IgG) were used for each binding experiment.

DETAILED DESCRIPTION OF EMBODIMENTS OF THE INVENTION

I. Definitions

Figures 2A, 2B:
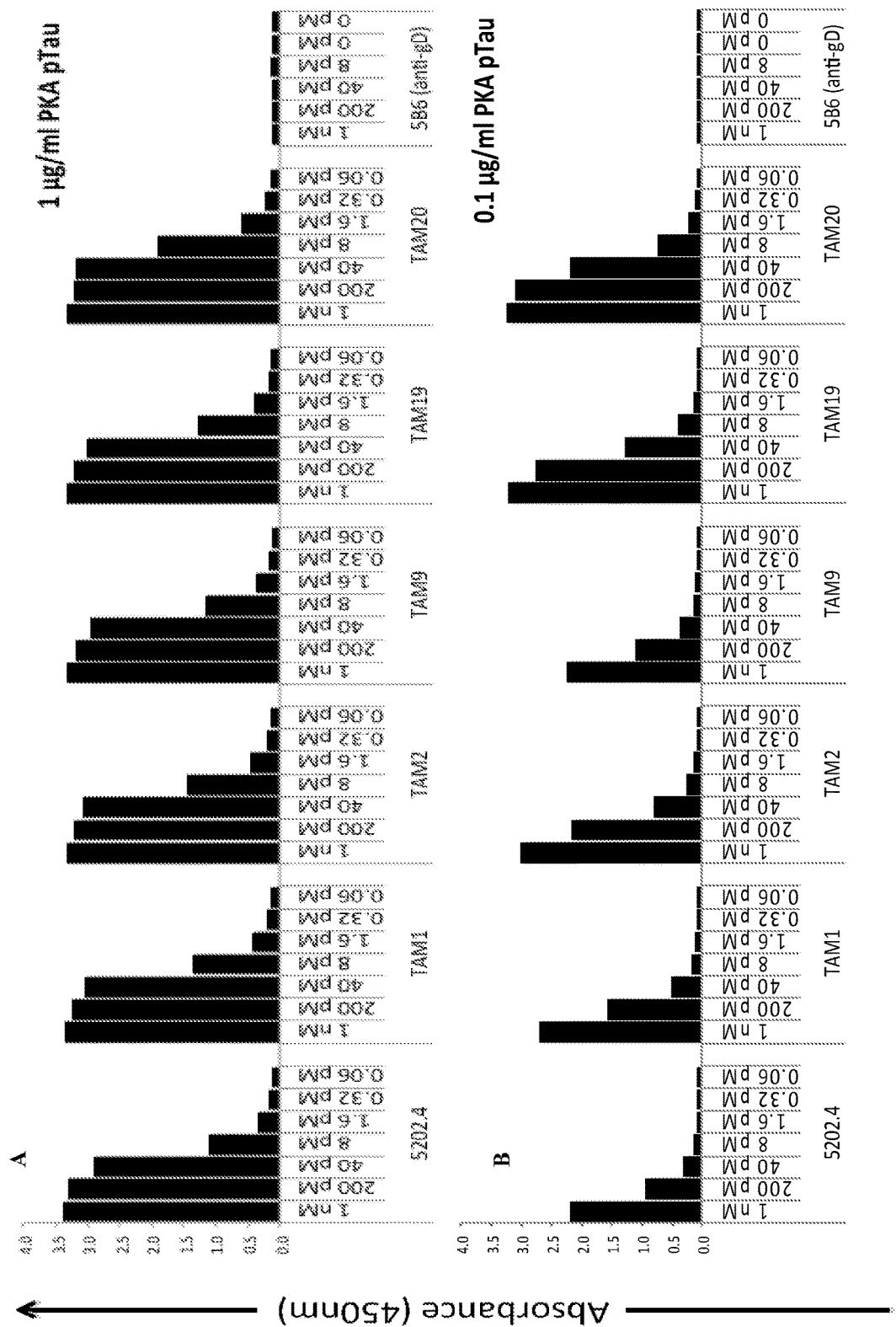
FIG. 2 (A-F). Binding of IgG antibodies to Tau, phosphorylated Tau and pS129 alpha Synuclein as measured by ELISA.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Tau antibody" and "an antibody that binds to Tau" refer to an antibody that is capable of binding Tau with sufficient affinity such that the antibody is useful as a diagnostic and/or therapeutic agent in targeting Tau. In one embodiment, the extent of binding of an anti-Tau antibody to an unrelated, non-Tau protein is less than about 10% of the binding of the antibody to Tau as measured, e.g., by a radioimmunoassay (RIA). In certain embodiments, an antibody that binds to Tau has a dissociation constant (Kd) of ≤1M, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-Tau antibody binds to an epitope of Tau that is conserved among Tau from different species. The term "anti-Tau antibody(ies)" encompasses anti-pTau antibody(ies).

The terms "anti-pTau antibody" and "an antibody that binds to pTau" refer to an antibody that is capable of binding phosphorylated epitopes of Tau with sufficient affinity such that the antibody is useful as a diagnostic and/or therapeutic agent in targeting pTau. In one embodiment, the extent of binding of an anti-pTau antibody to a non-pTau protein is less than about 10% of the binding of the antibody to pTau as measured, e.g., by a radioimmunoassay (RIA). In certain embodiments, an antibody that binds to pTau has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-pTau antibody binds to a phosphorylated epitope of Tau that is conserved among Tau from different species. In certain embodiments, the anti-pTau antibody binds selectively to a Tau phosphoform or epitope of Tau which contains amino acid residues which are phosphorylated. In other embodiments, the anti-pTau antibody does not bind, or binds with substantially reduced affinity, a non-phosphorylated Tau or epitope of Tau which is not phosphorylated relative to a phosphorylated Tau, Tau phosphoform or epitope of Tau which contains amino acids residues which are phosphorylated. In some embodiments, the phosphorylated Tau or epitope of Tau contains phosphorylated serines at amino acid position 404, 409 or 404 and 409 of the human Tau amino acid sequence.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "modulating antibody" refers to an antibody or a functional fragment thereof as described herein in the various embodiments, which may either up-regulate (e.g., activate or stimulate), down-regulate (e.g., inhibit or suppress) or otherwise change a functional property, biological activity or level of soluble and/or insoluble Tau protein, particularly of soluble phosphorylated Tau protein, in the brain, particularly in the brain cortex and/or hippocampus, of an animal, particularly a mammal or a human containing increased levels of soluble Tau protein and/or soluble phosphorylated tau protein. A modulating antibody or functional fragment thereof may act to modulate a Tau protein or a polypeptide encoding said Tau protein either directly or indirectly. In certain embodiments, a modulating antibody or functional fragment thereof reduces the levels of soluble and insoluble Tau protein, particularly of soluble phosphorylated Tau protein, in the brain, particularly in the brain cortex and/or hippocampus, of an animal, particularly a mammal or a human containing increased levels of soluble Tau protein and/or soluble phosphorylated Tau protein."

The phrases "substantially reduced" or "substantially different", as used herein, denote a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following. In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen can be measured, in one example, by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value can be measured by using surface plasmon resonance assays using a BIAcore™-2000 or a BIAcore™-3000 (BIAcore, Inc., Piscataway, N.J.) according to manufacturer's instructions or at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein.

Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) can be calculated using a simple one-to-one Langmuir binding model (BIAcore Evaluation Software version 3.2) by simultaneously fitting the association and dissociation sensorgrams. The equilibrium dissociation constant (Kd) can be calculated as the ratio $k_{off}/k_{on}$ See, e.g., Chen, Y., et al., (1999) J. Mol Biol 293:865-881. If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) can be calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$ See, e.g., Chen, Y., et al., (1999) J. Mol Biol 293:865-881. However, if the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified in Table 2B (i.e., comprise SEQ ID NO:33, SEQ ID NO:34, and/or SEQ ID NO:35) or elsewhere in the specification.

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Tau antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "pTau," as used herein, refers to Tau in which a serine, a threonine or a tyrosine residue is phosphorylated by a protein kinase by the addition of a covalently bound phosphate group. In some embodiments, pTau is phosphorylated on a serine or on a threonine residue. In some embodiments, pTau is phosphorylated on Serine at position 409 and/or Serine at position 404. In one embodiment, pTau is phosphorylated on Serine at position 409.

The term "Tau," as used herein, refers to any native Tau protein from any vertebrate source, including mammals such as primates (e.g., humans) and rodents (e.g., mice and rats), unless otherwise indicated. The term encompasses "full-length," unprocessed Tau as well as any form of Tau that results from processing in the cell. The term also encompasses naturally occurring variants of Tau, e.g., splice variants or allelic variants. The amino acid sequence of an exemplary human Tau is shown in SEQ ID NO:59.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007)) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "soluble Tau" or "soluble Tau protein," as used herein, refer to proteins consisting of both completely solubilized Tau protein/peptide monomers or of Tau-like peptides/proteins, or of modified or truncated Tau peptides/proteins or of other derivates of Tau peptides/proteins monomers, and of Tau protein oligomers. "Soluble Tau" excludes particularly neurofibrillary tangles (NFT).

The term "insoluble Tau," as used herein, refers to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble in the mammalian or human body more particularly in the brain, respectively. "Insoluble Tau" particularly includes neurofibrillary tangles (NFT).

The terms "monomeric Tau" or "Tau monomer," as used herein, refer to completely solubilized Tau proteins without aggregated complexes in aqueous medium.

The terms "aggregated Tau", "oligomeric Tau" and "Tau oligomer," as used herein, refer to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble or soluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble or soluble in the mammalian or human body more particularly in the brain, respectively.

The terms "pTau PHF", "PHF", and "paired helical filaments," are used herein synonymously, refer to pairs of filaments wound into helices with a periodicity of 160 nm visible on electron microscopy. Width varies between 10 and 22 nm. PHF are the predominant structures in neurofibrillary tangles of Alzheimer's Disease (AD) and neuropil threads. PHF may also be seen in some but not all dystrophic neurites associated with neuritic plaques. The major component of PHF is a hyperphosphorylated form of microtubule-associated protein tau. PHF may be partially composed of disulfide-linked antiparallel hyper-phosphorylated Tau proteins. PHF Tau may be truncated of its C-terminal 20 amino acid residues. The mechanisms underlying PHF formation are uncertain but hyper-phosphorylation of Tau may disengage it from microtubules, increasing the soluble pool of Tau from which PHF can be formed inside neurons.

II. Compositions and Methods

In one aspect, the invention is based, in part, on the generation of anti-Tau antibodies. In certain embodiments, antibodies that bind to pTau are provided. In certain embodiments, antibodies that bind to pTau with high specificity and/or high affinity are provided. In certain embodiments, antibodies that bind to Tau phosphorylated on Serine at position 409, such as antibodies that bind to Tau phosphorylated on Serine at position 409 with high affinity and/or high specificity, are provided. Antibodies of the invention are useful, e.g., for the diagnosis or treatment of tauopathies, such as Alzheimer's Disease (AD).

A. Exemplary Anti-Tau Antibodies

In one aspect, the invention provides isolated antibodies that bind to Tau or a fragment thereof. In certain embodiments, the invention provides an anti-pTau antibody that binds to a phosphorylated epitope on Tau (pTau). In some embodiments, the invention provides an anti-pTau antibody that binds to phosphorylated Serine at position 409 ("pS409") and/or phosphorylated Serine at position 404 ("pS404"). In one embodiment, the invention provides an anti-pTau antibody that binds to pS409. In specific embodiments, the invention provides an anti-pTau antibody that binds to an epitope which comprises amino acid residues 404-411 of the human Tau protein as shown in SEQ ID NO:59 (optionally, with the requirement of phosphorylated Serine at position 409, i.e., pS409). In other specific embodiments, the invention provides an anti-pTau antibody that binds to an epitope which comprises amino acid residues 405-411 of the human Tau protein as shown in SEQ ID NO:59 (optionally, with the requirement of pS409). In other specific embodiments, the invention provides an anti-pTau antibody that binds to an epitope which comprises amino acid residues 401-418 of the human Tau protein as shown in SEQ ID NO:59 (optionally, with the requirement of pS409). In particular embodiments, the invention provides an anti-Tau antibody that binds to a pathological phosphorylated epitope on Tau (e.g., a phosphorylated epitope associated with a tauopathy such as AD). In specific embodiments, the invention provides an anti-Tau antibody that binds to a pathological Tau conformer (e.g., a Tau conformer associated with a tauopathy such as AD). In one embodiment, the invention provides an anti-Tau antibody that binds to a hyperphosphorylated Tau (e.g., a hyperphosphorylated Tau associated with a tauopathy such as AD). In particular embodiments, the invention provides an anti-Tau antibody that binds to an aggregated Tau (e.g., an aggregated Tau associated with a tauopathy such as AD). In one embodiment, the invention provides an anti-Tau antibody that binds to an aggregated phosphorylated Tau (e.g., an aggregated Tau protein phosphorylated on an epitope associated with a tauopathy such as AD). In some embodiments, the invention provides an anti-Tau antibody that binds to soluble Tau (e.g., soluble pTau). In other embodiments, the invention provides an anti-Tau antibody that binds to insoluble Tau (e.g., insoluble pTau). In specific embodiments, the invention provides an anti-Tau antibody that binds to a microtubule-associated Tau (e.g., a microtubule-associated Tau associated with a tauopathy such as AD). In one embodiment, the invention provides an anti-Tau antibody that binds to an aggregated microtubule-associated Tau (e.g., an aggregated microtubule-associated Tau associated with a tauopathy such as AD). In one embodiment, the invention provides an anti-Tau antibody that binds to an aggregated and hyperphosphorylated microtubule-associated Tau (e.g., an aggregated and hyperphosphorylated microtubule-associated Tau associated with a tauopathy such as AD). In one embodiment, the invention provides an anti-Tau antibody that binds to Tau present in paired helical filaments (e.g., paired helical filaments associated with a tauopathy such as AD).). In particular embodiments, the invention provides an anti-Tau antibody that binds to Tau present in paired neurofibrillary tangles, neuropil threads and/or dystrophic neuritis (e.g., pTau or hyperphosphorylated Tau).

In some aspects, the invention provides an anti-Tau antibody that specifically recognizes and binds to Tau (e.g., pTau) or a fragment thereof. In certain embodiments, the invention provides an anti-pTau antibody that recognizes pTau with high specificity.

In certain embodiments, the invention provides an anti-pTau antibody that binds to a phosphorylated epitope on Tau (e.g., phosphoserine 409, phosphoserine 404, or phosphoserine 409 and phosphoserine 404) but does not bind to the corresponding unphosphorylated epitope on Tau and/or to non-related epitopes. In certain embodiments, the invention provides an anti-pTau antibody that binds to a phosphorylated epitope on Tau (e.g., phosphoserine 409, phosphoserine 404, or phosphoserine 409 and phosphoserine 404), but binds to the same epitope of Tau which is not phosphorylated with a substantially reduced affinity. In specific embodiments, the invention provides an anti-pTau antibody that binds to a phosphorylated epitope on Tau (e.g., phosphoserine 409, phosphoserine 404, or phosphoserine 409 and phosphoserine 404) with an affinity that is at least 3 times, at least 5 times, at least 10 times, at least 15 times, at least 20, at least 50 times, or at least 100 times greater than its affinity to the corresponding unphosphorylated epitope on Tau and/or to a non-related epitope. In specific embodiments, the invention provides an anti-pTau antibody that binds to a phosphorylated epitope on Tau (e.g., phosphoserine 409, phosphoserine 404, or phosphoserine 409 and phosphoserine 404) with an affinity that is at least 10 times greater than its affinity to the corresponding unphosphorylated epitope on Tau and/or to a non-related epitope.

In certain embodiments, the invention provides an anti-Tau (e.g., anti-pTau) antibody that has high affinity for Tau (e.g., pTau).

In particular embodiments, the invention provides an anti-pTau antibody that binds to a phosphorylated epitope on Tau (e.g., phosphoserine 409 and/or phosphoserine 404) with a dissociation constant (Kd) of less than 70 nM, less than 60 nM, less than 50 nM, less than 45 nM, less than 40 nM, less than 35 nM, less than 30 nM, less than 25 nM, less than 20 nM, less than 15 nM, less than 10 nM, less than 9 nM, less than 8 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, less than 0.6 nM, less than 0.5 nM, less than 0.4 nM, less than 0.3 nM, less than 0.2 nM or less than 0.1 nM (or equal to any of the above-listed values).

In some embodiments, the invention provides an anti-pTau antibody that binds to pTau with an association rate constant that is greater than $1.5 \times 10^5$ $M^{-1}$ $s^{-1}$, greater than $2 \times 10^5$ $M^{-1}$ $s^{-1}$, greater than $2.5 \times 10^5$ $M^{-1}$ $s^{-1}$, greater than $3 \times 10^5$ $M^{-1}$ $s^{-1}$, greater than $3.5 \times 10^5$ $M^{-1}$ $s^{-1}$, greater than $4 \times 10^5$ $M^{-1}$ $s^{-1}$, greater than $4.5 \times 10^5$ $M^{-1}$ $s^{-1}$, greater than $5 \times 10^5$ $M^{-1}$ $s^{-1}$, greater than $5 \times 10^5$ $M^{-1}$ $s^{-1}$, greater than $5.5 \times 10^5$ $M^{-1}$ $s^{-1}$, greater than $6 \times 10^5$ $M^{-1}$ $s^{-1}$, greater than $6.5 \times 10^5$ $M^{-1}$ $s^{-1}$, greater than $7 \times 10^5$ $M^{-1}$ $s^{-1}$, greater than $7.5 \times 10^5$ $M^{-1}$ $s^{-1}$, greater than $8 \times 10^5$ $M^{-1}$ $s^{-1}$, greater than $8.5 \times 10^5$ $M^{-1}$ $s^{-1}$, greater than $9 \times 10^5$ $s^{-1}$, greater than $10 \times 10^5$ $M^{-1}$ $s^{-1}$, greater than $12.5 \times 10^5$ $M^{-1}$, greater than $15 \times 10^5$ $M^{-1}$ $s^{-1}$, greater than $20 \times 10^5$ $M^{-1}$ $s^{-1}$, greater than $25 \times 10^5$ $M^{-1}$ $s^{-1}$, greater than $30 \times 10^5$ $M^{-1}$ $s^{-1}$, greater than $35 \times 10^5$ $M^{-1}$ $s^{-1}$, greater than $40 \times 10^5$ $M^{-1}$ $s^{-1}$, greater than $45 \times 10^5$ $M^{-1}$ $s^{-1}$, greater than $50 \times 10^5$ $M^{-1}$ $s^{-1}$, or greater than $75 \times 10^5$ $M^{-1}$ $s^{-1}$, or greater than $100 \times 10^5$ $M^{-1}$ $s^{-1}$ (or equal to any of the above-listed values).

In some embodiments, the invention provides an anti-pTau antibody that binds to pTau with a dissociation rate constant that is less than $10 \times 10^{-3}$ $s^{-1}$, less than $9 \times 10^{-3}$ $s^{-1}$, less than $8 \times 10^{-3}$ $s^{-1}$, less than $7 \times 10^{-3}$ $s^{-1}$, less than $6 \times 10^{-3}$ $s^{-1}$, less than $5 \times 10^{-3}$ $s^{-1}$, less than $4 \times 10^{-3}$ $s^{-1}$, less than $3 \times 10^{-3}$ $s^{-1}$, less than $2 \times 10^{-3}$ $s^{-1}$, less than $1 \times 10^{-3}$ $s^{-1}$, or less than $0.5 \times 10^{-3}$ $s^{-1}$, (or equal to any of the above-listed values). In yet other embodiments, the invention provides an anti-pTau antibody that binds to pTau with a dissociation rate constant that is greater than $1 \times 10^{-4}$ $s^{-1}$, greater than $2 \times 10^{-4}$ $s^{-1}$, greater than $3 \times 10^{-4}$ $s^{-1}$, greater than $4 \times 10^{-4}$ $s^{-1}$, greater than $5 \times 10^{-4}$ $s^{-1}$, greater than $6 \times 10^{-4}$ $s^{-1}$, greater than $7 \times 10^{-4}$ $s^{-1}$, greater than $8 \times 10^{-4}$ $s^{-1}$, greater than $9 \times 10^{-4}$ $s^{-1}$, less than $10 \times 10^{-4}$ $s^{-1}$, or greater than $12 \times 10^{-4}$ $s^{-1}$, (or equal to any of the above-listed values).

In some embodiments, the invention provides an anti-Tau antibody that has high specificity and/or high affinity for a pathological phosphorylated epitope(s) on Tau, a pathological Tau conformer (e.g., a pathological pTau), a hyperphosphorylated Tau, an aggregated Tau (e.g., an aggregated pTau), a soluble Tau (e.g., a soluble pTau), an insoluble Tau (e.g., an insoluble pTau), a microtubule-associated Tau (e.g., a microtubule-associated pTau), an aggregated and hyperphosphorylated microtubule-associated Tau, Tau present in paired helical filaments, or Tau present in paired neurofibrillary tangles, neuropil threads and/or dystrophic neuritis. In some embodiments, the invention provides an anti-Tau antibody that binds with a Kd, an association rate constant or a dissociation rate constant equal to any of the values provided above to a pathological phosphorylated epitope(s) on Tau, a pathological Tau conformer (e.g., a pathological pTau), a hyperphosphorylated Tau, an aggregated Tau (e.g., an aggregated pTau), a soluble Tau (e.g., a soluble pTau), an insoluble Tau (e.g., an insoluble pTau), a microtubule-associated Tau (e.g., a microtubule-associated pTau), an aggregated and hyperphosphorylated microtubule-associated Tau, Tau present in paired helical filaments, or Tau present in paired neurofibrillary tangles, neuropil threads and/or dystrophic neuritis. In some of these embodiments, the anti-Tau antibody binds to a phosphorylated epitope on Tau but does not bind (or binds with an affinity that is 5, 10, 50 or 100 times lower) to the corresponding unphosphorylated epitope on Tau and/or to non-related epitopes.

In some embodiments, the invention provides an anti-pTau antibody that has high specificity and/or high affinity for an epitope which comprises amino acid residues 404-411, 405-411 or 401-418, and includes pS409 and/or pS404, of the human Tau protein. In some embodiments, the invention provides an anti-pTau antibody that binds with a Kd, an association rate constant or a dissociation rate constant equal to any of the values provided above to an epitope which comprises amino acid residues 404-411, 405-411 or 401-418, and includes pS409, of the human Tau protein. In some of these embodiments, the anti-pTau antibody binds to the epitope which comprises amino acid residues 404-411, 405-411 or 401-418, and includes pS409, on Tau but does not bind (or binds with an affinity that is 5, 10, 50 or 100 times lower) to the corresponding unphosphorylated epitope on Tau and/or to non-related epitopes.

In certain embodiments, the invention provides an anti-Tau antibody that binds to a mammalian Tau (e.g., mammalian pTau), such as human Tau (e.g., human pTau).

In certain embodiments, the invention provides an anti-Tau (e.g., anti-pTau) antibody that is a monoclonal antibody or a fragment thereof. In one embodiment, the invention provides an anti-Tau (e.g., anti-pTau) antibody that is a chimeric antibody or a fragment thereof. In one embodiment, the invention provides an anti-Tau (e.g., anti-pTau) antibody that is a humanized antibody or a fragment thereof. In one embodiment, the invention provides an anti-Tau (e.g., anti-pTau) antibody that is a human antibody or a fragment thereof.

In one aspect, the invention provides an anti-Tau antibody comprising at least one, two, three, four, five, or six HVRs selected from (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14; (e) HVR-L2 comprising the amino acid sequence of SEQ ID NO:16, SEQ ID NO:17 SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26; and (f) HVR-L3 comprising the amino acid sequence of SEQ ID NO:27, SEQ ID NO:28, SEQ ID NO:29, SEQ ID NO:30, SEQ ID NO:31, or SEQ ID NO:32.

In one aspect, the invention provides an antibody comprising at least one, at least two, or all three VH HVR sequences selected from (a) HVR-H1 comprising the amino acid sequence of SEQ ID NO:33; (b) HVR-H2 comprising the amino acid sequence of SEQ ID NO:34; and (c) HVR-H3 comprising the amino acid sequence of SEQ ID NO:35. In one embodiment, the antibody comprises HVR-H3 comprising the amino acid sequence of SEQ ID NO:35. In another embodiment, the antibody comprises HVR-H3 comprising the amino acid sequence of SEQ ID NO:35 and HVR-L3 comprising the amino acid sequence of SEQ ID NO:27, SEQ ID NO:28, SEQ ID NO:29, SEQ ID NO:30, SEQ ID NO:31, or SEQ ID NO:32. In a further embodiment, the antibody comprises HVR-H3 comprising the amino acid sequence of SEQ ID NO:35, HVR-L3 comprising the amino acid sequence of SEQ ID NO:27, SEQ ID NO:28, SEQ ID NO:29, SEQ ID NO:30, SEQ ID NO:31, or SEQ ID NO:32, and HVR-H2 comprising the amino acid sequence of SEQ ID NO:34. In a further embodiment, the antibody comprises (a) HVR-H1 comprising the amino acid sequence of SEQ ID NO:33; (b) HVR-H2 comprising the amino acid sequence of SEQ ID NO:34; and (c) HVR-H3 comprising the amino acid sequence of SEQ ID NO:35.

In another aspect, the invention provides an antibody comprising at least one, at least two, or all three VL HVR sequences selected from (a) HVR-L1 comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO:12, SEQ ID NO:13, or SEQ ID NO:14; (b) HVR-L2 comprising the amino acid sequence of SEQ ID NO:16, SEQ ID NO:17 SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26; and (c) HVR-L3 comprising the amino acid sequence of SEQ ID NO:27, SEQ ID NO:28, SEQ ID NO:29, SEQ ID NO:30, SEQ ID NO:31, or SEQ ID NO:32. In one embodiment, the antibody comprises (a) HVR-L1 comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14; (b) HVR-L2 comprising the amino acid sequence of SEQ ID NO:16, SEQ ID NO:17 SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26; and (c) HVR-L3 comprising the amino acid sequence of SEQ ID NO:27, SEQ ID NO:28, SEQ ID NO:29, SEQ ID NO:30, SEQ ID NO:31, or SEQ ID NO:32.

In another aspect, an antibody of the invention comprises (a) a VH domain comprising at least one, at least two, or all three VH HVR sequences selected from (i) HVR-H1 comprising the amino acid sequence of SEQ ID NO:33, (ii) HVR-H2 comprising the amino acid sequence of SEQ ID NO:34, and (iii) HVR-H3 comprising an amino acid sequence selected from SEQ ID NO:35; and (b) a VL domain comprising at least one, at least two, or all three VL HVR sequences selected from (i) HVR-L1 comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, (ii) HVR-L2 comprising the amino acid sequence of SEQ ID NO:16, SEQ ID NO:17 SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26, and (c) HVR-L3 comprising the amino acid sequence of SEQ ID NO:27, SEQ ID NO:28, SEQ ID NO:29, SEQ ID NO:30, SEQ ID NO:31, or SEQ ID NO:32.

In another aspect, the invention provides an antibody comprising (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14; (e) HVR-L2 comprising the amino acid sequence of SEQ ID NO:16, SEQ ID NO:17 SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26; and (f) HVR-L3 comprising an amino acid sequence selected from SEQ ID NO:27, SEQ ID NO:28, SEQ ID NO:29, SEQ ID NO:30, SEQ ID NO:31, or SEQ ID NO:32.

In certain embodiments, any one or more amino acids of an anti-Tau antibody comprising HVR-L1 of SEQ ID NO:15, HVR-L2 of SEQ ID NO:16 and HVR-L3 of SEQ ID NO:30 are substituted at the following HVR positions (as defined by Kabat):
  in HVR-L1 (SEQ ID NO:15): Kabat positions 24, 27A, 27C, 27D, 27E, 28, 30 and 33
  in HVR-L2 (SEQ ID NO:16): Kabat positions 52, 53, and 56
  in HVR-L3 (SEQ ID NO:30): Kabat positions 92, 93, and 96

In certain embodiments, the substitutions are conservative substitutions, as provided herein. In certain embodiments, any one or more of the following substitutions may be made in any combination at the indicated Kabat positions:
  in HVR-L1 (SEQ ID NO:15): R24T; S27$^a$R or V; V27$^c$R or I; H27$^d$R; S27$^e$R, G or K; H28R, K, N or G; K30R; or L33V
  in HVR-L2 (SEQ ID NO:16): S52K or R; N53K or H; or S56F, G, K, R, Y, or L
  in HVR-L3 (SEQ ID NO:30): A92R, H93R, Q or Y; or Y96R.

All possible combinations of the above substitutions are encompassed by the following consensus sequences:
  HVR-L1 comprising the amino acid sequence $X_1$SSQ$X_2$L$X_3X_4X_5X_6$G$X_7$TY$X_8$H (SEQ ID NO:89), wherein $X_1$=R or T; $X_2$=S, R or V; $X_3$=V, I or R; $X_4$=H or R; $X_5$=S, R, G or K; N, R, K or G; $X_7$=K or R; and $X_8$=I, or V;
  HVR-L2 comprising the amino acid sequence KV$X_9X_{10}$RF$X_{11}$(SEQ ID NO:90), wherein $X_9$=S, K or R; K or H; and $X_{11}$=S, F, G, K, R, Y or L,
  HVR-L3 comprises the amino acid sequence SQT$X_{12}X_{13}$FP$X_{14}$T (SEQ ID NO:91), wherein $X_{12}$=A or R; $X_{13}$=H, R, Q or Y; $X_{14}$=Y or R.

In specific embodiments, the antibody having the consensus sequence presented above does not comprise all three of the following HVR-L1. HVR-L2 and HVR-L3 sequences: HVR-L1 consisting of RSSQSLVHSHGKTYLH (SEQ ID NO:15) or RSSQRLVHSHGKTYLH (SEQ ID NO:92); HVR-L2 consisting of KVSNRFS (SEQ ID NO:16); and HVR-L3 consisting of SQTAHFPYT (SEQ ID NO:30).

In a particular embodiment, the invention provides an antibody comprising (a) HVR-L1 comprising the amino acid sequence of SEQ ID NO:1; (b) HVR-L2 comprising the amino acid sequence of SEQ ID NO:16; and (c) HVR-L3 comprising an amino acid sequence of SEQ ID NO:27. In one embodiment, the invention provides an antibody comprising (a) HVR-L1 comprising the amino acid sequence of SEQ ID NO:2; (b) HVR-L2 comprising the amino acid sequence of SEQ ID NO:17; and (c) HVR-L3 comprising an amino acid sequence of SEQ ID NO:27. In one embodiment, the invention provides an antibody comprising (a) HVR-L1 comprising the amino acid sequence of SEQ ID NO:8; (b) HVR-L2 comprising the amino acid sequence of SEQ ID NO:21; and (c) HVR-L3 comprising an amino acid sequence of SEQ ID NO:29. In one embodiment, the invention provides an antibody comprising (a) HVR-L1 comprising the amino acid sequence of SEQ ID NO:14; (b) HVR-L2 comprising the amino acid sequence of SEQ ID NO:25; and (c) HVR-L3 comprising an amino acid sequence of SEQ ID NO:31. In one embodiment, the invention provides an antibody comprising (a) HVR-L1 comprising the amino acid sequence of SEQ ID NO:9; (b) HVR-L2 comprising the amino acid sequence of SEQ ID NO:17; and (c) HVR-L3 comprising an amino acid sequence of SEQ ID NO:31.

In a specific embodiment, the invention provides an antibody comprising (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:1; (e) HVR-L2 comprising the amino acid sequence of SEQ ID NO:16; and (f) HVR-L3 comprising an amino acid sequence of SEQ ID NO:27. In another specific embodiment, the invention provides an antibody comprising (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:2; (e) HVR-L2 comprising the amino acid sequence of SEQ ID NO:17; and (f) HVR-L3 comprising an amino acid sequence of SEQ ID NO:27. In another specific embodiment, the invention provides an antibody comprising (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:8; (e) HVR-L2 comprising the amino acid sequence of SEQ ID NO:21; and (f) HVR-L3 comprising an amino acid sequence of SEQ ID NO:29. In yet another specific embodiment, the invention provides an antibody comprising (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:14; (e) HVR-L2 comprising the amino acid sequence of SEQ ID NO:25; and (f) HVR-L3 comprising an amino acid sequence of SEQ ID NO:31. In still another specific embodiment, the invention provides an antibody comprising (a) HVR-H1 comprising the amino acid sequence of SEQ ID NO:33; (b) HVR-H2 comprising the amino acid sequence of SEQ ID NO:34; (c) HVR-H3 comprising the amino acid sequence of SEQ ID NO:35; (d) HVR-L1 comprising the amino acid sequence of SEQ ID NO:9; (e) HVR-L2 comprising the amino acid sequence of SEQ ID NO:17; and (f) HVR-L3 comprising an amino acid sequence of SEQ ID NO:31.

In any of the above embodiments, an anti-Tau antibody can be humanized. In one embodiment, an anti-Tau antibody comprises HVRs as in any of the above embodiments, and further comprises an acceptor human framework, e.g. a human immunoglobulin framework or a human consensus framework. In another embodiment, an anti-Tau antibody comprises HVRs as in any of the above embodiments, and further comprises a VH comprising the sequence of SEQ ID NO:58. In another embodiment, an anti-Tau antibody comprises HVRs as in any of the above embodiments, and further comprises a VL comprising sequence of SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, or SEQ ID NO:57.

In another aspect, an anti-Tau antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:58. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Tau antibody comprising that sequence retains the ability to bind to Tau. In certain embodiments, a total of 1 to 10 amino acids have been substituted, inserted and/or deleted in SEQ ID NO:58. In certain embodiments, substitutions, insertions, or deletions occur in regions outside the HVRs (i.e., in the FRs). Optionally, the anti-Tau antibody comprises the VH sequence in SEQ ID NO:58, including post-translational modifications of that sequence. In a particular embodiment, the VH comprises one, two or three HVRs selected from: (a) HVR-H1 comprising the amino acid sequence of SEQ ID NO:33, (b) HVR-H2 comprising the amino acid sequence of SEQ ID NO:34, and (c) HVR-H3 comprising the amino acid sequence of SEQ ID NO:35.

In another aspect, an anti-Tau antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, or SEQ ID NO:57. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Tau antibody comprising that sequence retains the ability to bind to Tau. In certain embodiments, a total of 1 to 10 amino acids have been substituted, inserted and/or deleted in SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, or SEQ ID NO:57. In certain embodiments, the substitutions, insertions, or deletions occur in regions outside the HVRs (i.e., in the FRs). Optionally, the anti-Tau antibody comprises the VL sequence in SEQ ID NO:36, including post-translational modifications of that sequence. In one embodiment, the anti-Tau antibody comprises the VL sequence in SEQ ID NO:37, including post-translational modifications of that sequence. In another embodiment, the anti-Tau antibody comprises the VL sequence in SEQ ID NO:44, including post-translational modifications of that sequence. In yet another embodiment, the anti-Tau antibody comprises the VL sequence in SEQ ID NO:54, including post-translational modifications of that sequence. In still another embodiment, the anti-Tau antibody comprises the VL sequence in SEQ ID NO:55, including post-translational modifications of that sequence. In a particular embodiment, the VL comprises one, two or three HVRs selected from (a) HVR-L1 comprising the amino acid sequence of SEQ ID NO:1, SEQ ID NO:2, SEQ ID NO:8, SEQ ID NO:9, or SEQ ID NO:14; (b) HVR-L2 comprising the amino acid sequence of SEQ ID NO:16, SEQ ID NO:17, SEQ ID NO:21, or SEQ ID NO:25; and (c) HVR-L3 comprising the amino acid sequence of SEQ ID NO:27, SEQ ID NO:29, or SEQ ID NO:31.

In another aspect, an anti-Tau antibody is provided, wherein the antibody comprises a VH as in any of the embodiments provided above, and a VL as in any of the embodiments provided above. In one embodiment, the antibody comprises the VH and VL sequences in SEQ ID NO:58 and SEQ ID NO:36, respectively, including post-translational modifications of those sequences. In one embodiment, the antibody comprises the VH and VL sequences in SEQ ID NO:58 and SEQ ID NO:37, respectively, including post-translational modifications of those sequences. In one embodiment, the antibody comprises the VH and VL sequences in SEQ ID NO:58 and SEQ ID NO:44, respectively, including post-translational modifications of those sequences. In one embodiment, the antibody comprises the VH and VL sequences in SEQ ID NO:58 and SEQ ID NO:54, respectively, including post-translational modifications of those sequences. In one embodiment, the antibody comprises the VH and VL sequences in SEQ ID NO:58 and SEQ ID NO:55, respectively, including post-translational modifications of those sequences.

In a further aspect, the invention provides an antibody that binds to the same epitope as an anti-Tau antibody provided herein. For example, in certain embodiments, an antibody is provided that binds to the same epitope as antibody comprising a VH sequence of SEQ ID NO:58 and a VL sequence selected from the group consisting of: SEQ ID NO:36, SEQ ID NO:37, SEQ ID NO:44, SEQ ID NO:54, and SEQ ID NO:55. In certain embodiments, an antibody is provided that binds to a phosphorylated epitope within a fragment of Tau consisting of amino acids 401-418, or consisting of amino acids 404-411, or consisting of amino acids 405-411, of SEQ ID NO:59.

In a further aspect of the invention, an anti-Tau antibody according to any of the above embodiments is a monoclonal antibody, including a chimeric, humanized or human antibody. In one embodiment, an anti-Tau antibody is an antibody fragment, e.g., a Fv, Fab, Fab', scFv, diabody, or F(ab')$_2$ fragment. In another embodiment, the antibody is a full length antibody, e.g., an intact IgG1, IgG1 N297G, IgG2, IgG3, or IgG4 antibody or other antibody class or isotype as defined herein.

In a further aspect, an anti-Tau antibody according to any of the above embodiments may incorporate any of the features, singly or in combination, as described in Sections 1-7 below:

1. Antibody Affinity

In certain embodiments, an antibody provided herein has a dissociation constant (Kd) of ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M. e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACOR®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region.

In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al. *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Tau (e.g., pTau) and the other is for any other antigen. In certain embodiments, bispecific antibodies may bind to two different epitopes of Tau (e.g., pTau). Bispecific antibodies may also be used to localize cytotoxic agents to cells which express Tau. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Tau (e.g., pTau) as well as another, different antigen (see, US 2008/0069820, for example).

Additionally, antibodies of the present invention may be engineered to take advantage of receptor mediated transport (RMT) across the blood brain barrier (BBB) by various exploiting BBB receptors (i.e., transferrin receptor, insulin receptor, low density lipoprotein receptor-related protein 8, glucose transporter 1 (Glut¹) and the like) (see, e.g., WO9502421). For example, the antibodies of the present invention can be made multispecific to target Tau and the BBB receptor. A non-limiting example of a multispecific antibody includes a bispecific antibody in which one arm of the antibody is an antibody fragment of the present invention and the other arm of the antibody targets a BBB receptor which mediates transport across the BBB. The BBB receptor for example can include transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut 1) and heparin-binding epidermal growth factor-like growth factor (HB-EGF).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially in Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Intl. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Tau (e.g., anti-pTau) antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Tau antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Tau antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu. *Methods in Molecular Biology, Vol.* 248 (B. K. C. Lo, ed., Humana Press, Totowa, N.J.), pp. 255-268 (2003).

C. Assays

Anti-Tau (e.g., anti-pTau) antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, Biacore, etc.

In another aspect, competition assays may be used to identify an antibody that competes with one or more antibodies described herein (e.g., antibody having light chain of SEQ ID NO:61 and heavy chain of SEQ ID NO:63, antibody having light chain of SEQ ID NO:64 and heavy chain of SEQ ID NO:87, antibody having light chain of SEQ ID NO:65 and heavy chain of SEQ ID NO:87, antibody having light chain of SEQ ID NO:72 and heavy chain of SEQ ID NO:87, antibody having light chain of SEQ ID NO:82 and heavy chain of SEQ ID NO:87, or antibody having light chain of SEQ ID NO:83 and heavy chain of SEQ ID NO:87, for binding to pTau. In certain embodiments, such a competing antibody binds to the same epitope (e.g., a linear or a conformational epitope) that is bound by such antibodies. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized pTau is incubated in a solution comprising a first labeled antibody that binds to pTau (e.g., antibody having the light chain of SEQ ID NO:61 and the heavy chain of SEQ ID NO:63, antibody having the light chain of SEQ ID NO:64 and the heavy chain of SEQ ID NO:87, antibody having the light chain of SEQ ID NO:65 and the heavy chain of SEQ ID NO:87, antibody having the light chain of SEQ ID NO:72 and heavy chain of SEQ ID NO:87, antibody having the light chain of SEQ ID NO:82 and the heavy chain of SEQ ID NO:87, or antibody having the light chain of SEQ ID NO:83 and the heavy chain of SEQ ID NO:87) and a second unlabeled antibody that is being tested for its ability to compete with the first antibody for binding to pTau. The second antibody may be present in a hybridoma supernatant. As a control, immobilized pTau is incubated in a solution comprising the first labeled antibody but not the second unlabeled antibody. After incubation under conditions permissive for binding of the first antibody to pTau, excess unbound antibody is removed, and the amount of label associated with immobilized pTau is measured. If the amount of label associated with immobilized pTau is substantially reduced in the test sample relative to the control sample, then that indicates that the second antibody is competing with the first antibody for binding to pTau. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-Tau (e.g., anti-pTau) antibodies thereof having biological activity. Biological activity may include, e.g., binding of such antibodies to Tau (e.g., neurofibrillary tangles in the brain containing Tau) and reducing the level of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau, in the brain, e.g., in the brain cortex and/or hippocampus). Antibodies having such biological activity in vivo and/or in vitro are also provided.

In certain embodiments, an antibody of the invention is tested for such biological activity. For example, an animal model of tauopathy, such as a Tau transgenic mice (e.g., P301L), can be used to detect binding of anti-Tau antibodies to brain sections, and in particular, to neurofibrillary tangles in the brains of the transgenic mice. Further, an animal model of tauopathy, such as a Tau transgenic mice (e.g., P301L), can be treated with anti-Tau antibodies (e.g., anti-pTau) and experimental techniques known in the art can be used to assess whether such treatment reduces the level of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in the mouse brain (e.g., in the brain cortex and/or hippocampus).

D. Immunoconjugates

The invention also provides immunoconjugates comprising an anti-Tau (e.g., anti-pTau) antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med.*

Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $I^{332}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any one of the anti-Tau antibodies provided herein is useful for detecting the presence of Tau in a biological sample. The term "detecting" as used herein encompasses quantitative or qualitative detection. In certain embodiments, a biological sample comprises a cell or tissue, such as cerebrospinal fluid, a cell or tissue of the brain (e.g., brain cortex or hippocampus), or blood. In one embodiment, a biological sample is cerebrospinal fluid.

In one embodiment, an anti-Tau (e.g., anti-pTau) antibody for use in a method of diagnosis or detection is provided. In a further aspect, a method of detecting the presence of Tau (e.g., pTau) in a biological sample is provided. In certain embodiments, the method comprises contacting the biological sample with an anti-Tau antibody as described herein under conditions permissive for binding of the anti-Tau antibody to Tau, and detecting whether a complex is faulted between the anti-Tau antibody and Tau. In certain embodiments, the method comprises contacting the biological sample with an anti-pTau antibody as described herein under conditions permissive for binding of the anti-pTau antibody to pTau, and detecting whether a complex is formed between the anti-pTau antibody and pTau. Such method may be an in vitro or in vivo method. Further, the complex formed between the anti-Tau antibody and Tau in a test biological sample can be compared to the complex formed in a control biological sample (e.g., a biological sample from a healthy subject or subjects). The amount of the complex formed between the anti-Tau antibody and Tau in a test biological sample can also be quantified and compared to the amount of the complex formed in a control biological sample (e.g., a biological sample from a healthy subject or subjects) or to the average amount of the complex known to be formed in healthy subjects.

In one embodiment, an anti-Tau antibody is used to select subjects eligible for therapy with an anti-Tau antibody, e.g. where Tau is a biomarker for selection of patients. In one embodiment, an anti-pTau antibody is used to select subjects eligible for therapy with an anti-pTau antibody, e.g. where pTau is a biomarker for selection of patients. For example, in some embodiments, an anti-Tau (e.g., anti-pTau) antibody is used to detect whether the subject has a Tau protein disease or disorder, or whether the subject is at high risk (or predisposed to) a Tau protein disease or disorder.

Exemplary diseases or disorders that may be diagnosed using an antibody of the invention include Tau protein associated diseases or disorders, and diseases or disorders caused by or associated with the formation of neurofibrillary tangles or neuropil threads. In some embodiments, diseases or disorders that may be diagnosed using an antibody of the invention include Tau protein associated diseases or disorders that are manifested in an impairment or loss of cognitive functions including reasoning, situational judgement, memory capacity, learning, and/or special navigation. In particular, diseases or disorders that may be diagnosed using an antibody of the invention include tauopathies such as neurodegenerative tauopathies. Exemplary diseases or disorders that may be diagnosed using an antibody of the invention include, but are not limited to, Alzheimer's Disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotetemporal dementia, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy. Subacute sclerosing panencephalitis, Tangle only dementia, Postencephalitic Parkinsonism, and Myotonic dystrophy. In one embodiment, a disorder that may be diagnosed using an antibody of the invention is Alzheimer's Disease (AD).

In certain embodiments, labeled anti-Tau antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-Tau (e.g., anti-pTau) antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation provided herein may also contain more than one active ingredients as necessary for the particular indication being treated, preferably those with complementary activities that do not adversely affect each other. Such active ingredients are suitably present in combination in amounts that are effective for the purpose intended.

The composition according to the invention may be administered in combination with other compositions comprising an biologically active substance or compound such as, for example, a known compound used in the medication of tauopathies and/or of amyloidoses, a group of diseases and disorders associated with amyloid or amyloid-like protein such as the amyloid 13 protein involved in Alzheimer's Disease.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the biologically active agent or compound may comprise at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, [beta]- and 7-secretase inhibitors, tau proteins, neurotransmitter, /3-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, *Ginkgo biloba*, acyetyl-L-carnitine, idebenone, propentofylline, or a xanthine derivative, together with a binding peptide according to the invention including antibodies, particularly monoclonal antibodies and active fragments thereof, and, optionally, a pharmaceutically acceptable carrier and/or a diluent and/or an excipient and instructions for the treatment of diseases.

In a further embodiment, the composition according to the invention may comprise niacin or memantine together with a chimeric antibody or a humanized antibody according to the invention including antibodies, particularly monoclonal antibodies and active fragments thereof, and, optionally, a pharmaceutically acceptable carrier and/or a diluent and/or an excipient.

In still another embodiment of the invention compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the chimeric antibody or the humanized antibody according to the invention or active fragments thereof, and, optionally, a pharmaceutically acceptable carrier and/or a diluent and/or an excipient.

Other compounds that can be suitably used in compositions in addition to chimeric antibody or humanized antibody according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-Tau (e.g., anti-pTau) antibodies provided herein may be used in therapeutic methods.

In one aspect, an anti-Tau antibody for use as a medicament is provided. In further aspects, an anti-Tau antibody for use in treating a Tau protein associated disease or disorder is provided. In some embodiments, an anti-Tau antibody for use in treating diseases or disorders caused by or associated with the formation of neurofibrillary tangles or neuropil threads is provided. In particular embodiments, an anti-Tau antibody for use in treating a tauopathy such as a neurodegenerative tauopathy is provided. Exemplary Tau protein associated diseases or disorders that can be treated that can be treated with anti-tau antibodies include, without limitation, Alzheimer's Disease, amyotrophic lateral sclerosis, Parkinson's disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotetemporal dementia, frontotemporal dementia with parkinsonism linked to chromosome 17, Hallevorden-Spatz disease, multiple system atrophy, Niemann-Pick disease, type C. Pallido-ponto-nigral degeneration, Pick's disease, progressive subcortical gliosis, progressive supranuclear palsy, Subacute sclerosing panencephalitis, Tangle only dementia, Postencephalitic Parkinsonism, and Myotonic dystrophy. In one embodiment, an anti-Tau antibody for use in treating Alzheimer's Disease (AD) is provided herein. Further, Tau protein associated diseases or disorders that can be treated with an anti-Tau antibody include diseases or disorders that are manifested in an impairment or loss of a cognitive function such as reasoning, situational judgement, memory capacity, learning, and/or special navigation. In certain embodiments, an anti-Tau antibody for use in a method of treatment is provided. In certain embodiments, the invention provides an anti-Tau antibody for use in a method of treating an individual, having any one of the Tau associated diseases or disorders described above, comprising administering to the individual an effective amount of the anti-Tau (e.g., anti-pTau) antibody. In one such embodiment, the method further comprises administering to the individual an effective amount of at least one additional therapeutic agent, e.g., as described below.

In further embodiments, the invention provides an anti-Tau antibody for use in reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in an individual. For example such reduction can occur in the brain (e.g., in the brain cortex and/or hippocampus). In one embodiment, the invention provides an anti-Tau antibody for use in reducing the levels of phosphorylated Tau. In one embodiment, the invention provides an anti-Tau antibody for use in reducing the levels of insoluble Tau (e.g., insoluble phosphorylated Tau). In one embodiment, the invention provides an anti-Tau antibody for use in reducing the levels of hyperphosphorylated Tau. In one embodiment, the invention provides an anti-Tau antibody for use in reducing the levels of paired helical filaments (e.g., paired helical filaments containing hyperphosphorylated Tau) in a brain tissue (e.g., in the brain cortex and/or hippocampus). In certain embodiments, the invention provides an anti-Tau (e.g., anti-pTau) antibody for use in a method of reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in the brain (e.g., in the brain cortex and/or hippocampus) in an individual comprising administering to the individual an effective amount of the anti-Tau antibody to reduce the levels of Tau protein. An "individual" according to any of the above embodiments is a mammal, preferably a human.

In some embodiments, the invention provides an anti-Tau antibody for use in modulating the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau), for example, in the brain (e.g., in the brain cortex and/or hippocampus) of an individual.

In a further aspect, the invention provides for the use of an anti-Tau antibody in the manufacture or preparation of a medicament. In one embodiment, the medicament is for treatment of a Tau protein associated disease or disorder. The Tau protein associated disease or disorder can be a disease or disorders caused by or associated with the formation of neurofibrillary tangles or neuropil threads. In particular embodiments, the medicament is for treatment of a tauopathy such as a neurodegenerative tauopathy. In specific embodiments, the medicament is for treatment of diseases or disorders selected from the group consisting of: Alzheimer's Disease (AD), Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis, Tangle only dementia, Postencephalitic Parkinsonism, and Myotonic dystrophy. In one embodiment, the medicament is for treatment of AD. In particular embodiments, the medicament is for treatment of a Tau associated disease or disorder that is manifested in an impairment or loss of a cognitive function such as reasoning, situational judgement, memory capacity, learning, or special navigation. In a further embodiment, the medicament is for use in a method of treating one of the above-listed diseases (e.g., a tauopathy such as AD) comprising administering to an individual having such disease an effective amount of the medicament. In one such embodiment, the method further comprises administering to the individual an effective amount of at least one additional therapeutic agent, e.g., as described below.

In a further embodiment, the medicament is for reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau). For example, such reducing of Tau protein can be observed in the brain (e.g., in the brain cortex and/or hippocampus) or in cerebrospinal fluid of an individual. In one embodiment, the medicament is for reducing the levels phosphorylated Tau. In one embodiment, the medicament is for reducing the levels of insoluble Tau (e.g., insoluble phosphorylated Tau). In one embodiment, the medicament is for reducing the levels of hyperphosphorylated Tau. In one embodiment, the medicament is for reducing the levels of paired helical filaments (e.g., paired helical filaments containing hyperphosphorylated Tau). In a further embodiment, the medicament is for use in a method of reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in an individual comprising administering to the individual an effective amount of the medicament to reducing the levels of Tau protein. An "individual" according to any of the above embodiments is a mammal, preferably, a human.

In a further aspect, the invention provides a method for treating a Tau protein associated disease or disorder. Tau protein associated disease or disorder that can be treated in accordance with the methods provided herein include diseases or disorders caused by or associated with the formation of neurofibrillary tangles or neuropil threads. In particular embodiments, the invention provides a method for treating a tauopathy such as a neurodegenerative tauopathy. In specific embodiments, the invention provides a method for treating a disease or disorder selected from the group consisting of: Alzheimer's Disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis, Tangle only dementia, Postencephalitic Parkinsonism, and Myotonic dystrophy. In one embodiment, the invention provides a method for treating Alzheimer's Disease (AD). In particular embodiments, the invention provides a method for treating a Tau protein associated disease or disorder that is manifested in an impairment or loss of a cognitive function such as reasoning, situational judgement, memory capacity, learning, or special navigation. In one embodiment, the method comprises administering to an individual, having any one of the diseases or disorders described above, an effective amount of an anti-Tau (e.g., anti-pTau) antibody. In one such embodiment, the method further comprises administering to the individual an effective amount of at least one additional therapeutic agent, e.g., as described below. In one embodiment, the method comprises administering to an individual having one of the diseases described herein an effective amount of an anti-Tau (e.g., anti-pTau) antibody. In one such embodiment, the method further comprises administering to the individual an effective amount of at least one additional therapeutic agent, as described below. An "individual" according to any of the above embodiments may be a human.

In a further aspect, the invention provides a method for reducing the levels of Tau protein (e.g., total Tau, total soluble Tau, soluble phosphorylated Tau, total insoluble Tau, insoluble phosphorylated Tau, hyperphosphorylated Tau, or paired helical filaments containing hyperphosphorylated Tau) in an individual. For example, such reducing of the levels of Tau protein can be observed in the brain (e.g., brain cortex and/or hippocampus) or cerebrospinal fluid of an individual. In one embodiment, the invention provides a method for reducing the levels phosphorylated Tau. In one embodiment, the invention provides a method for reducing levels of insoluble Tau (e.g., insoluble phosphorylated Tau). In one embodiment, the invention provides a method for reducing the levels of hyperphosphorylated Tau. In one embodiment, the invention provides a method for reducing the levels of paired helical filaments (e.g., paired helical filaments containing hyperphosphorylated Tau). In one embodiment, the method comprises administering to the individual an effective amount of an anti-Tau (e.g., anti-pTau) antibody to reduce the levels of Tau protein. In one embodiment, an "individual" is a human.

In some aspects, the invention provides a method for alleviating one or more symptoms of a Tau protein associated disease or disorder; or an anti-Tau antibody or a medicament comprising anti-Tau antibody for alleviating one or more symptoms of a Tau protein associated disease or disorder (such as any of the diseases or disorders described herein, for example, AD). In some aspects, the invention provides a method for reducing the number of symptoms or the severity of one or more symptoms of a Tau protein associated disease or disorder; or an anti-Tau antibody or a medicament comprising anti-Tau antibody for reducing the number of symptoms or the severity of one or more symptoms of a Tau protein associated disease or disorder (such as any of the diseases or disorders described herein, for example, AD). In a particular embodiment, the symptom of a Tau protein associated disease or disorder is an impairment in cognition. In a specific embodiment, the symptom of a Tau protein associated disease or disorder is an impairment in learning and/or memory. In a specific embodiment, the symptom of a Tau protein associated disease or disorder is a long-term memory loss. In a specific embodiment, the symptom of a Tau protein associated disease or disorder is dementia. In some embodiments, the symptom of a Tau protein associated disease or disorder is confusion, irritability, aggression, mood swings, or a language impairment. In some embodiments, the symptom of a Tau protein associated disease or disorder is an impairment or loss of one or more cognitive functions such as reasoning, situational judgment, memory capacity, and/or learning. The methods provided herein comprise administration of an amount (e.g., therapeutically effective amount) of an anti-Tau antibody to an individual (e.g., who displays one or more symptoms of a Tau protein associated disease or disorder).

In specific aspects, the invention provides a method for retaining or increasing cognitive memory capacity, or for slowing down memory loss associated with a Tau protein associated disease or disorder; or an anti-Tau antibody or a medicament comprising anti-Tau antibody for retaining or increasing cognitive memory capacity or for slowing down memory loss associated with a Tau protein associated disease or disorder (such as any of the diseases or disorders described herein, for example, AD). The methods provided herein comprise administration of an amount (e.g., therapeutically effective amount) of an anti-Tau antibody to an individual (e.g., who displays one or more symptoms of memory loss or a decrease of memory capacity).

In some aspects, the invention provides a method for decreasing the rate of progression of a Tau protein associated disease or disorder; or an anti-Tau antibody or a medicament comprising anti-Tau antibody for decreasing the rate of progression of a Tau protein associated disease or disorder (such as any of the diseases or disorders described herein, for example, AD). The methods provided herein comprise administration of an amount (e.g., therapeutically effective amount) of an anti-Tau antibody to an individual (e.g., who displays one or more symptoms of a Tau protein associated disease or disorder).

In some aspects, the invention provides a method for preventing the development of a Tau protein associated disease or disorder; or an anti-Tau antibody or a medicament comprising anti-Tau antibody for preventing the development of a Tau protein associated disease or disorder (such as any of the diseases or disorders described herein, for example, AD). The methods provided herein comprise administration of an amount (e.g., therapeutically effective amount) of an anti-Tau antibody to an individual (e.g., who is at risk of a Tau protein associated disease or disorder).

In some aspects, the invention provides a method for delaying the development of a Tau protein associated disease or disorder; or an anti-Tau antibody or a medicament comprising anti-Tau antibody for delaying the development of a Tau protein associated disease or disorder (such as any of the diseases or disorders described herein, for example, AD).

The methods provided herein comprise administration of an amount (e.g., therapeutically effective amount) of an anti-Tau antibody to an individual (e.g., who displays one or more symptoms of a Tau protein associated disease or disorder).

In a further aspect, the invention provides pharmaceutical formulations comprising any of the anti-Tau (e.g., anti-pTau) antibodies provided herein, e.g., for use in any of the above therapeutic methods. In one embodiment, a pharmaceutical formulation comprises any of the anti-Tau (e.g., anti-pTau) antibodies provided herein and a pharmaceutically acceptable carrier. In another embodiment, a pharmaceutical formulation comprises any of the anti-Tau (e.g., anti-pTau) antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

For example, the composition according to the invention may be administered in combination with other compositions comprising an biologically active substance or compound such as, for example, a known compound used in the medication of tauopathies and/or of amyloidoses, a group of diseases and disorders associated with amyloid or amyloid-like protein such as the amyloid protein involved in Alzheimer's Disease.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the biologically active agent or compound may comprise at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, [beta]- and 7-secretase inhibitors, tau proteins, neurotransmitter, /3-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, *Ginkgo biloba*, acyetyl-L-carnitine, idebenone, propentofylline, or a xanthine derivative, together with a binding peptide according to the invention including antibodies, particularly monoclonal antibodies and active fragments thereof, and, optionally, a pharmaceutically acceptable carrier and/or a diluent and/or an excipient and instructions for the treatment of diseases.

In a further embodiment, the composition according to the invention may comprise niacin or memantine together with a chimeric antibody or a humanized antibody according to the invention including antibodies, particularly monoclonal antibodies and active fragments thereof, and, optionally, a pharmaceutically acceptable carrier and/or a diluent and/or an excipient.

In still another embodiment of the invention compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the chimeric antibody or the humanized antibody according to the invention or active fragments thereof, and, optionally, a pharmaceutically acceptable carrier and/or a diluent and/or an excipient.

Other compounds that can be suitably used in compositions in addition to chimeric antibody or humanized antibody according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), nonsteroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-Tau antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-Tau antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third)

container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Tau (e.g., anti-pTau) antibody.

III. Examples

The following are examples of methods and compositions of the invention. It is understood that various other embodiments may be practiced, given the general description provided above.

Humanized antibodies against anti-pTau were affinity matured and analyzed as described below:

5202.4 Affinity Maturation Description

Humanized 5202.4 was displayed on the surface of filamentous bacteriophage M13 in Fab format using phagemid vectors (Table 1 shows amino acid sequence of 5202.4; the variable region of 5202.4 is identical to hACI-36-2B6-Ab1 antibody described in PCT/US13/32341, filed Mar. 15, 2013. Four libraries were constructed based on a stop template (a vector in which the CDRs for mutagenesis were deleted and stop codons inserted in an effort to reduce expression of non-mutated sequences). Kunkel mutagenesis with degenerate oligonucleotides was used to mutate the CDRs in each of the four libraries. Heavy chain and light chain were mutagenized separately; thus each library contained either a parental heavy chain and mutagenized light chain, or vice versa. In two of the libraries, either the heavy chain or the light chain was mutagenized using the scheme known as NNK walk, in which one CDR residue at a time (per CDR) is mutagenized using the degenerate codon NNK. NNK is capable of encoding all twenty natural amino acids and a stop codon. All three CDRs were mutagenized simultaneously. In the other two libraries, the three heavy chain or light chain CDRs were mutagenized simultaneously using "soft" mutagenesis. In this case, during oligonucleotide synthesis each nucleotide in the region selected for mutagenesis was replaced with a mixture containing 90% parental nucleotide and 3.3% of each of the non-parental nucleotides. Codon positions 2 and 3 were maintained as parental for residues CDR-L1 L27a, CDR-L1 L33 and CDR-H1 M34 (Kabat numbering). Mutagenized DNA was transformed into XL1 Blue *E. coli* and the library rescued with M13-based helper phage. The number of transformants was estimated to be between $2 \times 10^8 - 1 \times 10^9$ for each library.

Each library was subjected to three or four rounds of selection with biotinylated peptide in solution, using the peptide Biotinyl-18-amino-4,7,10,13,16-pentaoxaoctadecanoyl-Gly-Asp-Thr-Ser[PO3H2]-Pro-Trp-His-Leu-Ser[PO3H2]-Asn-Val-Ser-Ser-Thr-Gly-Ser-Ile-Asp-NH2 (SEQ ID NO:93). Phage/peptide complexes were captured on neutravidin-coated microplates, washed repeatedly, and eluted with 100 mM hydrochloric acid. Eluted phage were amplified in XL1 Blue *E. coli*, rescued with helper phage and purified by precipitation with PEG/NaCl. Concentrations of biotinylated peptide used were 250 nM (Round 1), 100 nM (Round 2), 40 nM (Round 3) and either 4 nM or 10 nM (Round 4). In some of the Round 4 selections, parental IgG (1 µM) was added to the phage/peptide mixture thirty minutes prior to capture.

Individual clones were isolated by limiting dilution and sequenced from plasmid DNA. Following Round 3 and, in a second experiment, following Round 4, consensus sequences were observed to emerge in the pools with mutagenized light chains. The most frequently observed mutations included: H27$^d$R, S27$^e$R, S27$^e$K, H28R, H28N, H28K, K30R, S52R, S52K, S56F, S56L, Q90S, A92R, H93R, H93Q, Y96R (all numbering is according to the Kabat system). 23 amino acid sequences were obtained, i.e., TAM1, TAM2, TAM3, TAM4, TAM5, TAM6, TAM7, TAM8, TAM9, TAM10, TAM11, TAM12, TAM13, TAM14, TAM15, TAM16, TAM17, TAM18, TAM19, TAM20, TAM21, TAM22, TAM23 (collectively, the "TAM proteins"). A total of 22 unique amino acid sequences were selected for further analysis and expressed as recombinant Fab fragments and as IgG by transient transfection of 293S cells (note: TAM20 and TAM22 represent the same amino acid sequence).

Figure 1A:
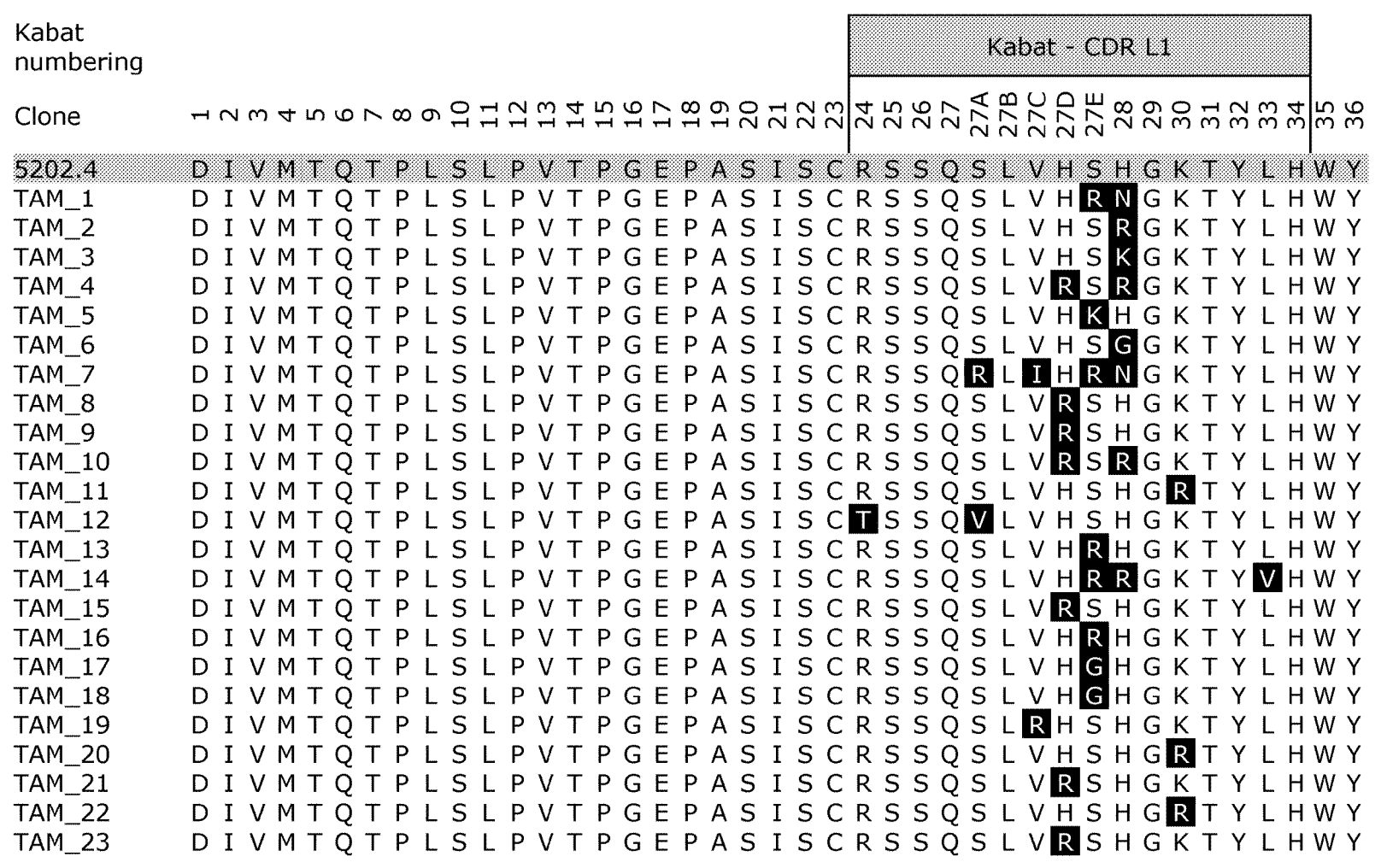
Figure 1B:
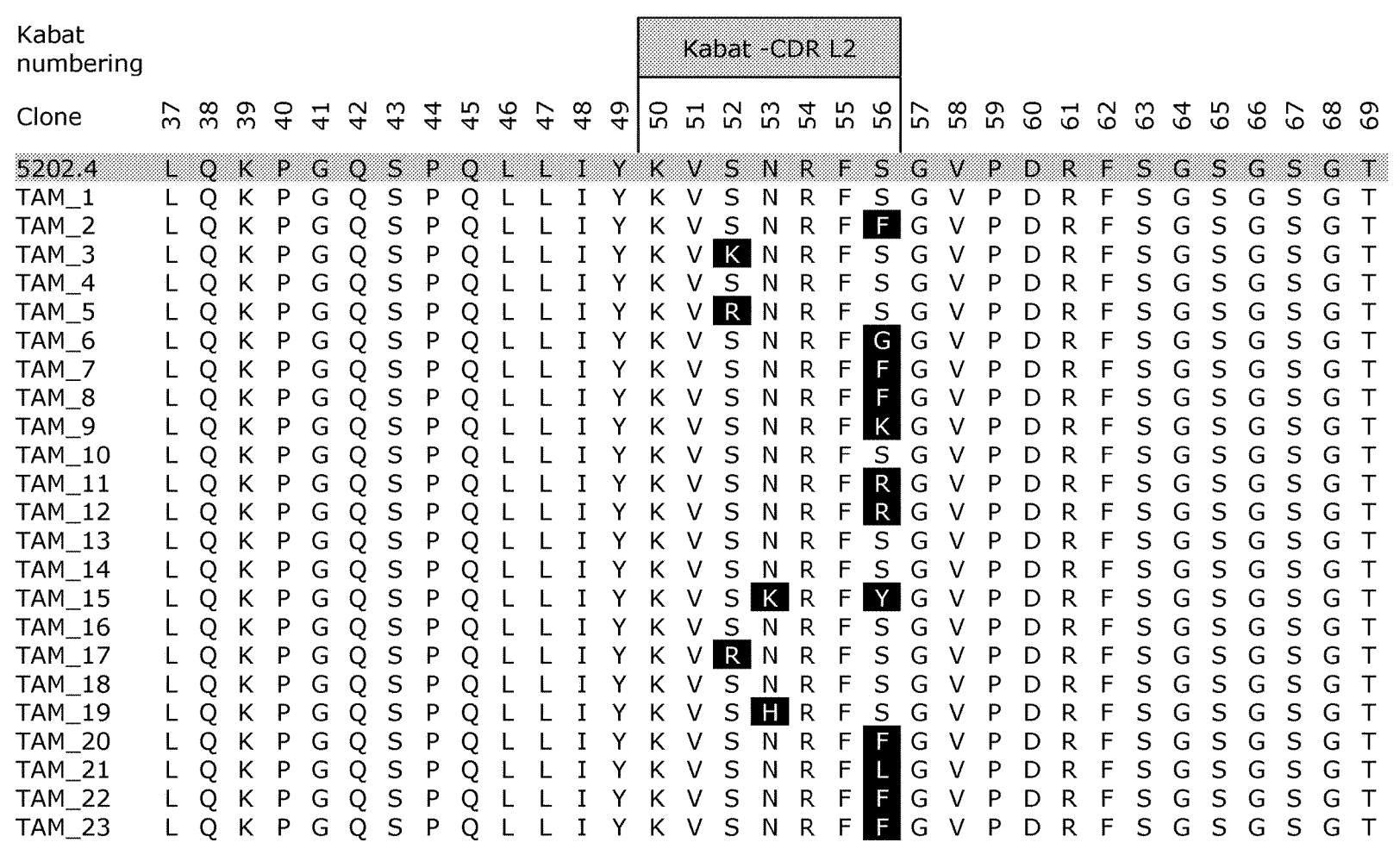
Figure 1C:
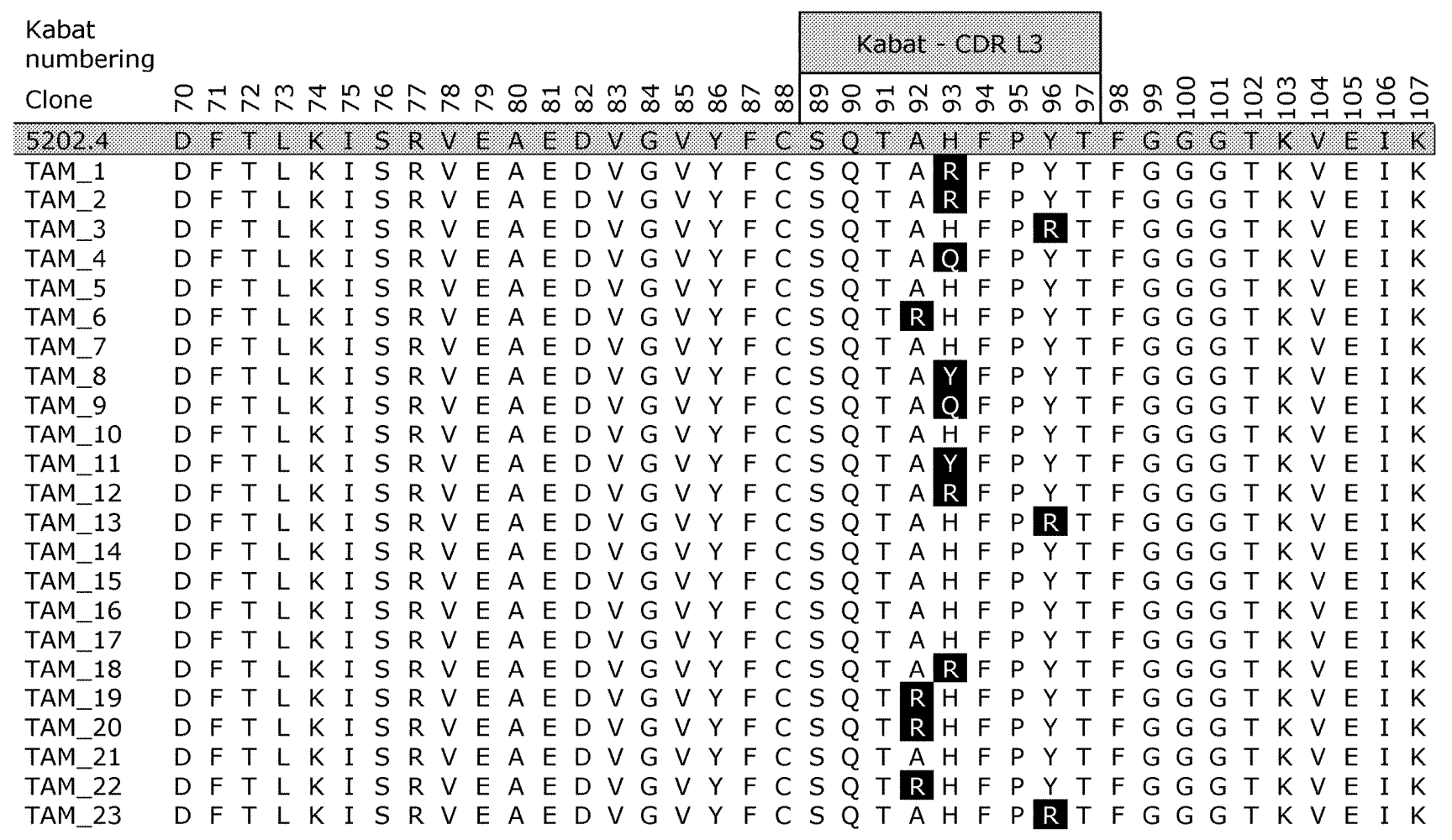

FIG. 1 shows the amino acid changes in the CDRs of the TAM proteins relative to 5202.4; Table 2A provides the amino acid sequences of the light chain CDRs of the TAM proteins and 5202.4; Table 2B provides the amino acid sequences of the heavy chain CDRs of the TAM proteins and 5202.4; Table 3 shows Kabat positions at which amino acid mutations occur and the type of mutations in the TAM proteins; Table 4 shows the variable light chain amino acid sequences and the variable heavy chain amino acid sequences of the TAM proteins; Table 5 shows the full-length light chain amino acid sequences of the TAM proteins, Table 7 shows the full-length heavy chain amino acid sequences (IgG1) of the TAM proteins. Table 6 shows the full-length heavy chain amino acid sequences of IgG4 isotypes of TAM antibodies. Table 8 shows the full-length heavy chain amino acid sequences of IgG1 N297G isotypes of TAM antibodies.

Antibody Selection and Characterization

Biacore instruments were used to characterize Fab and IgG using surface plasmon resonance analysis. For these experiments, Tau protein phosphorylated with Protein Kinase A (PKA) was immobilized directly onto a CM5 or Series S CM5 sensor chip using the Biacore Amine Coupling Kit and an immobilization buffer of sodium acetate pH5. Flow cell 1 was left untreated for use as a reference cell and data from this cell was subtracted from all sensorgrams prior to analysis. Regeneration buffer 10 mM Glycine pH1.7 was injected for 0.5-1 minute following each association/dissociation cycle. Antibody binding was assessed at a flow rate of 30 µl/min. Kinetic constants were determined by non-linear regression using the BIAevaluation software and a 1:1 binding model.

Screening of the 22 TAM clones was performed on a Biacore T100 instrument using a Series S CM5 chip, four non-zero concentrations of each Fab (2.4, 12, 60 and 300 nM). The results were ranked by KD and are shown in Table 9. From the KD rankings, TAM1, TAM2, TAM9, TAM19 and TAM20 were selected for further characterization. Two experiments were performed (Table 10), both using seven non-zero Fab concentrations including one replicate concentration. Experiment one utilized a Biacore T100 instrument, a Series S CM5 sensor chip and 30 second regeneration period. Experiment two utilized a Biacore 3000 instrument, a CM5 sensor chip and a 1 minute regeneration period. Table 10 shows binding kinetics of selected affinity-matured variants of 5202.4 (Fab format) to PKA-phosphorylated Tau protein. Density of ligand: approximately 403 RU PKA-phosphorylated tau protein was immobilized in experiment 1 and approximately 356 RU in experiment 2.

Clones were also analyzed in IgG (IgG1) format, using a CM5 sensor chip and a Biacore 2000 instrument. The regeneration time was 1 minute. Six non-zero concentrations including one replicate concentration were tested; of these data from at least five of the six injections was included in the final analysis. Due to the bivalency of IgG, suboptimal 1:1 fitting may be expected in this format, and results may depend on the density of immobilized antigen. Two densities were assessed simultaneously using adjacent flow cells and the results shown in Table 11 (Table 11 shows binding kinetics of selected affinity-matured variants of 5202.4 (IgG format) to PKA-phosphorylated Tau protein). Density of ligand: approximately 153 RU PKA-phosphorylated tau protein was immobilized in flow cell 4 (ligand density 1) and approximately 824 RU of the same in flow cell 3 (ligand density 2). These data demonstrate that there is an avidity component to the binding of the antibodies to the ligand, and indicate that both arms of the antibody may contribute to the antibody's biding of the ligand.

Figures 2C, 2D, 2E, 2F:
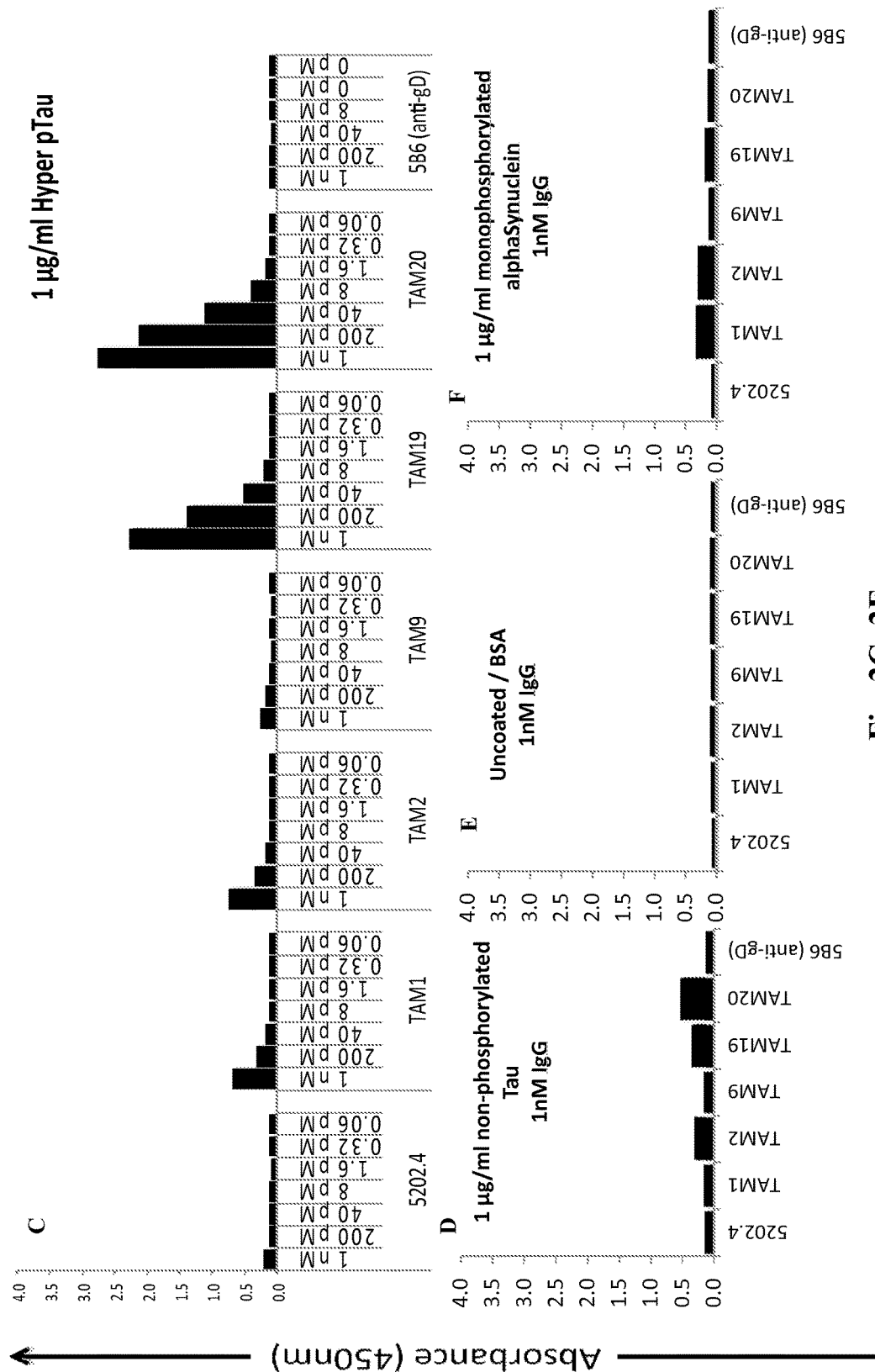

Specificity of the top five clones was assessed by ELISA. Microplates coated with 0.1 or 1 µg/ml non-phosphorylated full-length Tau, PKA-phosphorylated full-length Tau, hyper-phosphorylated full-length Tau or monophosphorylated alpha Synuclein were blocked with PBS/0.5% BSA/0.1% Tween 20 (BBT) for several hours at ambient temperature and exposed to anti-Tau IgG at the stated concentrations, in BBT, for two hours. The amino acid sequence of the full-length Tau (441 aa) used in this experiment is provided in Table 12 (SEQ ID NO:59). The PKA-phosphorylated Tau was obtained by incubation of the full-length Tau in vitro with Protein kinase A, which phosphorylates serine 409. The hyper-phosphorylated Tau was obtained by incubation of the full-length Tau in vitro with a cocktail of kinases including PKA, GSK3β, CDK5 and casein kinase 1 delta. Bound IgG was detected with peroxidase-conjugated anti-Human Fc and visualized with a 3,3',5,5"-tetramethylbenzidine (TMB)-based detection system. Following addition of an equal volume of 1M phosphoric acid the absorbance at 450 nm was quantified using a SpectraMax M2 platereader (Molecular Devices). TAM1, TAM2, TAM9, TAM19 and TAM20 IgG bound to plates coated with PKA-phosphorylated Tau but minimally if at all to plates coated with unphosphorylated Tau protein or monophosphorylated alpha Synuclein (FIG. 2).

Figure 3:
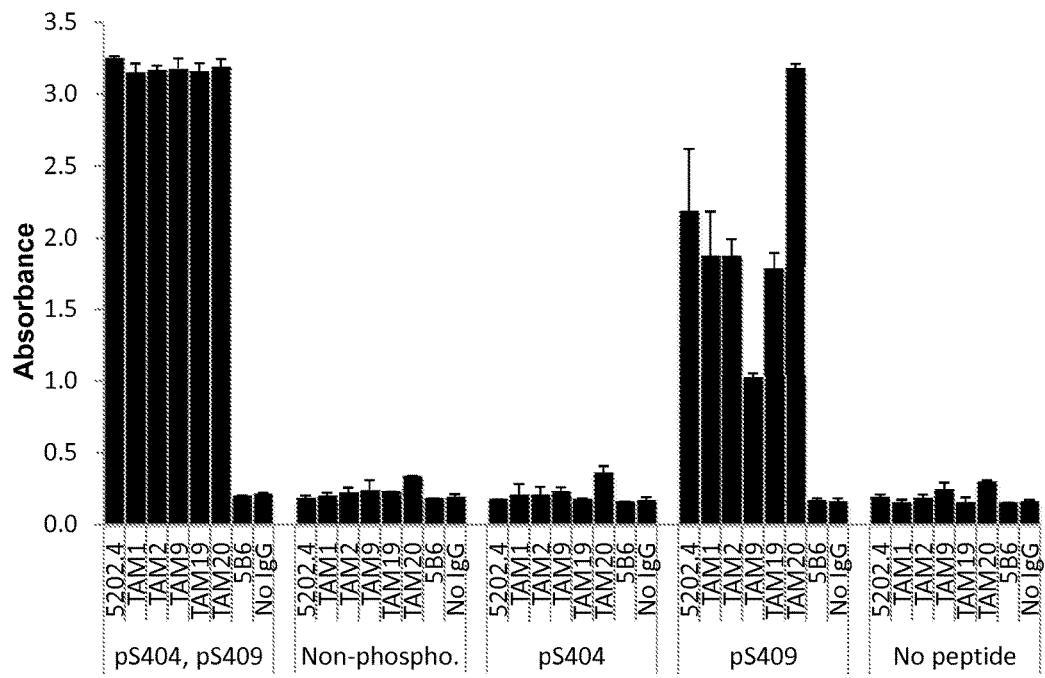
FIG. 3. Binding of immobilized IgG antibodies to Tau-derived biotinylated peptides containing pS404 and/or pS409 as measured by ELISA.

Specificity of the top five clones for phosphoserine 404 and phosphoserine 409 was also assessed by ELISA. In one experiment (FIG. 3), Nunc maxisorp microplates were coated with 5 µg/ml IgG in coating buffer (sodium carbonate pH9.6) for 70 minutes at ambient temperature. Non-specific binding sites were blocked with BBT for a minimum of 2 hours then the plates washed and 10 nM biotinylated peptide in BBT added. After 1.5 hours bound peptide was detected by a 65 minute incubation with peroxidase-conjugated Streptavidin and detection with TMB as described above. FIG. 3 shows mean and range of duplicate wells; y-axis represents absorbance at 450 nm. The peptides synthesized and used in this experiment (which correspond to amino acids 401-418 of full-length Tau) have the following amino acid sequences (Table B):

TABLE B

| Peptide | Peptide sequence X = phosphoserine |
|---|---|
| pS404, pS409 | Biotin - linker - GDTXPRHLXNVSSTGSID SEQ ID NO: 94 |
| Non-phospho. | Biotin - linker - GDTSPRHLSNVSSTGSID SEQ ID NO: 95 |
| pS404 | Biotin - linker - GDTXPRHLSNVSSTGSID SEQ ID NO: 96 |
| pS409 | Biotin - linker - GDTSPRHLXNVSSTGSID SEQ ID NO: 97 |

Figures 4A, 4B:
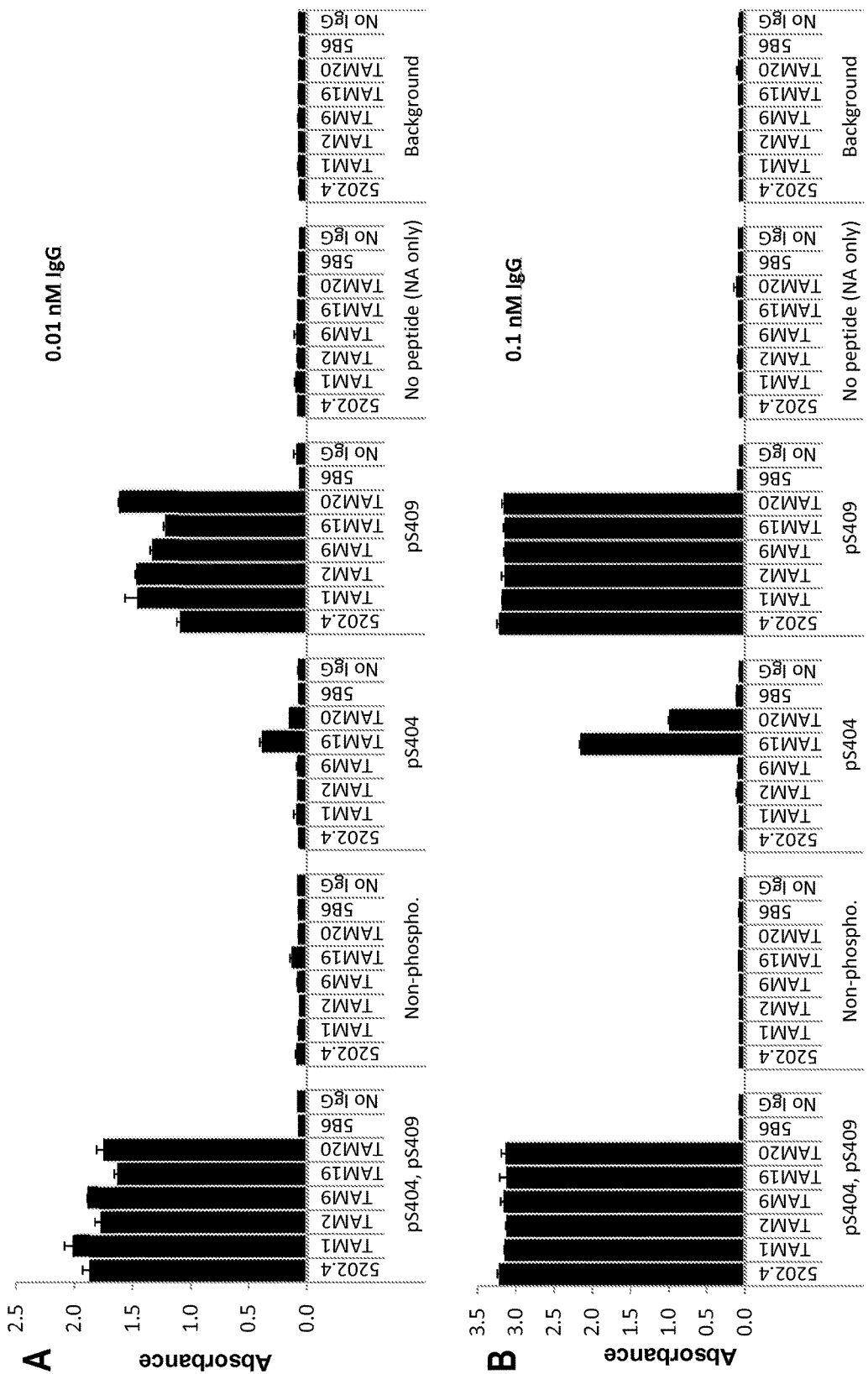
FIG. 4 (A-E). Binding of IgG antibodies to immobilized Tau-derived biotinylated peptides containing pS404 and/or pS409 as measured by ELISA.
Figures 4C, 4D:
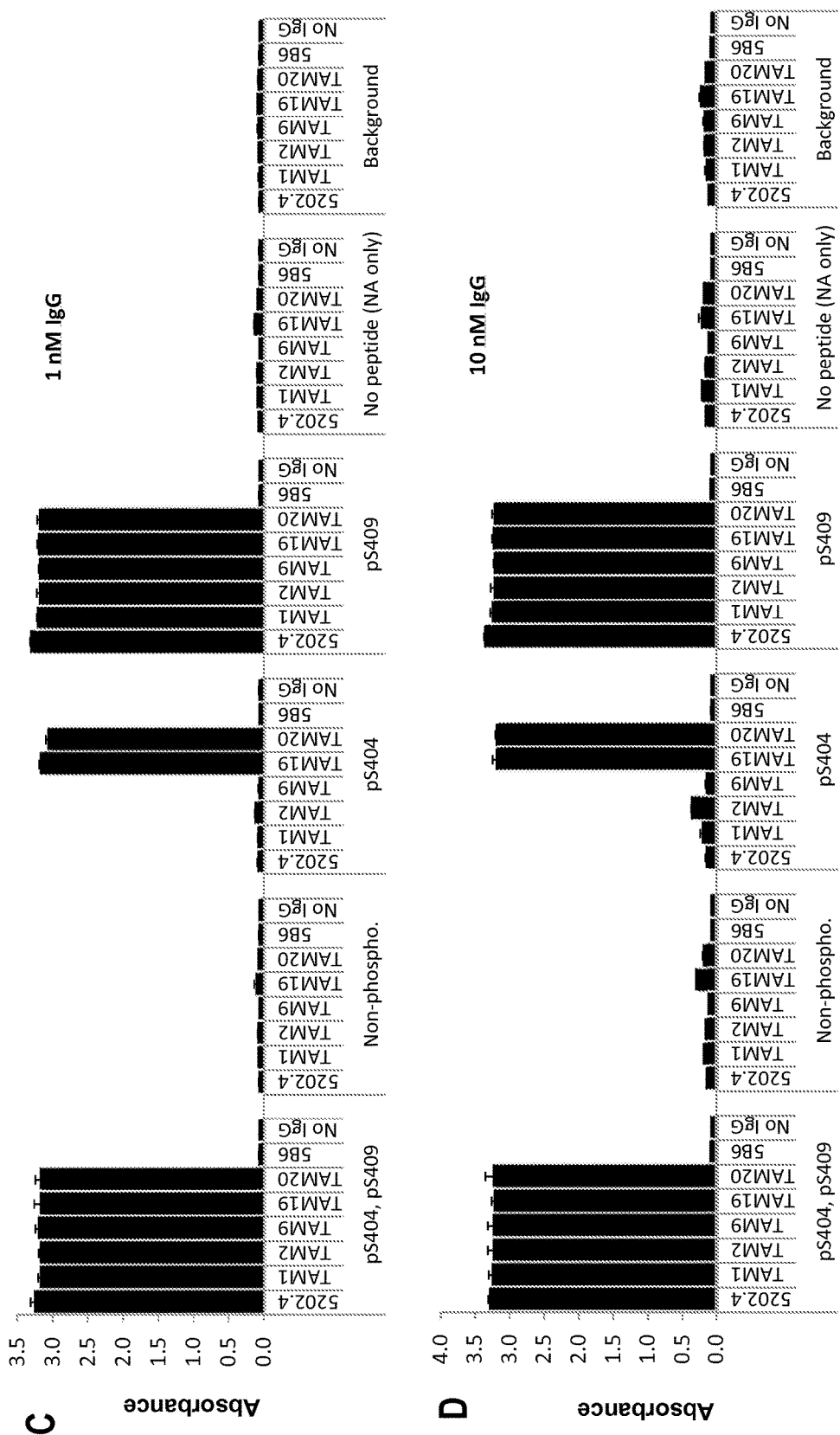
Figure 4E:
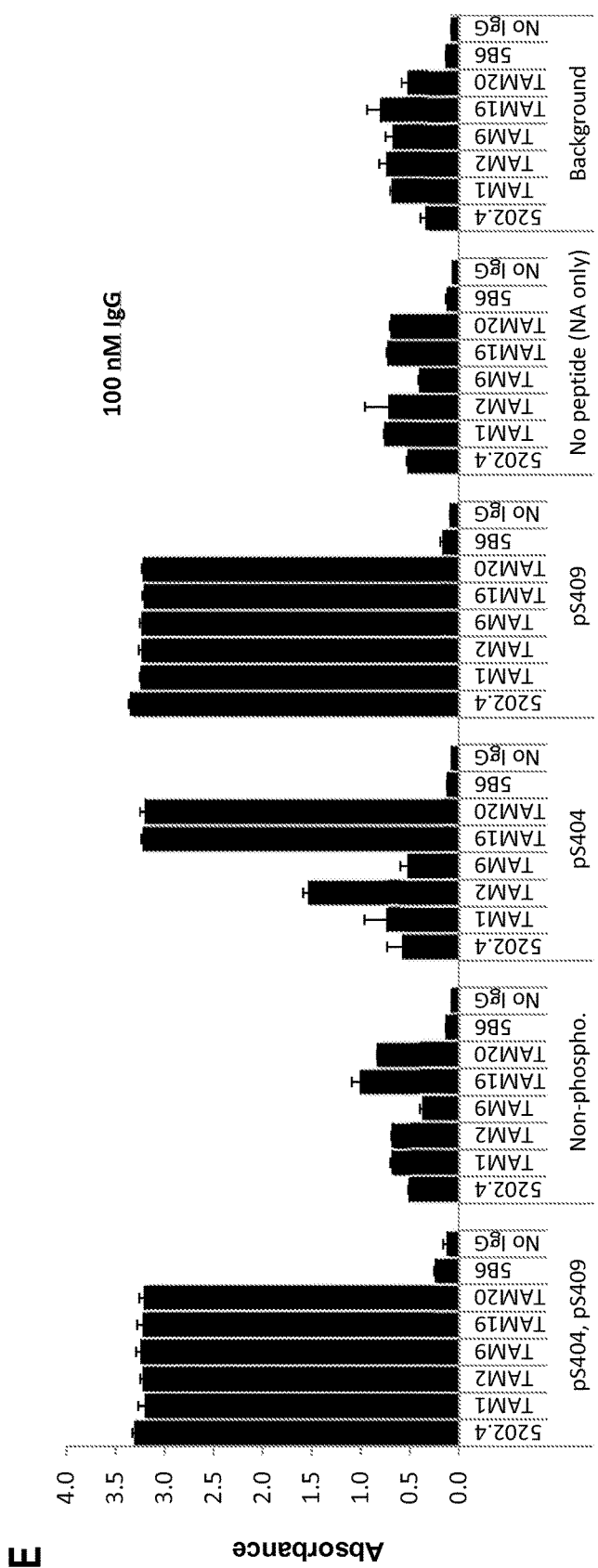

In another experiment (FIG. 4), Nunc maxisorp microplates were coated with 5 µg/ml Neutravidin in coating buffer overnight at 4° C. and non-specific binding sites blocked by incubation with BBT for a minimum of 2 hours. Biotinylated peptides (20 nM) were then allowed to bind for 1.5 hours before plates were washed and exposed to IgG at the stated concentrations for 1 hour. The same peptides were used in this experiment as in the experiment shown in FIG. 3 and described above (see Table B). Bound IgG was detected with peroxidase-conjugated anti-human antibody and detection with TMB as described above. Various IgG concentrations were used (0.01 nM, 0.1 nM, 1 nM, 10 nM and 100 nM). FIG. 4 shows mean and range of duplicate wells; y-axis represents absorbance at 450 nm. "Background" indicates signal from wells not coated with Neutravidin; "No peptide" indicates signal from wells coated with Neutravidin but not exposed to peptide.

CONCLUSION

The data show that affinity matured antibodies that specifically recognize and bind a phosphorylated epitope on Tau have been generated. Some of the generated antibodies display high specificity and/or high affinity for pTau.

TAM1, TAM2 and TAM9 selectively identify phosphoserine 409 on Tau as shown by ELISA and Biacore. Overall, all the data also show selectivity of these antibodies (i.e., TAM1, TAM2 and TAM9) for phosphoserine 409 in the context of phosphorylated full-length Tau compared to non-phosphorylated full-length Tau.

TABLE 1

| Amino Acid Sequence of 5202.4 (hIgG1) | |
|---|---|
| Amino Acid Sequence of: | 5202.4 (hIgG1 antibody) |
| Light Chain Variable Region | DIVMTQTPLSLPVTPGEPASISCRSSQSLVHSHGKTYLHWYLQKPGQSP QLLIYKVSNRFSGVPDRFSGSGSGTDFTLKISRVEAEDVGVYFCSQTAH FPYTFGGGTKVEIK (SEQ ID NO: 60) |
| Light Chain | DIVMTQTPLSLPVTPGEPASISCRSSQSLVHSHGKTYLHWYLQKPGQSP QLLIYKVSNRFSGVPDRFSGSGSGTDFTLKISRVEAEDVGVYFCSQTAH |

TABLE 1-continued

Amino Acid Sequence of 5202.4 (hIgG1)

| Amino Acid Sequence of: | 5202.4 (hIgG1 antibody) |
|---|---|
| | FPYTFGGGTKVEIKRTVAAPSVFIFPPSDEQLKSGTASVVCLLNNFYPRE<br>AKVQWKVDNALQSGNSQESVTEQDSKDSTYSLSSTLTLSKADYEKHK<br>VYACEVTHQGLSSPVTKSFNRGEC (SEQ ID NO: 61) |
| Heavy Chain Variable Region | EVQLVQSGAEVKKPGSSVKVSCKASGYTFTDYYMNWVRQAPGQGLE<br>WIGDINPNRGGTTYNQKFKGRVTITVDKSTSTAYMELSSLRSEDTAVY<br>YCASYYAVGYWGQGTTVTVSS (SEQ ID NO: 62) |
| Heavy Chain | EVQLVQSGAEVKKPGSSVKVSCKASGYTFTDYYMNWVRQAPGQGLE<br>WIGDINPNRGGTTYNQKFKGRVTITVDKSTSTAYMELSSLRSEDTAVY<br>YCASYYAVGYWGQGTTVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEAL<br>HNHYTQKSLSLSPGK (SEQ ID NO: 63) |

TABLE 2A

Amino Acid Sequence of the CDRs of Light Chain Variable Regions of the TAM proteins and 5202.4

| Antibody | CDR L1 (HVR-L1) | CDR L2 (HVR-L2) | CDR L3 (HVR-L3) |
|---|---|---|---|
| 5202.4 | RSSQSLVHSHGKTYLH (SEQ ID NO: 15) | KVSNRFS (SEQ ID NO: 16) | SQTAHFPYT (SEQ ID NO: 30) |
| TAM_1 | RSSQSLVHRNGKTYLH (SEQ ID NO: 1) | KVSNRFS (SEQ ID NO: 16) | SQTARFPYT (SEQ ID NO: 27) |
| TAM_2 | RSSQSLVHSRGKTYLH (SEQ ID NO: 2) | KVSNRFF (SEQ ID NO: 17) | SQTARFPYT (SEQ ID NO: 27) |
| TAM_3 | RSSQSLVHSKGKTYLH (SEQ ID NO: 3) | KVKNRFS (SEQ ID NO: 18) | SQTAHFPRT (SEQ ID NO: 28) |
| TAM_4 | RSSQSLVRSRGKTYLH (SEQ ID NO: 4) | KVSNRFS (SEQ ID NO: 16) | SQTAQFPYT (SEQ ID NO: 29) |
| TAM_5 | RSSQSLVHKHGKTYLH (SEQ ID NO: 5) | KVRNRFS (SEQ ID NO: 19) | SQTAHFPYT (SEQ ID NO: 30) |
| TAM_6 | RSSQSLVHSGGKTYLH (SEQ ID NO: 6) | KVSNRFG (SEQ ID NO: 20) | SQTRHFPYT (SEQ ID NO: 31) |
| TAM_7 | RSSQRLIHRNGKTYLH (SEQ ID NO: 7) | KVSNRFF (SEQ ID NO: 17) | SQTAHFPYT (SEQ ID NO: 30) |
| TAM_8 | RSSQSLVRSHGKTYLH (SEQ ID NO: 8) | KVSNRFF (SEQ ID NO: 17) | SQTAYFPYT (SEQ ID NO: 32) |
| TAM_9 | RSSQSLVRSHGKTYLH (SEQ ID NO: 8) | KVSNRFK (SEQ ID NO: 21) | SQTAQFPYT (SEQ ID NO: 29) |
| TAM_10 | RSSQSLVRSRGKTYLH (SEQ ID NO: 4) | KVSNRFS (SEQ ID NO: 16) | SQTAHFPYT (SEQ ID NO: 30) |
| TAM_11 | RSSQSLVHSHGRTYLH (SEQ ID NO: 9) | KVSNRFR (SEQ ID NO: 22) | SQTAYFPYT (SEQ ID NO: 32) |
| TAM_12 | TSSQVLVHSHGKTYLH (SEQ ID NO: 10) | KVSNRFR (SEQ ID NO: 22) | SQTARFPYT (SEQ ID NO: 27) |
| TAM_13 | RSSQSLVHRHGKTYLH (SEQ ID NO: 11) | KVSNRFS (SEQ ID NO: 16) | SQTAHFPRT (SEQ ID NO: 28) |
| TAM_14 | RSSQSLVHRRGKTYVH (SEQ ID NO: 12) | KVSNRFS (SEQ ID NO: 16) | SQTAHFPYT (SEQ ID NO: 30) |
| TAM_15 | RSSQSLVRSHGKTYLH (SEQ ID NO: 8) | KVSKRFY (SEQ ID NO: 23) | SQTAHFPYT (SEQ ID NO: 30) |
| TAM_16 | RSSQSLVHRHGKTYLH (SEQ ID NO: 11) | KVSNRFS (SEQ ID NO: 16) | SQTAHFPYT (SEQ ID NO: 30) |
| TAM_17 | RSSQSLVHGHGKTYLH (SEQ ID NO: 13) | KVRNRFS (SEQ ID NO: 24) | SQTAHFPYT (SEQ ID NO: 30) |
| TAM_18 | RSSQSLVHGHGKTYLH (SEQ ID NO: 13) | KVSNRFS (SEQ ID NO: 16) | SQTARFPYT (SEQ ID NO: 27) |
| TAM_19 | RSSQSLVRSHGKTYLH (SEQ ID NO: 14) | KVSHRFS (SEQ ID NO: 25) | SQTRHFPYT (SEQ ID NO: 31) |
| TAM_20 | RSSQSLVHSHGRTYLH (SEQ ID NO: 9) | KVSNRFF (SEQ ID NO: 17) | SQTRHFPYT (SEQ ID NO: 31) |
| TAM_21 | RSSQSLVRSHGKTYLH (SEQ ID NO: 8) | KVSNRFL (SEQ ID NO: 26) | SQTAHFPYT (SEQ ID NO: 30) |

TABLE 2A-continued

Amino Acid Sequence of the CDRs of Light Chain Variable Regions of the TAM proteins and 5202.4

| Antibody | CDR L1 (HVR-L1) | CDR L2 (HVR-L2) | CDR L3 (HVR-L3) |
|---|---|---|---|
| TAM_22 | RSSQSLVHSHGRTYLH (SEQ ID NO: 9) | KVSNRFF (SEQ ID NO: 17) | SQTRHFPYT (SEQ ID NO: 31) |
| TAM_23 | RSSQSLVRSHGKTYLH (SEQ ID NO: 8) | KVSNRFF (SEQ ID NO: 17) | SQTAHFPRT (SEQ ID NO: 28) |

TABLE 2B

Amino Acid Sequence of the CDRs of Heavy Chain Variable Regions of the TAM proteins and 5202.4 (it is the same in all the TAM proteins and 5202.4)

| CDR H1 (HVR-H1) | CDR H2 (HVR-H2) | CDR H3 (HVR-H3) |
|---|---|---|
| GYTFTDYYMN (SEQ ID NO: 33) | DINPNRGGTTYNQKFKG (SEQ ID NO: 34) | YYAVGY (SEQ ID NO: 35) |

TABLE 3

Amino Acid Mutations in the Sequence of Light Chain CDRs in the TAM proteins relative to 5202.4

| Kabat position | 5202.4 | Mutation |
|---|---|---|
| 24 | R | T |
| 27A | S | RV |
| 27C | V | RI |
| 27D | H | R |
| 27E | S | RGK |
| 28 | H | RKNG |
| 30 | K | R |
| 33 | L | V |
| 52 | S | KR |
| 53 | N | KH |
| 56 | S | FGKRYL |
| 92 | A | R |
| 93 | H | RQY |
| 96 | Y | R |

TABLE 4

Amino Acid Sequences of Variable Light Chain and Variable Heavy Chain regions of the TAM proteins

| Name of Antibody | Variable Light Chain | Variable Heavy Chain |
|---|---|---|
| TAM_1 | DIVMTQTPLSLPVTPGEPASISC RSSQSLVHRNGKTYLHWYLQ KPGQSPQLLIYKVSNRFSGVPD RFSGSGSGTDFTLKISRVEAED VGVYFCSQTARFPYTFGGGTK VEIK (SEQ ID NO: 36) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_2 | DIVMTQTPLSLPVTPGEPASISC RSSQSLVHSRGKTYLHWYLQK PGQSPQLLIYKVSNRFFGVPDR FSGSGSGTDFTLKISRVEAEDV GVYFCSQTARFPYTFGGGTKV EIK (SEQ ID NO: 37) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_3 | DIVMTQTPLSLPVTPGEPASISC RSSQSLVHSKGKTYLHWYLQK PGQSPQLLIYKVKNRFSGVPDR FSGSGSGTDFTLKISRVEAEDV GVYFCSQTAHFPRTFGGGTKV EIK (SEQ ID NO: 38) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_4 | DIVMTQTPLSLPVTPGEPASISC RSSQSLVRSRGKTYLHWYLQK PGQSPQLLIYKVSNRFSGVPDR FSGSGSGTDFTLKISRVEAEDV GVYFCSQTAQFPYTFGGGTKV EIK (SEQ ID NO: 39) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_5 | DIVMTQTPLSLPVTPGEPASISC RSSQSLVHKHGKTYLHWYLQ KPGQSPQLLIYKVRNRFSGVPD | EVQLVQSGAEVKKPGSSVKVSCKA SGYTFTDYYMNWVRQAPGQGLE WIGDINPNRGGTTYNQKFKGRVTIT |

TABLE 4-continued

Amino Acid Sequences of Variable Light Chain and
Variable Heavy Chain regions of the TAM proteins

| Name of Antibody | Variable Light Chain | Variable Heavy Chain |
| --- | --- | --- |
| | RFSGSGSGTDFTLKISRVEAED VGVYFCSQTAHFPYTFGGGTK VEIK (SEQ ID NO: 40) | VDKSTSTAYMELSSLRSEDTAVYY CASYYAVGYWGQGTTVTVSS (SEQ ID NO: 58) |
| TAM_6 | DIVMTQTPLSLPVTPGEPASISC RSSQSLVHSGGKTYLHWYLQK PGQSPQLLIYKVSNRFGGVPDR FSGSGSGTDFTLKISRVEAEDV GVYFCSQTRHFPYTFGGGTKV EIK (SEQ ID NO: 41) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_7 | DIVMTQTPLSLPVTPGEPASISC RSSQRLIHRNGKTYLHWYLQK PGQSPQLLIYKVSNRFFGVPDR FSGSGSGTDFTLKISRVEAEDV GVYFCSQTAHFPYTFGGGTKV EIK (SEQ ID NO: 42) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_8 | DIVMTQTPLSLPVTPGEPASISC RSSQSLVRSHGKTYLHWYLQK PGQSPQLLIYKVSNRFFGVPDR FSGSGSGTDFTLKISRVEAEDV GVYFCSQTAYFPYTFGGGTKV EIK (SEQ ID NO: 43) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_9 | DIVMTQTPLSLPVTPGEPASISC RSSQSLVRSHGKTYLHWYLQK PGQSPQLLIYKVSNRFKGVPDR FSGSGSGTDFTLKISRVEAEDV GVYFCSQTAQFPYTFGGGTKV EIK (SEQ ID NO: 44) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_10 | DIVMTQTPLSLPVTPGEPASISC RSSQSLVRSRGKTYLHWYLQK PGQSPQLLIYKVSNRFSGVPDR FSGSGSGTDFTLKISRVEAEDV GVYFCSQTAHFPYTFGGGTKV EIK (SEQ ID NO: 45) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_11 | DIVMTQTPLSLPVTPGEPASISC RSSQSLVHSHGRTYLHWYLQK PGQSPQLLIYKVSNRFRGVPDR FSGSGSGTDFTLKISRVEAEDV GVYFCSQTAYFPYTFGGGTKV EIK (SEQ ID NO: 46) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_12 | DIVMTQTPLSLPVTPGEPASISC TSSQVLVHSHGKTYLHWYLQ KPGQSPQLLIYKVSNRFRGVPD RFSGSGSGTDFTLKISRVEAED VGVYFCSQTARFPYTFGGGTK VEIK (SEQ ID NO: 47) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_13 | DIVMTQTPLSLPVTPGEPASISC RSSQSLVHRHGKTYLHWYLQ KPGQSPQLLIYKVSNRFSGVPD RFSGSGSGTDFTLKISRVEAED VGVYFCSQTAHFPRTFGGGTK VEIK (SEQ ID NO: 48) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_14 | DIVMTQTPLSLPVTPGEPASISC RSSQSLVHRRGKTYVHWYLQ KPGQSPQLLIYKVSNRFSGVPD RFSGSGSGTDFTLKISRVEAED | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY |

TABLE 4-continued

Amino Acid Sequences of Variable Light Chain and
Variable Heavy Chain regions of the TAM proteins

| Name of Antibody | Variable Light Chain | Variable Heavy Chain |
|---|---|---|
| | VGVYFCSQTAHFPYTFGGGTK VEIK (SEQ ID NO: 49) | CASYYAVGYWGQGTTVTVSS (SEQ ID NO: 58) |
| TAM_15 | DIVMTQTPLSLPVTPGEPASISC RSSQSLVRSHGKTYLHWYLQK PGQSPQLLIYKVSKRFYGVPDR FSGSGSGTDFTLKISRVEAEDV GVYFCSQTAHFPYTFGGGTKV EIK (SEQ ID NO: 50) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_16 | DIVMTQTPLSLPVTPGEPASISC RSSQSLVHRHGKTYLHWYLQ KPGQSPQLLIYKVSNRFSGVPD RFSGSGSGTDFTLKISRVEAED VGVYFCSQTAHFPYTFGGGTK VEIK (SEQ ID NO: 51) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_17 | DIVMTQTPLSLPVTPGEPASISC RSSQSLVHGHGKTYLHWYLQ KPGQSPQLLIYKVRNRFSGVPD RFSGSGSGTDFTLKISRVEAED VGVYFCSQTAHFPYTFGGGTK VEIK (SEQ ID NO: 52) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_18 | DIVMTQTPLSLPVTPGEPASISC RSSQSLVHGHGKTYLHWYLQ KPGQSPQLLIYKVSNRFSGVPD RFSGSGSGTDFTLKISRVEAED VGVYFCSQTARFPYTFGGGTK VEIK (SEQ ID NO: 53) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_19 | DIVMTQTPLSLPVTPGEPASISC RSSQSLRHSHGKTYLHWYLQK PGQSPQLLIYKVSHRFSGVPDR FSGSGSGTDFTLKISRVEAEDV GVYFCSQTRHFPYTFGGGTKV EIK (SEQ ID NO: 54) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_20 | DIVMTQTPLSLPVTPGEPASISC RSSQSLVHSHGRTYLHWYLQK PGQSPQLLIYKVSNRFFGVPDR FSGSGSGTDFTLKISRVEAEDV GVYFCSQTRHFPYTFGGGTKV EIK (SEQ ID NO: 55) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_21 | DIVMTQTPLSLPVTPGEPASISC RSSQSLVRSHGKTYLHWYLQK PGQSPQLLIYKVSNRFLGVPDR FSGSGSGTDFTLKISRVEAEDV GVYFCSQTAHFPYTFGGGTKV EIK (SEQ ID NO: 56) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_22 | DIVMTQTPLSLPVTPGEPASISC RSSQSLVHSHGRTYLHWYLQK PGQSPQLLIYKVSNRFFGVPDR FSGSGSGTDFTLKISRVEAEDV GVYFCSQTRHFPYTFGGGTKV EIK (SEQ ID NO: 55) | EVQLVQSGAEVKKPGSSVKVSCKA SGYTFTDYYMNWVRQAPGQGLE WIGDINPNRGGTTYNQKFKGRVTIT VDKSTSTAYMELSSLRSEDTAVYY CASYYAVGYWGQGTTVTVSS (SEQ ID NO: 58) |
| TAM_23 | DIVMTQTPLSLPVTPGEPASISC RSSQSLVRSHGKTYLHWYLQK PGQSPQLLIYKVSNRFFGVPDR | EVQLVQSGAEVKKPGSSVKVSCKA SGYTFTDYYMNWVRQAPGQGLE WIGDINPNRGGTTYNQKFKGRVTIT |

TABLE 4-continued

Amino Acid Sequences of Variable Light Chain and Variable Heavy Chain regions of the TAM proteins

| Name of Antibody | Variable Light Chain | Variable Heavy Chain |
|---|---|---|
| | FSGSGSGTDFTLKISRVEAEDV GVYFCSQTAHFPRTFGGGTKV EIK (SEQ ID NO: 57) | VDKSTSTAYMELSSLRSEDTAVYY CASYYAVGYWGQGTTVTVSS (SEQ ID NO: 58) |

TABLE 5

Full Length Amino Acid Sequences of Light Chains of the TAM proteins

| Name of Antibody | Sequence of Light Chain |
|---|---|
| TAM_1 | DIVMTQTPLSLPVTPGEPASISCRSSQSLVHRNGKTYLHWYLQKPGQS PQLLIYKVSNRFSGVPDRFSGSGSGTDFTLKISRVEAEDVGVYFCSQTA RFPYTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 64) |
| TAM_2 | DIVMTQTPLSLPVTPGEPASISCRSSQSLVHSRGKTYLHWYLQKPGQS PQLLIYKVSNRFFGVPDRFSGSGSGTDFTLKISRVEAEDVGVYFCSQTA RFPYTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 65) |
| TAM_3 | DIVMTQTPLSLPVTPGEPASISCRSSQSLVHSKGKTYLHWYLQKPGQS PQLLIYKVKNRFSGVPDRFSGSGSGTDFTLKISRVEAEDVGVYFCSQT AHFPRTFGGGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC (SEQ ID NO: 66) |
| TAM_4 | DIVMTQTPLSLPVTPGEPASISCRSSQSLVRSRGKTYLHWYLQKPGQS PQLLIYKVSNRFSGVPDRFSGSGSGTDFTLKISRVEAEDVGVYFCSQTA QFPYTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 67) |
| TAM_5 | DIVMTQTPLSLPVTPGEPASISCRSSQSLVHKHGKTYLHWYLQKPGQS PQLLIYKVRNRFSGVPDRFSGSGSGTDFTLKISRVEAEDVGVYFCSQT AHFPYTFGGGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC (SEQ ID NO: 68) |
| TAM_6 | DIVMTQTPLSLPVTPGEPASISCRSSQSLVHSGGKTYLHWYLQKPGQS PQLLIYKVSNRFGGVPDRFSGSGSGTDFTLKISRVEAEDVGVYFCSQT RHFPYTFGGGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC (SEQ ID NO: 69) |
| TAM_7 | DIVMTQTPLSLPVTPGEPASISCRSSQRLIHRNGKTYLHWYLQKPGQSP QLLIYKVSNRFFGVPDRFSGSGSGTDFTLKISRVEAEDVGVYFCSQTA HFPYTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 70) |
| TAM_8 | DIVMTQTPLSLPVTPGEPASISCRSSQSLVRSHGKTYLHWYLQKPGQS PQLLIYKVSNRFFGVPDRFSGSGSGTDFTLKISRVEAEDVGVYFCSQTA YFPYTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 71) |
| TAM_9 | DIVMTQTPLSLPVTPGEPASISCRSSQSLVRSHGKTYLHWYLQKPGQS PQLLIYKVSNRFKGVPDRFSGSGSGTDFTLKISRVEAEDVGVYFCSQT |

TABLE 5-continued

Full Length Amino Acid Sequences of Light Chains of the TAM proteins

| Name of Antibody | Sequence of Light Chain |
|---|---|
| | AQFPYTFGGGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC<br>(SEQ ID NO: 72) |
| TAM_10 | DIVMTQTPLSLPVTPGEPASISCRSSQSLVRSRGKTYLHWYLQKPGQS<br>PQLLIYKVSNRFSGVPDRFSGSGSGTDFTLKISRVEAEDVGVYFCSQTA<br>HFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 73) |
| TAM_11 | DIVMTQTPLSLPVTPGEPASISCRSSQSLVHSHGRTYLHWYLQKPGQS<br>PQLLIYKVSNRFRGVPDRFSGSGSGTDFTLKISRVEAEDVGVYFCSQT<br>AYFPYTFGGGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC<br>(SEQ ID NO: 74) |
| TAM_12 | DIVMTQTPLSLPVTPGEPASISCTSSQVLVHSHGKTYLHWYLQKPGQS<br>PQLLIYKVSNRFRGVPDRFSGSGSGTDFTLKISRVEAEDVGVYFCSQT<br>ARFPYTFGGGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC<br>(SEQ ID NO: 75) |
| TAM_13 | DIVMTQTPLSLPVTPGEPASISCRSSQSLVHRHGKTYLHWYLQKPGQS<br>PQLLIYKVSNRFSGVPDRFSGSGSGTDFTLKISRVEAEDVGVYFCSQTA<br>HFPRTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 76) |
| TAM_14 | DIVMTQTPLSLPVTPGEPASISCRSSQSLVHRRGKTYVHWYLQKPGQS<br>PQLLIYKVSNRFSGVPDRFSGSGSGTDFTLKISRVEAEDVGVYFCSQTA<br>HFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 77) |
| TAM_15 | DIVMTQTPLSLPVTPGEPASISCRSSQSLVRSHGKTYLHWYLQKPGQS<br>PQLLIYKVSKRFYGVPDRFSGSGSGTDFTLKISRVEAEDVGVYFCSQT<br>AHFPYTFGGGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC<br>(SEQ ID NO: 78) |
| TAM_16 | DIVMTQTPLSLPVTPGEPASISCRSSQSLVHRHGKTYLHWYLQKPGQS<br>PQLLIYKVSNRFSGVPDRFSGSGSGTDFTLKISRVEAEDVGVYFCSQTA<br>HFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 79) |
| TAM_17 | DIVMTQTPLSLPVTPGEPASISCRSSQSLVHGHGKTYLHWYLQKPGQS<br>PQLLIYKVRNRFSGVPDRFSGSGSGTDFTLKISRVEAEDVGVYFCSQT<br>AHFPYTFGGGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC<br>(SEQ ID NO: 80) |
| TAM_18 | DIVMTQTPLSLPVTPGEPASISCRSSQSLVHGHGKTYLHWYLQKPGQS<br>PQLLIYKVSNRFSGVPDRFSGSGSGTDFTLKISRVEAEDVGVYFCSQTA<br>RFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 81) |
| TAM_19 | DIVMTQTPLSLPVTPGEPASISCRSSQSLRHSHGKTYLHWYLQKPGQS<br>PQLLIYKVSHRFSGVPDRFSGSGSGTDFTLKISRVEAEDVGVYFCSQTR |

TABLE 5-continued

Full Length Amino Acid Sequences of Light Chains of the TAM proteins

| Name of Antibody | Sequence of Light Chain |
|---|---|
|  | HFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 82) |
| TAM_20 | DIVMTQTPLSLPVTPGEPASISCRSSQSLVHSHGRTYLHWYLQKPGQS<br>PQLLIYKVSNRFFGVPDRFSGSGSGTDFTLKISRVEAEDVGVYFCSQTR<br>HFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 83) |
| TAM_21 | DIVMTQTPLSLPVTPGEPASISCRSSQSLVRSHGKTYLHWYLQKPGQS<br>PQLLIYKVSNRFLGVPDRFSGSGSGTDFTLKISRVEAEDVGVYFCSQT<br>AHFPYTFGGGTKVEIKRTVAAPSVFIFPPSDEQLKSGTASVVCLLNNFY<br>PREAKVQWKVDNALQSGNSQESVTEQDSKDSTYSLSSTLTLSKADYE<br>KHKVYACEVTHQGLSSPVTKSFNRGEC<br>(SEQ ID NO: 84) |
| TAM_22 | DIVMTQTPLSLPVTPGEPASISCRSSQSLVHSHGRTYLHWYLQKPGQS<br>PQLLIYKVSNRFFGVPDRFSGSGSGTDFTLKISRVEAEDVGVYFCSQTR<br>HFPYTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 83) |
| TAM_23 | DIVMTQTPLSLPVTPGEPASISCRSSQSLVRSHGKTYLHWYLQKPGQS<br>PQLLIYKVSNRFFGVPDRFSGSGSGTDFTLKISRVEAEDVGVYFCSQTA<br>HFPRTFGGGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 85) |

TABLE 6

Full Length Amino Acid Sequences of Heavy Chain (IgG4) of TAM

| Name of Antibody | Sequence of Heavy Chain |
|---|---|
| TAM_1 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPCSRSTSESTAALGCLVKDYFPEPVTVSW<br>NSGALTSGVHTFPAVLQSSGLYSLSSVVTVPSSSLGTKT<br>YTCNVDHKPSNTKVDKRVESKYGPPCPPCPAPEFLGGPS<br>VFLFPPKPKDTLMISRTPEVTCVVVDVSQEDPEVQFNWY<br>VDGVEVHNAKTKPREEQFNSTYRVVSVLTVLHQDWLNGK<br>EYKCKVSNKGLPSSIEKTISKAKGQPREPQVYTLPPSQE<br>EMTKNQVSLTCLVKGFYPSDIAVEWESNGQPENNYKTTP<br>PVLDSDGSFFLYSRLTVDKSRWQEGNVFSCSVMHEALHN<br>HYTQKSLSLSLGK (SEQ ID NO: 86) |
| TAM_2 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPCSRSTSESTAALGCLVKDYFPEPVTVSW<br>NSGALTSGVHTFPAVLQSSGLYSLSSVVIVPSSSLGIKT<br>YTCNVDHKPSNTKVDKRVESKYGPPCPPCPAPEFLGGPS<br>VFLFPPKPKDTLMISRTPEVTCVVVDVSQEDPEVQFNWY<br>VDGVEVHNAKTKPREEQFNSTYRVVSVLTVLHQDWLNGK<br>EYKCKVSNKGLPSSIEKTISKAKGQPREPQVYTLPPSQE<br>EMTKNQVSLTCLVKGFYPSDIAVEWESNGQPENNYKTTP<br>PVLDSDGSFFLYSRLTVDKSRWQEGNVFSCSVMHEALHN<br>HYTQKSLSLSLGK (SEQ ID NO: 86) |
| TAM_3 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTIVIVSSAS<br>TKGPSVFPLAPCSRSTSESTAALGCLVKDYFPEPVTVSW<br>NSGALTSGVIIFFPAVLQSSGLYSLSSVVTVPSSSLGTK<br>TYTCNVDHKPSNTKVDKRVESKYGPPCPPCPAPEFLGGP<br>SVFLFPPKPKDTLMISRIPEVICVVVDVSQEDPEVQFNW<br>YVDGVEVHNAKTKPREEQFNSTYRVVSVLIVLHQDWLNG<br>KEYKCKVSNKGLPSSIEKTISKAKGQPREPQVYTLPPSQ<br>EEMTKNQVSLTCLVKGFYPSDIAVEWESNGQPENNYKTT<br>PPVLDSDGSFFLYSRLTVDKSRWQEGNVFSCSVMHEALH<br>NHYTQKSLSLSLGK (SEQ ID NO: 86) |
| TAM_4 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPCSRSTSESTAALGCLVKDYFPEPVTVSW<br>NSGALTSGVHTFPAVLQSSGLYSLSSVVTVPSSSLGTKT<br>YTCNVDHKPSNTKVDKRVESKYGPPCPPCPAPEFLGGPS<br>VFLFPPKPKDTLMISRTPEVTCVVVDVSQEDPEVQFNWY<br>VDGVEVHNAKTKPREEQFNSTYRVVSVLTVLHQDWLNGK<br>EYKCKVSNKGLPSSIEKTISKAKGQPREPQVYTLPPSQE<br>EMTKNQVSLTCLVKGFYPSDIAVEWESNGQPENNYKTTP<br>PVLDSDGSFFLYSRLTVDKSRWQEGNVFSCSVMHEALHN<br>HYTQKSLSLSLGK (SEQ ID NO: 86) |
| TAM_5 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPCSRSTSESTAALGCLVKDYFPEPVTVSW<br>NSGALTSGVHTFPAVLQSSGLYSLSSVVTVPSSSLGTKT<br>YTCNVDHKPSNTKVDKRVESKYGPPCPPCPAPEFLGGPS<br>VFLFPPKPKDTLMISRTPEVTCVVVDVSQEDPEVQFNWY<br>VDGVEVHNAKTKPREEQFNSTYRVVSVLTVLHQDWLNGK |

TABLE 6-continued

Full Length Amino Acid Sequences of Heavy Chain
(IgG4) of TAM

| Name of Antibody | Sequence of Heavy Chain |
| --- | --- |
| | EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_6 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLIVLHQDWLNGK EYKCKVSNKGLPSSIEKTISKAKGQPREPQVYTLPPSQE EMTKNQVSLTCLVKGFYPSDIAVEWESNGQPENNYKITP PVLDSDGSFFLYSRLTVDKSRWQEGNVFSCSVMHEALHN HYTQKSLSLSLGK (SEQ ID NO: 86) |
| TAM_7 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY PVDGVEVHNAKTKPREEQFNSTYRVVSVLIVLHQDWLNG KEYKCKVSNKGLPSSIEKTISKAKGQPREPQVYTLPPSQE EMTKNQVSLTCLVKGFYPSDIAVEWESNGQPENNYKITP PVLDSDGSFFLYSRLTVDKSRWQEGNVFSCSVMHEALHN HYTQKSLSLSLGK (SEQ ID NO: 86) |
| TAM_8 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_9 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_10 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_11 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLG (SEQ ID NO: 86) |
| TAM_12 | EVQLVQSGAEVKKPGSSVKVSCKASGYTFTDYYMNWVRQ GAPGQGLEWIDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_13 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_14 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_15 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NNSGALTSGVHTFPAVLQSSGLYSLSSVVTVPSSSLGTK RTYTCVDHKPSNTKVDKRVESKYGPPCPPCPAPEFLGGP SVFLFPPKPKDTLMISTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_16 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE |

TABLE 6-continued

Full Length Amino Acid Sequences of Heavy Chain (IgG4) of TAM

| Name of Antibody | Sequence of Heavy Chain |
|---|---|
| | EMTKNQVSLICLVKGFYPSDIAVEWESNGQPENNYKTIP PVLDSDGSFFLYSRLTVDKSRWQEGNVFSCSVMHEALHN HYTQKSLSLSLGK (SEQ ID NO: 86) |
| TAM_17 | EVQLVQSGAEVKKPGSSVKVSCKASGYTFTDYYMNWVRQ GAPGQGLEWIDINPNRGGTTYNQKFKGRVTITVDKSTST AYMELSSLRSEDTAVYYCASYYAVGYWGQGTTVTVSSAS FTKGPSVFPLAPCSRSTSESTAALGCLVKDYPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_18 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLICLVKGFYPSDIAVEWESNGQPENNYKTIP PVLDSDGSFFLYSRLTVDKSRWQEGNVFSCSVMHEALHN HYTQKSLSLSLGK (SEQ ID NO: 86) |
| TAM_19 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VVFLFPPKPKDTLMISRTPEVTCVVVDVSQEDPEVQFNW YVDGVEVHNAKTKPREEQYNSTYRVSVLTVLHQDWLNGK EYKCKVSNKGLPSSIEKTISKAKGQPREPQVYTLPPSQE EMTKNQVSLICLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_20 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NNSGALTSGVHTFPAVLQSSGLYSLSSVVTVPSSSLGTK TYTCVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_21 | EVQLVQSGAEVKKPGSSVKVSCKASGYTFTDYYMNWVRQ APGQGLEWIDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_22 | EVQLVQSGAEVKKPGSSVKVSCKASGYTFTDYYMNWVRQ APGQGLEWIDINPNRGGTTYNQKFKGRVTITVDKSTST AYMELSSLRSEDTAVYYCASYYAVGYWGQGTTVTVSSAS FTKGPSVFPLAPCSRSTSESTAALGCLVKDYPEPVTVSW NSGALTSGVHTFPAVLQSSGLYSLSSVVTVPSSSLGTKT RYTCNVDHKPSNTKVDKRVESKYGPPCPPCPAPEFLGGP SVFLFPPKPKDTLMISTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |
| TAM_23 | EVQLVQSGAEVKKPGSSVKVSCKASGYTFTDYYMNWVRQ GAPGQGLEWIDINPNRGGTTYNQKFKGRVTITVDKSTST AYMELSSLRSEDTAVYYCASYYAVGYWGQGTTVTVSSAS TKGPSVFPLAPCSRSTSESTAALGCLVKDYFPEPVTVSW NSGALTSGVHTFPAVLQSSGLYSLSSVVTVPSSSLGTKT YTCNVDHKPSNTKVDKRVESKYGPPCPPCPAPEFLGGPS VFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQE EMTKNQVSLTCLVKGFYPSDIAVEWESNGQPENNYKTTP PVLDSDGSFFLYSRLTVDKSRWQEGNVFSCSVMHEALHN HYTQKSLSLSLGK (SEQ ID NO: 86) |

TABLE 7

Full Length Amino Acid Sequences of Heavy Chain (IgG1) of the TAM proteins

| Name of Antibody | Sequence of Heavy Chain |
|---|---|
| TAM_1 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_2 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_3 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_4 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG |

TABLE 7-continued

Full Length Amino Acid Sequences of Heavy Chain (IgG1) of the TAM proteins

| Name of Antibody | Sequence of Heavy Chain |
|---|---|
|  | PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_5 | EVQLVQSGAEVKKPGSSVKVSCKASGYTFTDYYMNWVRQA<br>PGQGLEWIGDINPNRGGITYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVICVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_6 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>FPEPVTVSWNSGALTSGVHTFPAVLQSSGLYSLSSVVTVP<br>SSPSVFPLAPSSKSTSGGTAALGCLVKDYSLGTQTYICNV<br>LNHKPSNTKVDKKVEPKSCDKTHTCPPCPAPELLGGPSVF<br>TLFPPKPKDTMISRTPEVICVVVDVSHEDPEVKFNWYVDG<br>VEVHNAKTKPREEQYNSYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_7 | EVQLVQSGAEVKKPGSSVKVSCKASGYTFTDYYMNWVRQA<br>PGQGLEWIGDINPNRGGTTYNQKFKGRVTITVDKSTSTAY<br>YYMELSSLRSEDTAVYYCASAYGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_8 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_9 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_10 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_11 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_12 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_13 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_14 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV<br>NHKPSNTKVDKKVEPKSCDKTHTCPPCPAPELLGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQ<br>VSLTCLVKGFYPSDIAVEWESNGQPENNYKTTPPVLDSDG<br>SFFLYSKLTVDKSRWQQGNVFSCSVMHEALHNHYTQKSLS<br>LSPGK (SEQ ID NO: 87) |
| TAM_15 | EVQLVQSGAEVKKPGSSVKVSCKASGYTFTDYYMNWVRQA<br>PGQGLEWIGDINPNRGGTTYNQKFKGRVTITVDKSTSTAY<br>MELSSLRSEDTAVYYCASYYAVGYWGQGTTVTVSSASTKG<br>PSVFPLAPSSKSTSGGTAALGCLVKDYFPEPVTVSWNSGA<br>LTSGVHTFPAVLQSSGLYSLSSVVTVPSSSLGTQTYICNV |

TABLE 7-continued

Full Length Amino Acid Sequences of Heavy Chain (IgG1) of the TAM proteins

| Name of Antibody | Sequence of Heavy Chain |
|---|---|
| | NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_16 | EVQLVQSGAEVKKPGSSVKVSCKASGYTFTDYYMNWVRQA GPGQGLEWIDIDNPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLICLVKGFYPSDIAVEWESNGQPENNYKTIPPVLDSDG SFFLYSKLTVDKSRWQQGNVFSCSVMHEALHNHYTQKSLS LSPGK (SEQ ID NO: 87) |
| TAM_17 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTIVIVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL TYRVVSVLTVLHQDWLNGKEYKCKVSNKALPAPIEKTISK AKFPPKPKDTLMISRTPEVTCVVVDVSHEDPEVKFNWYVD GVEVHNAKTKPREEQYNSGQPREPQVYTLPPSREEMTKNQ VSLICLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_18 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTIVIVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLICLVKGFYPSDIAVEWESNGQPENNYKTIPPVLDSDG SFFLYSKLTVDKSRWQQGNVFSCSVMHEALHNHYTQKSLS LSPGK (SEQ ID NO: 87) |
| TAM_19 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTIVIVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVICVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_20 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_21 | EVQLVQSGAEVKKPGSSVKVSCKASGYTFTDYYMNWVRQA PGQGLEWIGDINPNRGGTTYNQKFKGRVTITVDKSTSTAY MELSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |
| TAM_22 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLICLVKGFYPSDIAVEWESNGQPENNYKTIPPVLDSDG SFFLYSKLTVDKSRWQQGNVFSCSVMHEALHNHYTQKSLS LSPGK (SEQ ID NO: 87) |
| TAM_23 | EVQLVQSGAEVKKPGSSVKVSCKASGYTFTDYYMNWVRQA PGQGLEWIGDINPNRGGTTYNQKFKGRVTITVDKSTSTAY MELSSLRSEDTAVYYCASYYAVGYWGQGTTVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 87) |

TABLE 8

Full Length Amino Acid Sequences of Heavy Chain (IgG1 N297G) of TAM

| Name of Antibody | Sequence of Heavy Chain |
|---|---|
| TAM_1 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_2 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL |

TABLE 8-continued

Full Length Amino Acid Sequences of Heavy Chain (IgG1 N297G) of TAM

| Name of Antibody | Sequence of Heavy Chain |
|---|---|
|  | NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_3 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_4 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_5 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_6 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_7 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_8 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLICLVKGFYPSDIAVEWESNGQPENNYK<br>TIPPVLDSDGSFFLYSKLTVDKSRWQQGNVFSCSVMHEA<br>LHNHYTQKSLSLSPGK (SEQ ID NO: 88) |
| TAM_9 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_10 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_11 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_12 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK<br>TTPPVLDSDGSFFLYSKLTVDKSRWQQGNVFSCSVMHEA<br>LHNHYTQKSLSLSPGK (SEQ ID NO: 88) |
| TAM_13 | EVQLVQSGAEVKKPGSSVKVSCKASGYTFTDYYMNWVRQ<br>APGQGLEWIGDINPNRGGTTYNQKFKGRVTITVDKSTST<br>AYMELSSLRSEDTAVYYCASYYAVGYWGQGTTVTVSSAS<br>TKGPSVFPLAPSSKSTSGGTAALGCLVKDYFPEPVTVSW<br>NSGALTSGVHTFPAVLQSSGLYSLSSVVTVPSSSLGTQT<br>YICNVNHKPSNTKVDKKVEPKSCDKTHTCPPCPAPELLG<br>GPSVFLFPPKPKDTLMISRTPEVTCVVVDVSHEDPEVKF<br>NWYVDGVEVHNAKTKPREEQYGSTYRVVSVLTVLHQDWL<br>NGKEYKCKVSNKALPAPIEKTISKAKGQPREPQVYTLPP<br>SREEMTKNQVSLTCLVKGFYPSDIAVEWESNGQPENNYK |

TABLE 8-continued

Full Length Amino Acid Sequences of Heavy Chain (IgG1 N297G) of TAM

| Name of Antibody | Sequence of Heavy Chain |
|---|---|
|  | TTPPVLDSDGSFFLYSKLTVDKSRWQQGNVFSCSVMHEA LHNHYTQKSLSLSPGK (SEQ ID NO: 88) |
| TAM_14 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_15 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_16 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_17 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_18 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_19 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_20 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_21 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_22 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVICVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLTCLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |
| TAM_23 | EVQLVQSGAEVKKPGSSVKVSCKASGYTFTDYYMNWVRQ APGQGLEWIGDINPNRGGTTYNQKFKGRVTITVDKSTST AYMELSSLRSEDTAVYYCASYYAVGYWGQGTTVTSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPELLG GPSVFLFPPKPKDTLMISRTPEVTCVVVDVSHEDPEVKF NWYVDGVEVHNAKTKPREEQYGSTYRVVSVLTVLHQDWL NGKEYKCKVSNKALPAPIEKTISKAKGQPREPQVYTLPP SREEMTKNQVSLICLVKGFYPSDIAVEWESNGQPENNYK TTPPVLDSDGSFFLYSKLTVDKSRWQQGNVFSCSVMHEA LHNHYTQKSLSLSPGK (SEQ ID NO: 88) |

TABLE 9

Biacore screening: Fabs ranked by KD
Ligand: PKA-phosphorylated Tau protein,
immobilized directly using amine coupling.
Analyte: Recombinant Fab

|  | ka (1/Ms) | kd (1/s) | KD (nM) |
|---|---|---|---|
| TAM1 | $5.3 \times 10^5$ | $1.5 \times 10^{-3}$ | 2.9 |
| TAM19 | $5.7 \times 10^5$ | $2.6 \times 10^{-3}$ | 4.5 |
| TAM22 | $7.3 \times 10^5$ | $3.5 \times 10^{-3}$ | 4.8 |

TABLE 9-continued

Biacore screening: Fabs ranked by KD
Ligand: PKA-phosphorylated Tau protein,
immobilized directly using amine coupling.
Analyte: Recombinant Fab

| | ka (1/Ms) | kd (1/s) | KD (nM) |
|---|---|---|---|
| TAM20 | $6.8 \times 10^5$ | $3.6 \times 10^{-3}$ | 5.2 |
| TAM9 | $3.3 \times 10^5$ | $1.9 \times 10^{-3}$ | 5.7 |
| TAM2 | $3.5 \times 10^5$ | $2.4 \times 10^{-3}$ | 6.7 |
| TAM3 | $3.0 \times 10^5$ | $2.1 \times 10^{-3}$ | 7 |
| TAM21 | $2.7 \times 10^5$ | $2.4 \times 10^{-3}$ | 9 |
| TAM6 | $2.8 \times 10^5$ | $2.7 \times 10^{-3}$ | 10 |
| TAM15 | $2.0 \times 10^5$ | $2.2 \times 10^{-3}$ | 11 |
| TAM11 | $2.2 \times 10^5$ | $2.5 \times 10^{-3}$ | 11 |
| TAM4 | $2.4 \times 10^5$ | $2.8 \times 10^{-3}$ | 12 |
| TAM13 | $1.9 \times 10^5$ | $2.3 \times 10^{-3}$ | 12 |
| TAM17 | $2.2 \times 10^5$ | $2.9 \times 10^{-3}$ | 13 |
| TAM10 | $6.6 \times 10^5$ | $10.3 \times 10^{-3}$ | 16 |
| TAM12 | $1.6 \times 10^5$ | $2.6 \times 10^{-3}$ | 16 |
| TAM16 | $1.5 \times 10^5$ | $2.4 \times 10^{-3}$ | 17 |
| TAM14 | $1.2 \times 10^5$ | $2.0 \times 10^{-3}$ | 17 |
| TAM5 | $1.9 \times 10^5$ | $3.3 \times 10^{-3}$ | 17 |
| TAM23 | $16.5 \times 10^5$ | $33.4 \times 10^{-3}$ | 20 |
| TAM18 | $1.3 \times 10^5$ | $2.9 \times 10^{-3}$ | 23 |
| TAM7 | $5.4 \times 10^5$ | $13.9 \times 10^{-3}$ | 26 |
| 5202.4 | $1.4 \times 10^5$ | $9.0 \times 10^{-3}$ | 62 |
| TAM8 | $0.3 \times 10^5$ | $7.2 \times 10^{-3}$ | 275 |

TABLE 10

Binding kinetics of selected affinity-matured variants of 5202.4 (Fab format) to PKA-phosphorylated Tau protein in Biacore: monovalent interaction

| | $k_a$ (M$^{-1}$s$^{-1}$) | | $k_d$ (s$^{-1}$) | | Rmax (RU) | | $K_D$ (nM) | |
|---|---|---|---|---|---|---|---|---|
| Fab | Expt1 | Expt2 | Expt1 | Expt2 | Expt1 | Expt2 | Expt1 | Expt2 |
| 5202.4 | $2 \times 10^5$ | $1 \times 10^5$ | $10 \times 10^{-3}$ | $10 \times 10^{-3}$ | 113 | 77 | 50 | 74 |
| TAM1 | $7 \times 10^5$ | $10 \times 10^5$ | $1 \times 10^{-3}$ | $2 \times 10^{-3}$ | 130 | 91 | 2 | 2 |
| TAM2 | $4 \times 10^5$ | $6 \times 10^5$ | $2 \times 10^{-3}$ | $3 \times 10^{-3}$ | 113 | 75 | 5 | 5 |
| TAM9 | $5 \times 10^5$ | $5 \times 10^5$ | $2 \times 10^{-3}$ | $3 \times 10^{-3}$ | 119 | 85 | 4 | 5 |
| TAM19 | $7 \times 10^5$ | $9 \times 10^5$ | $2 \times 10^{-3}$ | $3 \times 10^{-3}$ | 121 | 87 | 4 | 4 |
| TAM20 | $9 \times 10^5$ | $10 \times 10^5$ | $4 \times 10^{-3}$ | $5 \times 10^{-3}$ | 118 | 85 | 4 | 5 |
| TAM1 (repeat) | $6 \times 10^5$ | $10 \times 10^5$ | $1 \times 10^{-3}$ | $2 \times 10^{-3}$ | 128 | 94 | 2 | 2 |

TABLE 11

Binding kinetics of selected affinity-matured variants of 5202.4 (IgG format) to PKA-phosphorylated Tau protein

| | $k_a$ (M$^{-1}$s$^{-1}$) | | $k_d$ (s$^{-1}$) | | Rmax (RU) | | $K_D$ (nM) | |
|---|---|---|---|---|---|---|---|---|
| IgG | Ligand density 1 | Ligand density 2 | Ligand density 1 | Ligand density 2 | Ligand density 1 | Ligand density 2 | Ligand density 1 | Ligand density 2 |
| 5202.4 | $6 \times 10^5$ | $4 \times 10^5$ | $7 \times 10^{-4}$ | $2 \times 10^{-4}$ | 28 | 265 | 1.2 | 0.6 |
| TAM1 | $56 \times 10^5$ | $17 \times 10^5$ | $11 \times 10^{-4}$ | $4 \times 10^{-4}$ | 52 | 367 | 0.2 | 0.2 |
| TAM2 | $35 \times 10^5$ | $11 \times 10^5$ | $11 \times 10^{-4}$ | $3 \times 10^{-4}$ | 44 | 364 | 0.3 | 0.2 |
| TAM9 | $28 \times 10^5$ | $14 \times 10^5$ | $20 \times 10^{-4}$ | $6 \times 10^{-4}$ | 50 | 304 | 0.7 | 0.4 |
| TAM19 | $35 \times 10^5$ | $14 \times 10^5$ | $8 \times 10^{-4}$ | $5 \times 10^{-4}$ | 65 | 363 | 0.2 | 0.4* |
| TAM20 | $16 \times 10^5$ | $16 \times 10^5$ | $12 \times 10^{-4}$ | $3 \times 10^{-4}$ | 80 | 368 | 0.8 | 0.2 |

Concentrations tested: 25 nM, 6.25 nM, 1.56 nM, 1.56 nM, 0.4 nM, 0.1 nM. Quality control: 25 nM data excluded where negative association phase and/or non-specific binding greater than approximately 10% of the Rmax was observed (TAM1 & 2, both densities; TAM19, density 1). One curve (TAM20, 1.25 nM) was excluded due to a positive slope in the dissociation phase. Asterix (*) indicates Chi2 approx 21% Rmax. Note suboptimal 1:1 fitting may be expected for bivalent IgG binding to an immobilized antigen.

TABLE 12

Longest isoform of human Tau (441 aa), also called Tau40

| | |
|---|---|
| Longest isoform of human Tau (441aa), also called Tau40 Microtubule-associated protein tau isoform 2 [Homo sapiens] NCBI Reference Sequence: NP_005901.2 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQARMVSK SKDGTGSDDK KAKGADGKTK IATPRGAAPP GQKGQANATR IPAKTPPAPK |

TABLE 12-continued

Longest isoform of human Tau (441 aa), also called Tau40

| |
|---|
| TPPSSGEPPK SGDRSGYSSP GSPGTPGSRS RTPSLPTPPT REPKKVAVVR TPPKSPSSAK SRLQTAPVPM PDLKNVKSKI GSTENLKHQP GGGKVQIINK KLDLSNVQSK CGSKDNIKHV PGGGSVQIVY KPVDLSKVTS KCGSLGNIHH KPGGGQVEVK SEKLDFKDRV QSKIGSLDNI THVPGGGNKK IETHKLTFRE NAKAKTDHGA EIVYKSPVVS GDTSPRHLSN VSSTGSIDMV DSPQLATLAD EVSASLAKQG L (SEQ ID NO: 59) |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that binds to a phosphorylated epitope of Tau protein, wherein the antibody comprises HVR-L1, HVR-L2 and HVR-L3, wherein:
   (a) HVR-L1 comprises the amino acid sequence $X_1SSQX_2LX_3X_4X_5X_6GX_7TYX_8H$ (SEQ ID NO:89), wherein $X_1$=R or T; $X_2$=S, R or V; $X_3$=V, I or R; $X_4$=H or R; $X_5$=S, R, G or K; $X_6$=H, N, R, K or G; $X_7$=K or R; and $X_8$=L or V;
   (b) HVR-L2 comprises the amino acid sequence $KVX_9X_{10}RFX_{11}$ (SEQ ID NO:90), wherein $X_9$=S, K or R; $X_{10}$=N, K or H; and $X_{11}$=S, F, G, K, R, Y or L; and
   (c) HVR-L3 comprises the amino acid sequence $SQTX_{12}X_{13}FPX_{14}T$ (SEQ ID NO:91), wherein $X_{12}$=A or R; $X_{13}$=H, R, Q or Y; $X_{14}$=Y or R;
   and wherein the antibody does not comprise an HVR-L1, HVR-L2 and HVR-L3 wherein the HVR-L1 amino acid sequence is RSSQSLVHSHGKTYLH (SEQ ID NO:15) or RSSQRLVHSHGKTYLH (SEQ ID NO:92); the HVR-L2 amino acid sequence is KVSNRFS (SEQ ID NO:16); and the HVR-L3 amino acid sequence is SQTAHFPYT (SEQ ID NO:30).

2. The antibody of claim 1, wherein the phosphorylated epitope includes a phosphorylated amino acid residue selected from the group consisting of serine at position 409 of human tau (SEQ ID NO:59); serine at position 404 of human tau (SEQ ID NO:59); and serine at position 404 and 409 of human tau (SEQ ID NO:59).

3. The antibody of claim 1, wherein the antibody comprises HVR-H1, HVR-H2 and HVR-H3, wherein HVR-H1 comprises the amino acid sequence GYTFTDYYMN (SEQ ID NO:33); HVR-H2 comprises the amino acid sequence DINPNRGGTTYNQKFKG (SEQ ID NO:34); and HVR-H3 comprises the amino acid sequence YYAVGY (SEQ ID NO:35).

4. The antibody of claim 1, wherein the antibody comprises an HVR-L1, HVR-L2 and HVR-L3, wherein (a) HVR-L1 comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14; (b) HVR-L2 comprises the amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO: 26; and (c) HVR-L3 comprises the amino acid sequence selected from the group consisting of SEQ ID NO:27, SEQ ID NO:28, SEQ ID NO:29, SEQ ID NO:30, SEQ ID NO:31, and SEQ ID NO:32.

5. The antibody of claim 4, comprising:
(a)(i) HVR-L1 comprising the amino acid sequence of SEQ ID NO:1; (ii) HVR-L2 comprising the amino acid sequence of SEQ ID NO:16; and (iii) HVR-L3 comprising the amino acid sequence of SEQ ID NO:27; or
(b)(i) HVR-L1 comprising the amino acid sequence of SEQ ID NO:2; (ii) HVR-L2 comprising the amino acid sequence of SEQ ID NO:17; and (iii) HVR-L3 comprising the amino acid sequence of SEQ ID NO:27; or
(c)(i) HVR-L1 comprising the amino acid sequence of SEQ ID NO:8; (ii) HVR-L2 comprising the amino acid sequence of SEQ ID NO:21; and (iii) HVR-L3 comprising the amino acid sequence of SEQ ID NO:29; or
(d)(i) HVR-L1 comprising the amino acid sequence of SEQ ID NO:14; (ii) HVR-L2 comprising the amino acid sequence of SEQ ID NO:25; and (iii) HVR-L3 comprising the amino acid sequence of SEQ ID NO:31; or
(e)(i) HVR-L1 comprising the amino acid sequence of SEQ ID NO:9; (ii) HVR-L2 comprising the amino acid sequence of SEQ ID NO:17; and (iii) HVR-L3 comprising the amino acid sequence of SEQ ID NO:31.

6. The antibody of claim 4, comprising a light chain variable domain (VL) sequence selected from the group consisting of SEQ ID NO:36, SEQ ID NO:37, SEQ ID NO:44, SEQ ID NO:54, and SEQ ID NO:55, or a VL having at least 95% sequence identity to the amino acid sequence selected from the group consisting of SEQ ID NO:36, SEQ ID NO:37, SEQ ID NO:44, SEQ ID NO:54, and SEQ ID NO:55.

7. The antibody of claim 6, further comprising a heavy chain variable domain (VH) sequence of SEQ ID NO:58, or a VH sequence having at least 95% sequence identity to the amino acid sequence of SEQ ID NO:58.

8. The antibody of claim 1, which is a monoclonal antibody.

9. The antibody of claim 1, which is a human, humanized, or chimeric antibody.

10. The antibody of claim 9, which is a human or humanized antibody.

11. The antibody of claim 1, which is a full length IgG1 antibody or a full-length IgG4 antibody.

12. The antibody of claim 1, which is a full length IgG1 N297G antibody.

13. The antibody of claim 1, wherein the Tau protein is a human Tau protein.

14. The antibody of claim 1, which does not bind to the same epitope of the Tau protein which is not phosphorylated, or which binds to the same epitope of the Tau protein which is not phosphorylated with substantially reduced affinity.

15. The antibody of claim 1, wherein the Tau protein comprises the amino acid sequence of SEQ ID NO:59.

16. The antibody of claim 13, wherein the epitope on the human Tau protein comprises amino acid residues 404-411.

17. The antibody of claim 1, which binds to the phosphorylated epitope with a Kd of between about 1 nM and 45 nM.

18. The antibody of claim 1, which binds to the phosphorylated epitope with a Kd of ≤1 nM.

19. The antibody of claim 1, which has a dissociation rate constant of $\leq 5 \times 10^{-3} s^{-1}$.

20. The antibody of claim 1, which has an association rate constant of $\geq 3 \times 10^5 M^{-1} s^{-1}$ or $\geq 7 \times 10^5 M^{-1} s^{-1}$.

21. The antibody of claim 1, wherein the Tau protein is an aggregated microtubule-associated and/or hyperphosphorylated Tau protein.

22. An isolated nucleic acid encoding the antibody of claim 1.

23. A host cell comprising the nucleic acid of claim 22.

24. A method of producing an antibody comprising culturing the host cell of claim 23 so that the antibody is produced.

25. An immunoconjugate comprising the antibody of claim 1 and a cytotoxic agent.

26. A pharmaceutical formulation comprising the antibody of claim 1 and a pharmaceutically acceptable carrier.

27. A method of treating an individual having a disease or disorder selected from: a tauopathy, Alzheimer's disease (AD), frontotemporal dementia (FTD), and a Tau protein associated impairment in or loss of cognitive functions, comprising administering to the individual an effective amount of the antibody of claim 1.

28. A method of reducing the levels of total Tau protein, phosphorylated Tau protein or hyperphosphorylated Tau protein in the brain of an individual, comprising administering to the individual an effective amount of the antibody of claim 1 to reduce the levels of total Tau protein, phosphorylated Tau protein or hyperphosphorylated Tau protein in the brain of the individual.

29. The method of claim 27, wherein the phosphorylated epitope includes a phosphorylated amino acid residue selected from the group consisting of serine at position 409 of human tau (SEQ ID NO:59); serine at position 404 of human tau (SEQ ID NO:59); and serine at position 404 and 409 of human tau (SEQ ID NO:59).

30. The method of claim 27, wherein the antibody comprises at least one sequence selected from the group consisting of HVR-H1, HVR-H2 and HVR-H3, wherein HVR-H1 comprises the amino acid sequence GYTFTDYYMN (SEQ ID NO:33); HVR-H2 comprises the amino acid sequence DINPNRGGTTYNQKFKG (SEQ ID NO:34); and HVR-H3 comprises the amino acid sequence YYAVGY (SEQ ID NO:35).

31. The method of claim 27, wherein the antibody comprises an HVR-L1, HVR-L2 and HVR-L3, wherein (a) HVR-L1 comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14; (b) HVR-L2 comprises the amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO: 26; and (c) HVR-L3 comprises the amino acid sequence selected from the group consisting of SEQ ID NO:27, SEQ ID NO:28, SEQ ID NO:29, SEQ ID NO:30, SEQ ID NO:31, and SEQ ID NO:32.

32. The method of claim 31, wherein the antibody comprises:
(a)(i) HVR-L1 comprising the amino acid sequence of SEQ ID NO:1; (ii) HVR-L2 comprising the amino acid sequence of SEQ ID NO:16; and (iii) HVR-L3 comprising the amino acid sequence of SEQ ID NO:27; or (b)(i) HVR-L1 comprising the amino acid sequence of SEQ ID NO:2; (ii) HVR-L2 comprising the amino acid sequence of SEQ ID NO:17; and (iii) HVR-L3 comprising the amino acid sequence of SEQ ID NO:27; or (c)(i) HVR-L1 comprising the amino acid sequence of SEQ ID NO:8; (ii) HVR-L2 comprising the amino acid sequence of SEQ ID NO:21; and (iii) HVR-L3 comprising the amino acid sequence of SEQ ID NO:29; or (d)(i) HVR-L1 comprising the amino acid sequence of SEQ ID NO:14; (ii) HVR-L2 comprising the amino acid sequence of SEQ ID NO:25; and (iii) HVR-L3 comprising the amino acid sequence of SEQ ID NO:31; or (e)(i) HVR-L1 comprising the amino acid sequence of SEQ ID NO:9; (ii) HVR-L2 comprising the amino acid sequence of SEQ ID NO:17; and (iii) HVR-L3 comprising the amino acid sequence of SEQ ID NO:31.

33. The method of claim 31, wherein the antibody comprises a light chain variable domain (VL) sequence selected from the group consisting of SEQ ID NO:36, SEQ ID NO:37, SEQ ID NO:44, SEQ ID NO:54, and SEQ ID NO:55, or a VL having at least 95% sequence identity to the amino acid sequence selected from the group consisting of SEQ ID NO:36, SEQ ID NO:37, SEQ ID NO:44, SEQ ID NO:54, and SEQ ID NO:55.

34. The method of claim 33, wherein the antibody further comprises a heavy chain variable domain (VH) sequence of SEQ ID NO:58, or a VH sequence having at least 95% sequence identity to the amino acid sequence of SEQ ID NO:58.

35. The method of claim 27, wherein the antibody is a monoclonal antibody.

36. The method of claim 35, wherein the antibody is a human, humanized, or chimeric antibody.

37. The method of claim 35, wherein the antibody is a full length IgG1 antibody or a full-length IgG4 antibody.

38. The method of claim 35, wherein the antibody is a full length IgG1 N297G antibody.

39. The method of claim 27, wherein the antibody binds to human Tau protein.

40. The method of claim 39, wherein the antibody does not bind to the same epitope of the Tau protein which is not phosphorylated, or which binds to the same epitope of the Tau protein which is not phosphorylated with substantially reduced affinity.

41. The method of claim 39, wherein the Tau protein comprises the amino acid sequence of SEQ ID NO:59.

42. The method of claim 39, wherein the epitope on the human Tau protein comprises amino acid residues 404-411.

43. The method of claim 27, wherein the antibody binds to the phosphorylated epitope with a Kd of between about 1 nM and 45 nM.

44. The method of claim 27, wherein the antibody binds to the phosphorylated epitope with a Kd of ≤1 nM.

45. The method of claim 27, wherein the antibody has a dissociation rate constant of $\leq 5\times10^{-3}s^{-1}$.

46. The method of claim 27, wherein the antibody has an association rate constant of $\geq 3\times10^{5}M^{-1}s^{-1}$ or $\geq 7\times10^{5}M^{-1}s^{-1}$.

47. The method of claim 27, wherein the antibody binds to a Tau protein that is an aggregated microtubule-associated and/or hyperphosphorylated Tau protein.

48. The method of claim 28, wherein the phosphorylated epitope includes a phosphorylated amino acid residue selected from the group consisting of serine at position 409 of human tau (SEQ ID NO:59); serine at position 404 of human tau (SEQ ID NO:59); and serine at position 404 and 409 of human tau (SEQ ID NO:59).

49. The method of claim 28, wherein the antibody comprises at least one sequence selected from the group consisting of HVR-H1, HVR-H2 and HVR-H3, wherein HVR-H1 comprises the amino acid sequence GYTFTDYYMN (SEQ ID NO:33); HVR-H2 comprises the amino acid sequence DINPNRGGTTYNQKFKG (SEQ ID NO:34); and HVR-H3 comprises the amino acid sequence YYAVGY (SEQ ID NO:35).

50. The method of claim 28, wherein the antibody comprises an HVR-L1, HVR-L2 and HVR-L3, wherein (a) HVR-L1 comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14; (b) HVR-L2 comprises the amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO: 26; and (c) HVR-L3 comprises the amino acid sequence selected from the group consisting of SEQ ID NO:27, SEQ ID NO:28, SEQ ID NO:29, SEQ ID NO:30, SEQ ID NO:31, and SEQ ID NO:32.

51. The method of claim 50, wherein the antibody comprises:

(a)(i) HVR-L1 comprising the amino acid sequence of SEQ ID NO:1; (ii) HVR-L2 comprising the amino acid sequence of SEQ ID NO:16; and (iii) HVR-L3 comprising the amino acid sequence of SEQ ID NO:27; or (b)(i) HVR-L1 comprising the amino acid sequence of SEQ ID NO:2; (ii) HVR-L2 comprising the amino acid sequence of SEQ ID NO:17; and (iii) HVR-L3 comprising the amino acid sequence of SEQ ID NO:27; or (c)(i) HVR-L1 comprising the amino acid sequence of SEQ ID NO:8; (ii) HVR-L2 comprising the amino acid sequence of SEQ ID NO:21; and (iii) HVR-L3 comprising the amino acid sequence of SEQ ID NO:29; or (d)(i) HVR-L1 comprising the amino acid sequence of SEQ ID NO:14; (ii) HVR-L2 comprising the amino acid sequence of SEQ ID NO:25; and (iii) HVR-L3 comprising the amino acid sequence of SEQ ID NO:31; or (e)(i) HVR-L1 comprising the amino acid sequence of SEQ ID NO:9; (ii) HVR-L2 comprising the amino acid sequence of SEQ ID NO:17; and (iii) HVR-L3 comprising the amino acid sequence of SEQ ID NO:31.

52. The method of claim 50, wherein the antibody comprises a light chain variable domain (VL) sequence selected from the group consisting of SEQ ID NO:36, SEQ ID NO:37, SEQ ID NO:44, SEQ ID NO:54, and SEQ ID NO:55, or a VL having at least 95% sequence identity to the amino acid sequence selected from the group consisting of SEQ ID NO:36, SEQ ID NO:37, SEQ ID NO:44, SEQ ID NO:54, and SEQ ID NO:55.

53. The method of claim 52, wherein the antibody further comprises a heavy chain variable domain (VH) sequence of SEQ ID NO:58, or a VH sequence having at least 95% sequence identity to the amino acid sequence of SEQ ID NO:58.

54. The method of claim 28, wherein the antibody is a monoclonal antibody.

55. The method of claim 54, wherein the antibody is a human, humanized, or chimeric antibody.

56. The method of claim 54, wherein the antibody is a full length IgG1 antibody or a full-length IgG4 antibody.

57. The method of claim 54, wherein the antibody is a full length IgG1 N297G antibody.

58. The method of claim 28, wherein the antibody binds to human Tau protein.

59. The method of claim 58, wherein the antibody does not bind to the same epitope of the Tau protein which is not phosphorylated, or which binds to the same epitope of the Tau protein which is not phosphorylated with substantially reduced affinity.

60. The method of claim 58, wherein the Tau protein comprises the amino acid sequence of SEQ ID NO:59.

61. The method of claim 58, wherein the epitope on the human Tau protein comprises amino acid residues 404-411.

62. The method of claim 28, wherein the antibody binds to the phosphorylated epitope with a Kd of between about 1 nM and 45 nM.

63. The method of claim 28, wherein the antibody binds to the phosphorylated epitope with a Kd of ≤1 nM.

64. The method of claim 28, wherein the antibody has a dissociation rate constant of $\leq 5 \times 10^{-3} s^{-1}$.

65. The method of claim 28, wherein the antibody has an association rate constant of $\geq 3 \times 10^5 M^{-1} s^{-1}$ or $\geq 7 \times 10^5 M^{-1} s^{-1}$.

66. The method of claim 28, wherein the antibody binds to a Tau protein that is an aggregated microtubule-associated and/or hyperphosphorylated Tau protein.

\* \* \* \* \*

SEQUENCE LISTING

```
<160> NUMBER OF SEQ ID NOS: 97

<210> SEQ ID NO 1
<211> LENGTH: 16
<212> TYPE: PRT
<213> ORGANISM: Artificial sequence
<220> FEATURE:
<223> OTHER INFORMATION: Synthetic

<400> SEQUENCE: 1

Arg Ser Ser Gln Ser Leu Val His Arg Asn Gly Lys Thr Tyr Leu His
1               5                   10                  15

<210> SEQ ID NO 2
<211> LENGTH: 16
<212> TYPE: PRT
<213> ORGANISM: Artificial sequence
<220> FEATURE:
<223> OTHER INFORMATION: Synthetic

<400> SEQUENCE: 2

Arg Ser Ser Gln Ser Leu Val His Ser Arg Gly Lys Thr Tyr Leu His
1               5                   10                  15

<210> SEQ ID NO 3
<211> LENGTH: 16
<212> TYPE: PRT
<213> ORGANISM: Artificial sequence
<220> FEATURE:
<223> OTHER INFORMATION: Synthetic

<400> SEQUENCE: 3

Arg Ser Ser Gln Ser Leu Val His Ser Lys Gly Lys Thr Tyr Leu His
1               5                   10                  15

<210> SEQ ID NO 4
<211> LENGTH: 16
<212> TYPE: PRT
<213> ORGANISM: Artificial sequence
<220> FEATURE:
<223> OTHER INFORMATION: Synthetic
```

```
<400> SEQUENCE: 4

Arg Ser Ser Gln Ser Leu Val Arg Ser Arg Gly Lys Thr Tyr Leu His
1               5                   10                  15

<210> SEQ ID NO 5
<211> LENGTH: 16
<212> TYPE: PRT
<213> ORGANISM: Artificial sequence
<220> FEATURE:
<223> OTHER INFORMATION: Synthetic

<400> SEQUENCE: 5

Arg Ser Ser Gln Ser Leu Val His Lys His Gly Lys Thr Tyr Leu His
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: Synthetic

<400> SEQUENCE: 6

Arg Ser Ser Gln Ser Leu Val His Ser Gly Gly Lys Thr Tyr Leu His
1               5                   10                  15

<210> SEQ ID NO 7
<211> LENGTH: 16
<212> TYPE: PRT
<213> ORGANISM: Artificial sequence
<220> FEATURE:
<223> OTHER INFORMATION: Synthetic

<400> SEQUENCE: 7

Arg Ser Ser Gln Arg Leu Ile His Arg Asn Gly Lys Thr Tyr Leu His
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Synthetic

<400> SEQUENCE: 8

Arg Ser Ser Gln Ser Leu Val Arg Ser His Gly Lys Thr Tyr Leu His
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: Synthetic

<400> SEQUENCE: 9

Arg Ser Ser Gln Ser Leu Val His Ser His Gly Arg Thr Tyr Leu His
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: Synthetic

<400> SEQUENCE: 10
```

```
Thr Ser Ser Gln Val Leu Val His Ser His Gly Lys Thr Tyr Leu His
1               5                   10                  15
```

<210> SEQ ID NO 11
<211> LENGTH: 16
<212> TYPE: PRT
<213> ORGANISM: Artificial sequence
<220> FEATURE:
<223> OTHER INFORMATION: Synthetic

<400> SEQUENCE: 11

```
Arg Ser Ser Gln Ser Leu Val His Arg His Gly Lys Thr Tyr Leu His
1               5                   10                  15
```

<210> SEQ ID NO 12
<211> LENGTH: 16
<212> TYPE: PRT
<213> ORGANISM: Artificial sequence
<220> FEATURE:
<223> OTHER INFORMATION: Synthetic

<400> SEQUENCE: 12

```
Arg Ser Ser Gln Ser Leu Val His Arg Arg Gly Lys Thr Tyr Val His
1               5                   10                  15
```

<210> SEQ ID NO 13
<211> LENGTH: 16
<212> TYPE: PRT
<213> ORGANISM: Artificial sequence
<220> FEATURE:
<223> OTHER INFORMATION: Synthetic

<400> SEQUENCE: 13

```
Arg Ser Ser Gln Ser Leu Val His Gly His Gly Lys Thr Tyr Leu His
1               5                   10                  15
```

<210> SEQ ID NO 14
<211> LENGTH: 16
<212> TYPE: PRT
<213> ORGANISM: Artificial sequence
<220> FEATURE:
<223> OTHER INFORMATION: Synthetic

<400> SEQUENCE: 14

```
Arg Ser Ser Gln Ser Leu Arg His Ser His Gly Lys Thr Tyr Leu His
1               5                   10                  15
```

<210> SEQ ID NO 15
<211> LENGTH: 16
<212> TYPE: PRT
<213> ORGANISM: Artificial sequence
<220> FEATURE:
<223> OTHER INFORMATION: Synthetic

<400> SEQUENCE: 15

```
Arg Ser Ser Gln Ser Leu Val His Ser His Gly Lys Thr Tyr Leu His
1               5                   10                  15
```

<210> SEQ ID NO 16
<211> LENGTH: 7
<212> TYPE: PRT
<213> ORGANISM: Artificial sequence
<220> FEATURE:
<223> OTHER INFORMATION: Synthetic

<400> SEQUENCE: 16

Lys Val Ser Asn Arg Phe Ser
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic

<400> SEQUENCE: 17

Lys Val Ser Asn Arg Phe Phe
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic

<400> SEQUENCE: 18

Lys Val Lys Asn Arg Phe Ser
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic

<400> SEQUENCE: 19

Lys Val Arg Asn Arg Phe Ser
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic

<400> SEQUENCE: 20

Lys Val Ser Asn Arg Phe Gly
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic

<400> SEQUENCE: 21

Lys Val Ser Asn Arg Phe Lys
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic

<400> SEQUENCE: 22

Lys Val Ser Asn Arg Phe Arg

```
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic

<400> SEQUENCE: 23

Lys Val Ser Lys Arg Phe Tyr
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic

<400> SEQUENCE: 24

Lys Val Arg Asn Arg Phe Ser
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic

<400> SEQUENCE: 25

Lys Val Ser His Arg Phe Ser
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic

<400> SEQUENCE: 26

Lys Val Ser Asn Arg Phe Leu
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic

<400> SEQUENCE: 27

Ser Gln Thr Ala Arg Phe Pro Tyr Thr
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic

<400> SEQUENCE: 28

Ser Gln Thr Ala His Phe Pro Arg Thr
1               5
```

<210> SEQ ID NO 29
<211> LENGTH: 9
<212> TYPE: PRT
<213> ORGANISM: Artificial sequence
<220> FEATURE:
<223> OTHER INFORMATION: Synthetic

<400> SEQUENCE: 29

Ser Gln Thr Ala Gln Phe Pro Tyr Thr
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic

<400> SEQUENCE: 30

Ser Gln Thr Ala His Phe Pro Tyr Thr
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic

<400> SEQUENCE: 31

Ser Gln Thr Arg His Phe Pro Tyr Thr
1               5

<210> SEQ ID NO 32
<211> LENGTH: 9
<212> TYPE: PRT
<213> ORGANISM: Artificial sequence
<220> FEATURE:
<223> OTHER INFORMATION: Synthetic

<400> SEQUENCE: 32

Ser Gln Thr Ala Tyr Phe Pro Tyr Thr
1               5

<210> SEQ ID NO 33
<211> LENGTH: 10
<212> TYPE: PRT
<213> ORGANISM: Artificial sequence
<220> FEATURE:
<223> OTHER INFORMATION: Synthetic

<400> SEQUENCE: 33

Gly Tyr Thr Phe Thr Asp Tyr Tyr Met Asn
1               5                   10

<210> SEQ ID NO 34
<211> LENGTH: 17
<212> TYPE: PRT
<213> ORGANISM: Artificial sequence
<220> FEATURE:
<223> OTHER INFORMATION: Synthetic

<400> SEQUENCE: 34

Asp Ile Asn Pro Asn Arg Gly Gly Thr Thr Tyr Asn Gln Lys Phe Lys
1               5                   10                  15

Gly

<210> SEQ ID NO 35
<211> LENGTH: 6
<212> TYPE: PRT
<213> ORGANISM: Artificial sequence
<220> FEATURE:
<223> OTHER INFORMATION: Synthetic

<400> SEQUENCE: 35

Tyr Tyr Ala Val Gly Tyr
1               5

<210> SEQ ID NO 36
<211> LENGTH: 112
<212> TYPE: PRT
<213> ORGANISM: Artificial sequence
<220> FEATURE:
<223> OTHER INFORMATION: Synthetic

<400> SEQUENCE: 36

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Arg Phe Pro Tyr Thr Phe Gly Gly Gly Thr Lys Val Glu Ile Lys
            100                 105                 110

<210> SEQ ID NO 37
<211> LENGTH: 112
<212> TYPE: PRT
<213> ORGANISM: Artificial sequence
<220> FEATURE:
<223> OTHER INFORMATION: Synthetic

<400> SEQUENCE: 37

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Arg Phe Pro Tyr Thr Phe Gly Gly Gly Thr Lys Val Glu Ile Lys
            100                 105                 110

<210> SEQ ID NO 38

<211> LENGTH: 112
<212> TYPE: PRT
<213> ORGANISM: Artificial sequence
<220> FEATURE:
<223> OTHER INFORMATION: Synthetic

<400> SEQUENCE: 38

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Lys Gly Lys Thr Tyr Leu His Trp Tyr Leu Gln Lys Pro Gly Gln Ser
        35                  40                  45

Pro Gln Leu Leu Ile Tyr Lys Val Lys Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Arg Thr Phe Gly Gly Gly Thr Lys Val Glu Ile Lys
            100                 105                 110
```

<210> SEQ ID NO 39
<211> LENGTH: 112
<212> TYPE: PRT
<213> ORGANISM: Artificial sequence
<220> FEATURE:
<223> OTHER INFORMATION: Synthetic

<400> SEQUENCE: 39

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Gln Phe Pro Tyr Thr Phe Gly Gly Gly Thr Lys Val Glu Ile Lys
            100                 105                 110
```

<210> SEQ ID NO 40
<211> LENGTH: 112
<212> TYPE: PRT
<213> ORGANISM: Artificial sequence
<220> FEATURE:
<223> OTHER INFORMATION: Synthetic

<400> SEQUENCE: 40

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Lys
            20                  25                  30

His Gly Lys Thr Tyr Leu His Trp Tyr Leu Gln Lys Pro Gly Gln Ser
        35                  40                  45
```

```
Pro Gln Leu Leu Ile Tyr Lys Val Arg Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Ala His Phe Pro Tyr Thr Phe Gly Gly Gly Thr Lys Val Glu Ile Lys
                100                 105                 110
```

<210> SEQ ID NO 41
<211> LENGTH: 112
<212> TYPE: PRT
<213> ORGANISM: Artificial sequence
<220> FEATURE:
<223> OTHER INFORMATION: Synthetic

<400> SEQUENCE: 41

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Gly Gly Lys Thr Tyr Leu His Trp Tyr Leu Gln Lys Pro Gly Gln Ser
             35                  40                  45

Pro Gln Leu Leu Ile Tyr Lys Val Ser Asn Arg Phe Gly Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Arg His Phe Pro Tyr Thr Phe Gly Gly Gly Thr Lys Val Glu Ile Lys
                100                 105                 110
```

<210> SEQ ID NO 42
<211> LENGTH: 112
<212> TYPE: PRT
<213> ORGANISM: Artificial sequence
<220> FEATURE:
<223> OTHER INFORMATION: Synthetic

<400> SEQUENCE: 42

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Arg Leu Ile His Arg
                 20                  25                  30

Asn Gly Lys Thr Tyr Leu His Trp Tyr Leu Gln Lys Pro Gly Gln Ser
             35                  40                  45

Pro Gln Leu Leu Ile Tyr Lys Val Ser Asn Arg Phe Phe Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Ala His Phe Pro Tyr Thr Phe Gly Gly Gly Thr Lys Val Glu Ile Lys
                100                 105                 110
```

<210> SEQ ID NO 43
<211> LENGTH: 112
<212> TYPE: PRT
<213> ORGANISM: Artificial sequence

```
<220> FEATURE:
<223> OTHER INFORMATION: Synthetic

<400> SEQUENCE: 43

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Tyr Phe Pro Tyr Thr Phe Gly Gly Gly Thr Lys Val Glu Ile Lys
            100                 105                 110

<210> SEQ ID NO 44
<211> LENGTH: 112
<212> TYPE: PRT
<213> ORGANISM: Artificial sequence
<220> FEATURE:
<223> OTHER INFORMATION: Synthetic

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Lys Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Gln Phe Pro Tyr Thr Phe Gly Gly Gly Thr Lys Val Glu Ile Lys
            100                 105                 110

<210> SEQ ID NO 45
<211> LENGTH: 112
<212> TYPE: PRT
<213> ORGANISM: Artificial sequence
<220> FEATURE:
<223> OTHER INFORMATION: Synthetic

<400> SEQUENCE: 45

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110
```

<210> SEQ ID NO 46
<211> LENGTH: 112
<212> TYPE: PRT
<213> ORGANISM: Artificial sequence
<220> FEATURE:
<223> OTHER INFORMATION: Synthetic

<400> SEQUENCE: 46

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

His Gly Arg Thr Tyr Leu His Trp Tyr Leu Gln Lys Pro Gly Gln Ser
            35                  40                  45

Pro Gln Leu Leu Ile Tyr Lys Val Ser Asn Arg Phe Arg Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Tyr Phe Pro Tyr Thr Phe Gly Gly Gly Thr Lys Val Glu Ile Lys
            100                 105                 110
```

<210> SEQ ID NO 47
<211> LENGTH: 112
<212> TYPE: PRT
<213> ORGANISM: Artificial sequence
<220> FEATURE:
<223> OTHER INFORMATION: Synthetic

<400> SEQUENCE: 47

```
Asp Ile Val Met Thr Gln Thr Pro Leu Ser Leu Pro Val Thr Pro Gly
1               5                   10                  15

Glu Pro Ala Ser Ile Ser Cys Thr Ser Ser Gln Val Leu Val His Ser
                20                  25                  30

His Gly Lys Thr Tyr Leu His Trp Tyr Leu Gln Lys Pro Gly Gln Ser
            35                  40                  45

Pro Gln Leu Leu Ile Tyr Lys Val Ser Asn Arg Phe Arg Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Arg Phe Pro Tyr Thr Phe Gly Gly Gly Thr Lys Val Glu Ile Lys
            100                 105                 110
```

<210> SEQ ID NO 48
<211> LENGTH: 112
<212> TYPE: PRT
<213> ORGANISM: Artificial sequence
<220> FEATURE:
<223> OTHER INFORMATION: Synthetic

```
<400> SEQUENCE: 48

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Arg Thr Phe Gly Gly Gly Thr Lys Val Glu Ile Lys
            100                 105                 110

<210> SEQ ID NO 49
<211> LENGTH: 112
<212> TYPE: PRT
<213> ORGANISM: Artificial sequence
<220> FEATURE:
<223> OTHER INFORMATION: Synthetic

<400> SEQUENCE: 49

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Arg Gly Lys Thr Tyr Val His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

<210> SEQ ID NO 50
<211> LENGTH: 112
<212> TYPE: PRT
<213> ORGANISM: Artificial sequence
<220> FEATURE:
<223> OTHER INFORMATION: Synthetic

<400> SEQUENCE: 50

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Phe Cys Ser Gln Thr
            85                  90                  95

Ala His Phe Pro Tyr Thr Phe Gly Gly Gly Thr Lys Val Glu Ile Lys
            100                 105                 110

<210> SEQ ID NO 51
<211> LENGTH: 112
<212> TYPE: PRT
<213> ORGANISM: Artificial sequence
<220> FEATURE:
<223> OTHER INFORMATION: Synthetic

<400> SEQUENCE: 51

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
            85                  90                  95

Ala His Phe Pro Tyr Thr Phe Gly Gly Gly Thr Lys Val Glu Ile Lys
            100                 105                 110

<210> SEQ ID NO 52
<211> LENGTH: 112
<212> TYPE: PRT
<213> ORGANISM: Artificial sequence
<220> FEATURE:
<223> OTHER INFORMATION: Synthetic

<400> SEQUENCE: 52

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Gly
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Arg Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
            85                  90                  95

Ala His Phe Pro Tyr Thr Phe Gly Gly Gly Thr Lys Val Glu Ile Lys
            100                 105                 110

<210> SEQ ID NO 53
<211> LENGTH: 112
<212> TYPE: PRT
<213> ORGANISM: Artificial sequence
<220> FEATURE:
<223> OTHER INFORMATION: Synthetic

<400> SEQUENCE: 53

Asp Ile Val Met Thr Gln Thr Pro Leu Ser Leu Pro Val Thr Pro Gly
```

```
1               5                   10                  15
Glu Pro Ala Ser Ile Ser Cys Arg Ser Ser Gln Ser Leu Val His Gly
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Arg Phe Pro Tyr Thr Phe Gly Gly Gly Thr Lys Val Glu Ile Lys
            100                 105                 110

<210> SEQ ID NO 54
<211> LENGTH: 112
<212> TYPE: PRT
<213> ORGANISM: Artificial sequence
<220> FEATURE:
<223> OTHER INFORMATION: Synthetic

<400> SEQUENCE: 54

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Arg His Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Arg His Phe Pro Tyr Thr Phe Gly Gly Gly Thr Lys Val Glu Ile Lys
            100                 105                 110

<210> SEQ ID NO 55
<211> LENGTH: 112
<212> TYPE: PRT
<213> ORGANISM: Artificial sequence
<220> FEATURE:
<223> OTHER INFORMATION: Synthetic

<400> SEQUENCE: 55

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Arg Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95
```

Arg His Phe Pro Tyr Thr Phe Gly Gly Gly Thr Lys Val Glu Ile Lys
            100                 105                 110

<210> SEQ ID NO 56
<211> LENGTH: 112
<212> TYPE: PRT
<213> ORGANISM: Artificial sequence
<220> FEATURE:
<223> OTHER INFORMATION: Synthetic

<400> SEQUENCE: 56

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Leu Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

<210> SEQ ID NO 57
<211> LENGTH: 112
<212> TYPE: PRT
<213> ORGANISM: Artificial sequence
<220> FEATURE:
<223> OTHER INFORMATION: Synthetic

<400> SEQUENCE: 57

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Arg Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Arg His Phe Pro Tyr Thr Phe Gly Gly Gly Thr Lys Val Glu Ile Lys
            100                 105                 110

<210> SEQ ID NO 58
<211> LENGTH: 115
<212> TYPE: PRT
<213> ORGANISM: Artificial sequence
<220> FEATURE:
<223> OTHER INFORMATION: Synthetic

<400> SEQUENCE: 58

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr

```
            20                  25                  30
Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Tyr Tyr Ala Val Gly Tyr Trp Gly Gln Gly Thr Thr Val Thr
                100                 105                 110

Val Ser Ser
        115

<210> SEQ ID NO 59
<211> LENGTH: 441
<212> TYPE: PRT
<213> ORGANISM: Homo sapiens

<400> SEQUENCE: 59

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
        260                 265                 270
```

```
Gly Lys Val Gln Ile Ile Asn Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
        340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
        420                 425                 430

Ser Ala Ser Leu Ala Lys Gln Gly Leu
            435                 440

<210> SEQ ID NO 60
<211> LENGTH: 112
<212> TYPE: PRT
<213> ORGANISM: Artificial sequence
<220> FEATURE:
<223> OTHER INFORMATION: Synthetic

<400> SEQUENCE: 60

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

<210> SEQ ID NO 61
<211> LENGTH: 219
<212> TYPE: PRT
<213> ORGANISM: Artificial sequence
<220> FEATURE:
<223> OTHER INFORMATION: Synthetic

<400> SEQUENCE: 61

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30
```

-continued

His Gly Lys Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Ala His Phe Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215

<210> SEQ ID NO 62
<211> LENGTH: 115
<212> TYPE: PRT
<213> ORGANISM: Artificial sequence
<220> FEATURE:
<223> OTHER INFORMATION: Synthetic

<400> SEQUENCE: 62

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
         35                  40                  45

Gly Asp Ile Asn Pro Asn Arg Gly Gly Thr Thr Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Tyr Tyr Ala Val Gly Tyr Trp Gly Gln Gly Thr Thr Val Thr
                100                 105                 110

Val Ser Ser
        115

<210> SEQ ID NO 63
<211> LENGTH: 445
<212> TYPE: PRT
<213> ORGANISM: Artificial sequence
<220> FEATURE:
<223> OTHER INFORMATION: Synthetic

<400> SEQUENCE: 63

```
Glu Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Asp Tyr
            20                  25                  30
Tyr Met Asn Trp Val Arg Gln Ala Pro Gly Gln Gly Leu Glu Trp Ile
        35                  40                  45
Gly Asp Ile Asn Pro Asn Arg Gly Gly Thr Thr Tyr Asn Gln Lys Phe
    50                  55                  60
Lys Gly Arg Val Thr Ile Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser Tyr Tyr Ala Val Gly Tyr Trp Gly Gln Gly Thr Thr Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
```

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 64
<211> LENGTH: 219
<212> TYPE: PRT
<213> ORGANISM: Artificial sequence
<220> FEATURE:
<223> OTHER INFORMATION: Synthetic

<400> SEQUENCE: 64

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Arg Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 65
<211> LENGTH: 219
<212> TYPE: PRT
<213> ORGANISM: Artificial sequence
<220> FEATURE:
<223> OTHER INFORMATION: Synthetic

<400> SEQUENCE: 65

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Ala Arg Phe Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 66
<211> LENGTH: 219
<212> TYPE: PRT
<213> ORGANISM: Artificial sequence
<220> FEATURE:
<223> OTHER INFORMATION: Synthetic

<400> SEQUENCE: 66

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Lys Gly Lys Thr Tyr Leu His Trp Tyr Leu Gln Lys Pro Gly Gln Ser
         35                  40                  45

Pro Gln Leu Leu Ile Tyr Lys Val Lys Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Ala His Phe Pro Arg Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
                    195                 200                 205

Pro Val Thr Lys Ser Phe Asn Arg Gly Glu Cys
    210                 215

<210> SEQ ID NO 67
<211> LENGTH: 219
<212> TYPE: PRT
<213> ORGANISM: Artificial sequence
<220> FEATURE:
<223> OTHER INFORMATION: Synthetic

<400> SEQUENCE: 67

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Gln Phe Pro Tyr Thr Phe Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 68
<211> LENGTH: 219
<212> TYPE: PRT
<213> ORGANISM: Artificial sequence
<220> FEATURE:
<223> OTHER INFORMATION: Synthetic

<400> SEQUENCE: 68

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Lys
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Arg Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
            85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 69
<211> LENGTH: 219
<212> TYPE: PRT
<213> ORGANISM: Artificial sequence
<220> FEATURE:
<223> OTHER INFORMATION: Synthetic

<400> SEQUENCE: 69

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Gly Gly Lys Thr Tyr Leu His Trp Tyr Leu Gln Lys Pro Gly Gln Ser
            35                  40                  45

Pro Gln Leu Leu Ile Tyr Lys Val Ser Asn Arg Phe Gly Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
            85                  90                  95

Arg His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 70
<211> LENGTH: 219
<212> TYPE: PRT
<213> ORGANISM: Artificial sequence
<220> FEATURE:
<223> OTHER INFORMATION: Synthetic

<400> SEQUENCE: 70

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Arg Leu Ile His Arg
            20                  25                  30

Asn Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 71
<211> LENGTH: 219
<212> TYPE: PRT
<213> ORGANISM: Artificial sequence
<220> FEATURE:
<223> OTHER INFORMATION: Synthetic

<400> SEQUENCE: 71

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Tyr Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 72
<211> LENGTH: 219
<212> TYPE: PRT
<213> ORGANISM: Artificial sequence
<220> FEATURE:
<223> OTHER INFORMATION: Synthetic

<400> SEQUENCE: 72

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Lys Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Gln Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 73
<211> LENGTH: 219
<212> TYPE: PRT
<213> ORGANISM: Artificial sequence
<220> FEATURE:
<223> OTHER INFORMATION: Synthetic

<400> SEQUENCE: 73

Asp Ile Val Met Thr Gln Thr Pro Leu Ser Leu Pro Val Thr Pro Gly
1               5                   10                  15

Glu Pro Ala Ser Ile Ser Cys Arg Ser Gln Ser Leu Val Arg Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 74
<211> LENGTH: 219
<212> TYPE: PRT
<213> ORGANISM: Artificial sequence
<220> FEATURE:
<223> OTHER INFORMATION: Synthetic

<400> SEQUENCE: 74

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Arg Thr Tyr Leu His Trp Tyr Leu Gln Lys Pro Gly Gln Ser
        35                  40                  45

Pro Gln Leu Leu Ile Tyr Lys Val Ser Asn Arg Phe Arg Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
```

```
                85                  90                  95
Ala Tyr Phe Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
            210                 215
```

<210> SEQ ID NO 75
<211> LENGTH: 219
<212> TYPE: PRT
<213> ORGANISM: Artificial sequence
<220> FEATURE:
<223> OTHER INFORMATION: Synthetic

<400> SEQUENCE: 75

```
Asp Ile Val Met Thr Gln Thr Pro Leu Ser Leu Pro Val Thr Pro Gly
1               5                   10                  15
Glu Pro Ala Ser Ile Ser Cys Thr Ser Ser Gln Val Leu Val His Ser
            20                  25                  30
His Gly Lys Thr Tyr Leu His Trp Tyr Leu Gln Lys Pro Gly Gln Ser
        35                  40                  45
Pro Gln Leu Leu Ile Tyr Lys Val Ser Asn Arg Phe Arg Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Phe Cys Ser Gln Thr
                85                  90                  95
Ala Arg Phe Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
            210                 215
```

-continued

<210> SEQ ID NO 76
<211> LENGTH: 219
<212> TYPE: PRT
<213> ORGANISM: Artificial sequence
<220> FEATURE:
<223> OTHER INFORMATION: Synthetic

<400> SEQUENCE: 76

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 77
<211> LENGTH: 219
<212> TYPE: PRT
<213> ORGANISM: Artificial sequence
<220> FEATURE:
<223> OTHER INFORMATION: Synthetic

<400> SEQUENCE: 77

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Arg Gly Lys Thr Tyr Val His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

```
Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215

<210> SEQ ID NO 78
<211> LENGTH: 219
<212> TYPE: PRT
<213> ORGANISM: Artificial sequence
<220> FEATURE:
<223> OTHER INFORMATION: Synthetic

<400> SEQUENCE: 78

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215

<210> SEQ ID NO 79
<211> LENGTH: 219
```

```
<212> TYPE: PRT
<213> ORGANISM: Artificial sequence
<220> FEATURE:
<223> OTHER INFORMATION: Synthetic

<400> SEQUENCE: 79

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 80
<211> LENGTH: 219
<212> TYPE: PRT
<213> ORGANISM: Artificial sequence
<220> FEATURE:
<223> OTHER INFORMATION: Synthetic

<400> SEQUENCE: 80

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Gly
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Arg Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110
```

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 81
<211> LENGTH: 219
<212> TYPE: PRT
<213> ORGANISM: Artificial sequence
<220> FEATURE:
<223> OTHER INFORMATION: Synthetic

<400> SEQUENCE: 81

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Gly
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala Arg Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 82
<211> LENGTH: 219
<212> TYPE: PRT
<213> ORGANISM: Artificial sequence

```
<220> FEATURE:
<223> OTHER INFORMATION: Synthetic

<400> SEQUENCE: 82

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Arg His Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Arg His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 83
<211> LENGTH: 219
<212> TYPE: PRT
<213> ORGANISM: Artificial sequence
<220> FEATURE:
<223> OTHER INFORMATION: Synthetic

<400> SEQUENCE: 83

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Arg Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Arg His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
```

```
                    115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 84
<211> LENGTH: 219
<212> TYPE: PRT
<213> ORGANISM: Artificial sequence
<220> FEATURE:
<223> OTHER INFORMATION: Synthetic

<400> SEQUENCE: 84

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val Arg Ser
                20                  25                  30

His Gly Lys Thr Tyr Leu His Trp Tyr Leu Gln Lys Pro Gly Gln Ser
            35                  40                  45

Pro Gln Leu Leu Ile Tyr Lys Val Ser Asn Arg Phe Leu Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 85
<211> LENGTH: 219
<212> TYPE: PRT
<213> ORGANISM: Artificial sequence
<220> FEATURE:
<223> OTHER INFORMATION: Synthetic
```

<400> SEQUENCE: 85

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Arg Thr Tyr Leu His Trp Tyr Leu Gln Lys Pro Gly Gln Ser
        35                  40                  45

Pro Gln Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Arg His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 86
<211> LENGTH: 442
<212> TYPE: PRT
<213> ORGANISM: Artificial sequence
<220> FEATURE:
<223> OTHER INFORMATION: Synthetic

<400> SEQUENCE: 86

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125
```

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 87
<211> LENGTH: 445
<212> TYPE: PRT
<213> ORGANISM: Artificial sequence
<220> FEATURE:
<223> OTHER INFORMATION: Synthetic

<400> SEQUENCE: 87

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

```
Gly Asp Ile Asn Pro Asn Arg Gly Gly Thr Thr Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Tyr Tyr Ala Val Gly Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 88
<211> LENGTH: 445
<212> TYPE: PRT
```

<213> ORGANISM: Artificial sequence
<220> FEATURE:
<223> OTHER INFORMATION: Synthetic

<400> SEQUENCE: 88

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gly Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
             385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
                 420                 425                 430

His Tyr Thr Gln Lys Ser Leu Ser Leu Ser Pro Gly Lys
                 435                 440                 445
```

<210> SEQ ID NO 89
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: x is R or T
<220> FEATURE:
<221> NAME/KEY: MISC_FEATURE
<222> LOCATION: (5)..(5)
<223> OTHER INFORMATION: x is S,R, or V
<220> FEATURE:
<221> NAME/KEY: MISC_FEATURE
<222> LOCATION: (7)..(7)
<223> OTHER INFORMATION: x is V, I, or R
<220> FEATURE:
<221> NAME/KEY: MISC_FEATURE
<222> LOCATION: (8)..(8)
<223> OTHER INFORMATION: x is H or R
<220> FEATURE:
<221> NAME/KEY: MISC_FEATURE
<222> LOCATION: (9)..(9)
<223> OTHER INFORMATION: x is S, R, G, or K
<220> FEATURE:
<221> NAME/KEY: MISC_FEATURE
<222> LOCATION: (10)..(10)
<223> OTHER INFORMATION: x is H, N, R, K, or G
<220> FEATURE:
<221> NAME/KEY: MISC_FEATURE
<222> LOCATION: (12)..(12)
<223> OTHER INFORMATION: x is K or R
<220> FEATURE:
<221> NAME/KEY: MISC_FEATURE
<222> LOCATION: (15)..(15)
<223> OTHER INFORMATION: x is L or V

<400> SEQUENCE: 89

```
Xaa Ser Ser Gln Xaa Leu Xaa Xaa Xaa Gly Xaa Thr Tyr Xaa His
1               5                   10                  15
```

<210> SEQ ID NO 90
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: x is S, K, or R
<220> FEATURE:
<221> NAME/KEY: MISC_FEATURE
<222> LOCATION: (4)..(4)
<223> OTHER INFORMATION: x is N, K, or H
<220> FEATURE:
<221> NAME/KEY: MISC_FEATURE
<222> LOCATION: (7)..(7)
<223> OTHER INFORMATION: x is S, F, G, K, R, Y or L

<400> SEQUENCE: 90

```
Lys Val Xaa Xaa Arg Phe Xaa
```

-continued

```
<210> SEQ ID NO 91
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: x is A or R
<220> FEATURE:
<221> NAME/KEY: MISC_FEATURE
<222> LOCATION: (5)..(5)
<223> OTHER INFORMATION: x is H, R, Q or Y
<220> FEATURE:
<221> NAME/KEY: MISC_FEATURE
<222> LOCATION: (8)..(8)
<223> OTHER INFORMATION: x is Y or R

<400> SEQUENCE: 91

Ser Gln Thr Xaa Xaa Phe Pro Xaa Thr
1               5

<210> SEQ ID NO 92
<211> LENGTH: 16
<212> TYPE: PRT
<213> ORGANISM: Artificial sequence
<220> FEATURE:
<223> OTHER INFORMATION: Synthetic

<400> SEQUENCE: 92

Arg Ser Ser Gln Arg Leu Val His Ser His Gly Lys Thr Tyr Leu His
1               5                   10                  15

<210> SEQ ID NO 93
<211> LENGTH: 18
<212> TYPE: PRT
<213> ORGANISM: Artificial sequence
<220> FEATURE:
<223> OTHER INFORMATION: Synthetic

<400> SEQUENCE: 93

Gly Asp Thr Ser Pro Trp His Leu Ser Asn Val Ser Ser Thr Gly Ser
1               5                   10                  15

Ile Asp

<210> SEQ ID NO 94
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: x=phosphoserine
<220> FEATURE:
<221> NAME/KEY: MISC_FEATURE
<222> LOCATION: (9)..(9)
<223> OTHER INFORMATION: x=phosphoserine

<400> SEQUENCE: 94

Gly Asp Thr Xaa Pro Arg His Leu Xaa Asn Val Ser Ser Thr Gly Ser
1               5                   10                  15

Ile Asp
```

```
<210> SEQ ID NO 95
<211> LENGTH: 18
<212> TYPE: PRT
<213> ORGANISM: Artificial sequence
<220> FEATURE:
<223> OTHER INFORMATION: Synthetic

<400> SEQUENCE: 95

Gly Asp Thr Ser Pro Arg His Leu Ser Asn Val Ser Ser Thr Gly Ser
1               5                   10                  15

Ile Asp

<210> SEQ ID NO 96
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: x= phosphoserine

<400> SEQUENCE: 96

Gly Asp Thr Xaa Pro Arg His Leu Ser Asn Val Ser Ser Thr Gly Ser
1               5                   10                  15

Ile Asp

<210> SEQ ID NO 97
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: x= phosphoserine

<400> SEQUENCE: 97

Gly Asp Thr Ser Pro Arg His Leu Xaa Asn Val Ser Ser Thr Gly Ser
1               5                   10                  15

Ile Asp
```